(12) United States Patent
Sakita et al.

(10) Patent No.: US 9,223,211 B2
(45) Date of Patent: Dec. 29, 2015

(54) PHOTOSENSITIVE RESIN COMPOSITIONS, PROCESSES FOR PREPARING CURED FILMS, THE RESULTING CURED FILMS, ORGANIC EL DISPLAY DEVICES AND LIQUID CRYSTAL DISPLAY DEVICES

(71) Applicant: FUJIFILM Corporation, Minato-ku, Tokyo (JP)

(72) Inventors: Kyouhei Sakita, Haibara-gun (JP); Shinji Fujimoto, Haibara-gun (JP); Mikio Nakagawa, Haibara-gun (JP); Kenta Yamazaki, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/607,644

(22) Filed: Jan. 28, 2015

(65) Prior Publication Data
US 2015/0148546 A1 May 28, 2015

Related U.S. Application Data

(63) Continuation of application No. PCT/JP2013/065324, filed on Jun. 3, 2013.

(30) Foreign Application Priority Data

| Jul. 30, 2012 | (JP) | ................................. 2012-168441 |
| Oct. 30, 2012 | (JP) | ................................. 2012-238613 |
| Mar. 15, 2013 | (JP) | ................................. 2013-053262 |

(51) Int. Cl.
| *C07D 277/84* | (2006.01) |
| *C07D 277/64* | (2006.01) |
| *C07D 417/12* | (2006.01) |
| *C07D 263/56* | (2006.01) |
| *C07D 263/60* | (2006.01) |
| *G03F 7/027* | (2006.01) |
| *C08F 12/22* | (2006.01) |
| *C08F 20/26* | (2006.01) |
| *G03F 7/40* | (2006.01) |
| *G03F 7/004* | (2006.01) |
| *G03F 7/039* | (2006.01) |
| *H05B 33/22* | (2006.01) |
| *H01L 27/32* | (2006.01) |

(52) U.S. Cl.
CPC .............. *G03F 7/027* (2013.01); *C07D 263/56* (2013.01); *C07D 263/60* (2013.01); *C07D 277/64* (2013.01); *C07D 277/84* (2013.01); *C07D 417/12* (2013.01); *C08F 12/22* (2013.01); *C08F 20/26* (2013.01); *G03F 7/0045* (2013.01); *G03F 7/0392* (2013.01); *G03F 7/0397* (2013.01); *G03F 7/40* (2013.01); *H01L 27/3258* (2013.01); *H05B 33/22* (2013.01)

(58) Field of Classification Search
USPC .......................................... 548/150, 180, 217
See application file for complete search history.

(56) References Cited

U.S. PATENT DOCUMENTS

| 8,628,907 B2 | 1/2014 | Ishiji et al. |
| 2012/0045616 A1 | 2/2012 | Ishiji et al. |
| 2014/0005409 A1 | 1/2014 | Ishiji et al. |

FOREIGN PATENT DOCUMENTS

| EP | 2420890 A1 * | 2/2012 |
| JP | 2012-042836 A | 3/2012 |
| WO | WO-2011/089967 A1 * | 7/2011 |

OTHER PUBLICATIONS

An English translation of WO 2011/089967 A1, 2011.*
International Preliminary Report on Patentability dated Feb. 12, 2015, issued in counterpart International Application No. PCT/JP2013/065324.
International Search Report for PCT/JP2013/065324 dated Jan. 23, 2015 and Written Opinion.

* cited by examiner

*Primary Examiner* — Laura L. Stockton
(74) *Attorney, Agent, or Firm* — Sughrue Mion, PLLC

(57) ABSTRACT

Provided is a photosensitive resin composition having high sensitivity and storage stability. The photosensitive resin composition comprises (A) a polymer component including a polymer satisfying at least one of (1) and (2) below:
(1) a polymer comprising (a1) a structural unit containing a group in which an acid group is protected by an acid-dissociable group, and (a2) a structural unit containing a crosslinkable group, and
(2) a polymer comprising (a1) a structural unit containing a group in which an acid group is protected by an acid-dissociable group, and a polymer comprising (a2) a structural unit containing a crosslinkable group;
(B) a compound represented by formula (I) below; and
(C) a solvent;

formula (I)

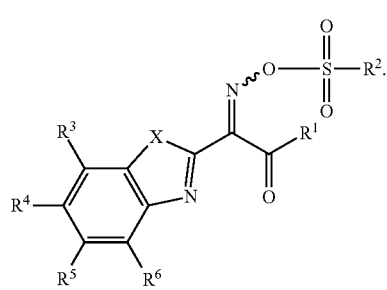

7 Claims, 1 Drawing Sheet

PHOTOSENSITIVE RESIN COMPOSITIONS, PROCESSES FOR PREPARING CURED FILMS, THE RESULTING CURED FILMS, ORGANIC EL DISPLAY DEVICES AND LIQUID CRYSTAL DISPLAY DEVICES

CROSS-REFERENCE TO RELATED APPLICATIONS

This application is a Continuation of PCT International Application No. PCT/JP2013/065324 filed on Jun. 3, 2013, which claims priority under 35 U.S.C §119(a) to Japanese Patent Application No. 2012-168441 filed on Jul. 30, 2012, Japanese Patent Application No. 2012-238613 filed on Oct. 30, 2012, and Japanese Patent Application No. 2013-053262 filed on Mar. 15, 2013. Each of the above application(s) is hereby expressly incorporated by reference, in its entirety, into the present application.

TECHNICAL FIELD

The present invention relates to photosensitive resin compositions (hereinafter sometimes simply referred to as "compositions of the present invention"). It also relates to processes for preparing cured films using the photosensitive resin compositions; cured films obtained by curing the photosensitive compositions; and various image display devices using the cured films.

More specifically, it relates to photosensitive resin compositions well-suitable for forming planarization layers, protective layers and interlayer insulating layers of electronic components such as liquid crystal display devices, organic EL display devices, integrated circuit devices, solid-state image sensors and the like; as well as processes for preparing cured films using such compositions.

BACKGROUND ART

Organic EL display devices, liquid crystal display devices and the like are provided with a patterned interlayer insulating layer. Photosensitive resin compositions are widely used to form this interlayer insulating layer because sufficient flatness can be achieved with fewer steps for obtaining a desired pattern shape. Known photosensitive resin compositions include, for example, those described in patent document 1.

REFERENCES

Patent Documents

Patent document 1: JP-A2012-42836.

SUMMARY OF THE INVENTION

Problems to be Solved by the Invention

We reviewed patent document 1 to find that the acid generators specifically disclosed in patent document 1 had low sensitivity, low storage stability, or low transparency after heat treatment (transparency after heating). We reviewed this point to find that the acid generators specifically disclosed in patent document 1 were oxime sulfonates having a heterocyclic structure and an electron-withdrawing group and that such structure influenced these properties. In other words, the oxime sulfonates described in patent document 1 can be further improved in their sensitivity by enhancing the electron-withdrawing ability of the electron-withdrawing group, but oxime sulfonates with improved sensitivity were found to have low storage stability. Conversely, oxime sulfonates with improved storage stability were found to have low sensitivity.

Further, some oxime sulfonates described in patent document 1 were found to have low transparency.

The present invention aims to solve the problems described above, thereby providing photosensitive resin compositions having high storage stability and transparency after heating while maintaining high sensitivity.

It also aims to provide processes for forming cured films using such photosensitive resin compositions, the resulting cured films, organic EL display devices, and liquid crystal display devices.

Means to Solve the Problems

As a result of careful studies, we found that the problems described above can be solved by using a specific structure as the heterocyclic structure and $C(=O)R^1$ as the electron-withdrawing group.

Specifically, the above problems were solved by the following means for solving the problems <1>, preferably <2> to <15>.

<1> A photosensitive resin composition comprising:
(A) a polymer component including a polymer satisfying at least one of (1) and (2) below:
  (1) a polymer comprising (a1) a structural unit containing a group in which an acid group is protected by an acid-dissociable group, and (a2) a structural unit containing a crosslinkable group, and
  (2) a polymer comprising (a1) a structural unit containing a group in which an acid group is protected by an acid-dissociable group, and a polymer comprising (a2) a structural unit containing a crosslinkable group;
and a polymer comprising (a2) a structural unit containing a crosslinkable group;
(B) a compound represented by formula (I) below; and
(C) a solvent;

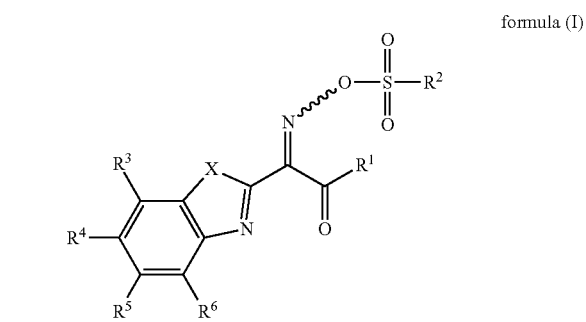

formula (I)

wherein $R^1$ represents an alkyl group or an aryl group; $R^2$ represents an alkyl group, an aryl group or a heteroaryl group; $R^3$ to $R^6$ each represent a hydrogen atom, an alkyl group, an aryl group or a halogen atom; $R^3$ and $R^4$, $R^4$ and $R^5$, or $R^5$ and $R^6$ may be taken together to form an alicyclic ring or an aromatic ring; and X represents —O— or —S—.

<2> The photosensitive resin composition according to <1>, wherein $R^1$ is an alkyl group containing 3 to 10 carbon atoms, or an aryl group containing 6 to 12 carbon atoms.

<3> The photosensitive resin composition according to <1> or <2>, wherein $R^1$ is an alkyl group having a branched-chain structure, a cyclic alkyl group, or a phenyl group.

<4> The photosensitive resin composition according to any one of <1> to <3>, wherein the structural unit containing a group in which an acid group is protected by an acid-dissociable group (a1) is a structural unit containing a group in which a carboxyl group is protected by an acid-dissociable group.

<5> The photosensitive resin composition according to any one of <1> to <4>, wherein the structural unit containing a crosslinkable group (a2) is selected from a structural unit containing an epoxy group and/or an oxetanyl group; a structural unit containing an ethylenically unsaturated group; and a structural unit containing a group represented by —NH—CH$_2$—O—R wherein R is an alkyl group containing 1 to 20 carbon atoms.

<6> The photosensitive resin composition according to any one of <1> to <5>, wherein the compound represented by formula (I) above is selected from the compounds shown below:

B-1
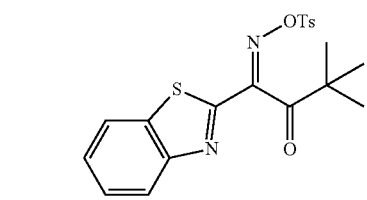

B-2
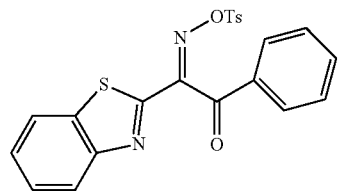

B-3
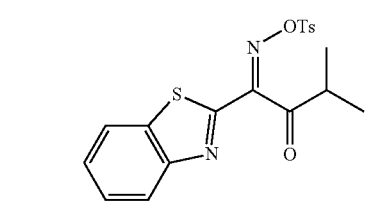

B-4
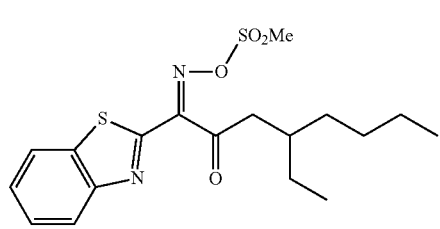

B-5
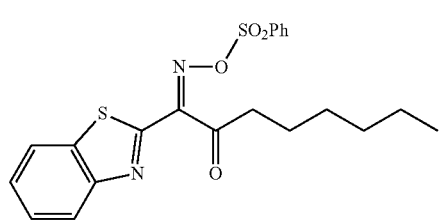

B-6
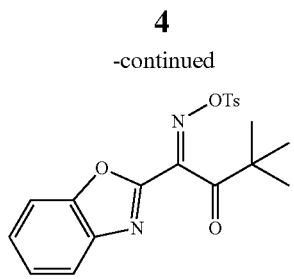

B-7
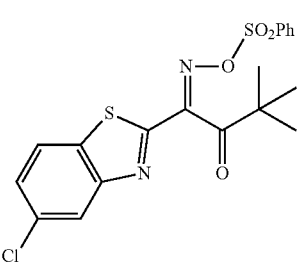

B-8
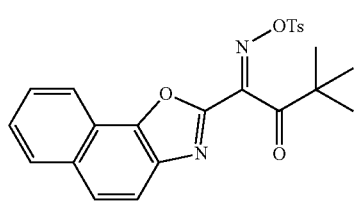

B-9
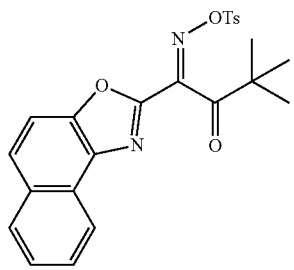

B-10
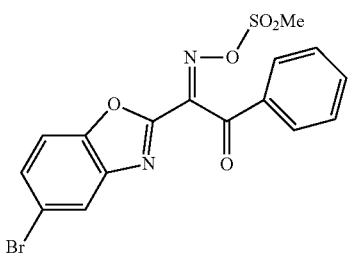

B-11
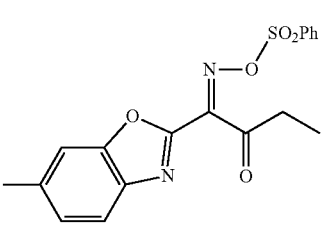

B-12
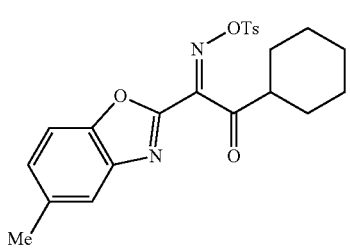

-continued

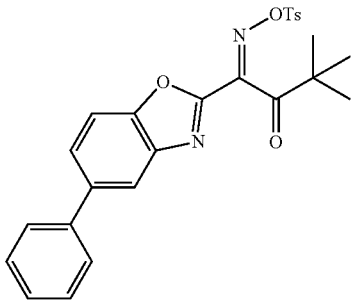

B-27

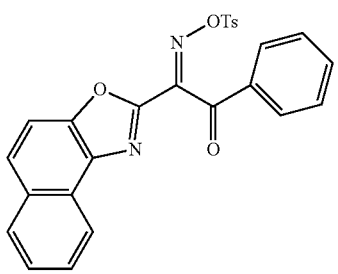

B-28

B-29

<7> A process for preparing a cured film, comprising:
(1) coating a photosensitive resin composition according to any one of <1> to <6> by coating on a substrate;
(2) removing the solvent from the applied photosensitive resin composition;
(3) exposing the photosensitive resin composition freed from the solvent to an active radiation;
(4) developing the exposed photosensitive resin composition by an aqueous developer; and
(5) postbaking the developed photosensitive resin composition to thermally cure it.
<8> The process for preparing a cured film according to <7>, comprising wholly exposing the developed photosensitive resin composition after the developing and before the postbaking.
<9> A cured film formed by a process according to <7> or <8>.
<10> The cured film according to <9>, which is an interlayer insulating film.
<11> An organic EL display device or a liquid crystal display device comprising a cured film according to <9> or <10>.

<12> A compound represented by formula (I) below:

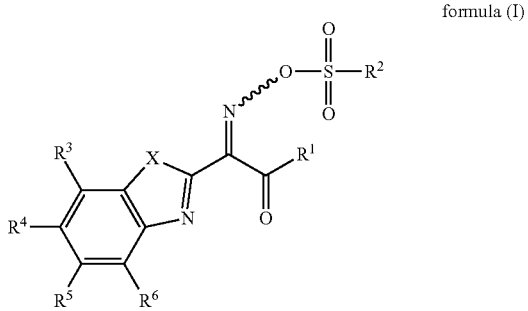

formula (I)

wherein $R^1$ represents an alkyl group or an aryl group; $R^2$ represents an alkyl group, an aryl group or a heteroaryl group; $R^3$ to $R^6$ each represent a hydrogen atom, an alkyl group, an aryl group or a halogen atom; $R^3$ and $R^4$, $R^4$ and $R^5$, or $R^5$ and $R^6$ may be taken together to form an alicyclic ring or an aromatic ring; and X represents —O— or —S—.
<13> The compound according to <12>, wherein $R^1$ is an alkyl group containing 3 to 10 carbon atoms, or an aryl group containing 6 to 12 carbon atoms.
<14> The compound according to <12> or <13>, wherein $R^1$ is an alkyl group having a branched-chain structure, a cyclic alkyl group, or a phenyl group.
<15> The compound according to <12>, wherein the compound represented by formula (I) below is any one of compounds B-1 to B-29 shown below;

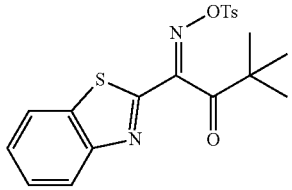

B-1

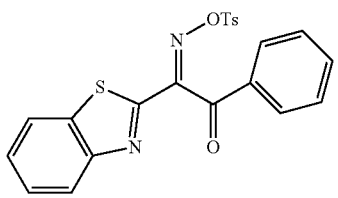

B-2

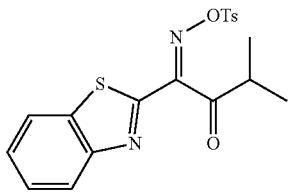

B-3

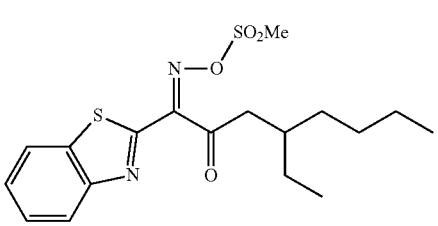

B-4

B-5 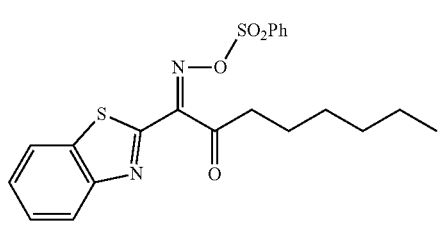
B-6 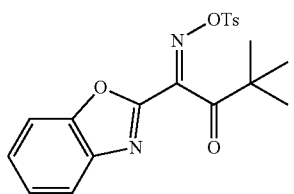
B-7 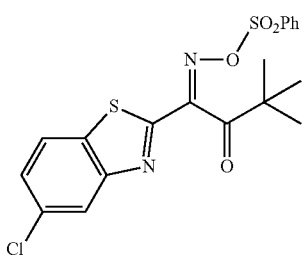
B-8 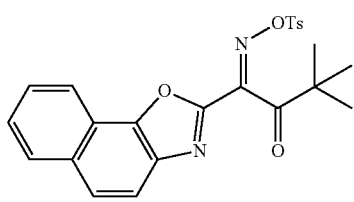
B-9 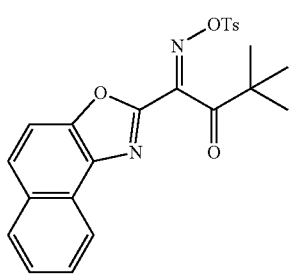
B-10 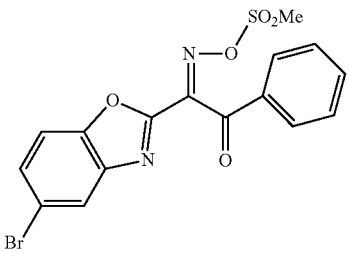
B-11 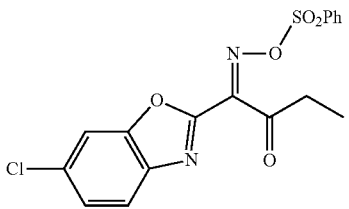
B-12 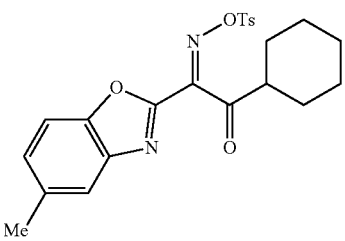
B-13 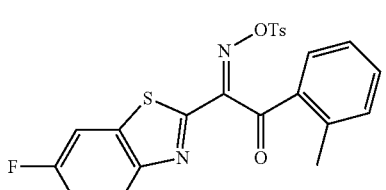
B-14 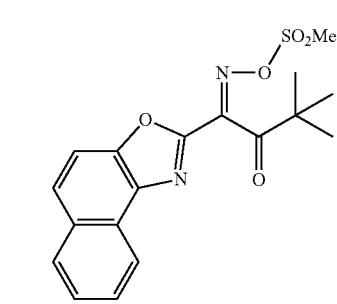
B-15 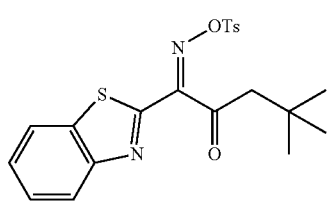
B-16 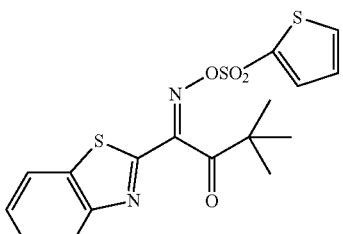
B-17 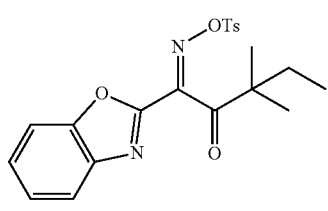
B-18 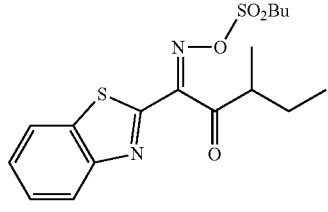

-continued

B-19
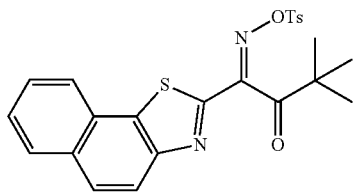

B-20
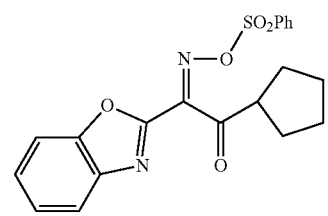

B-21
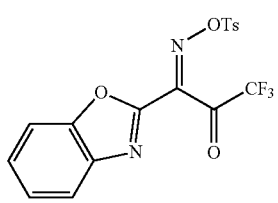

B-22
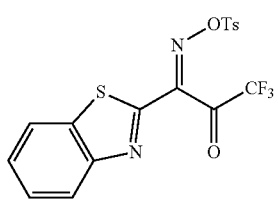

B-23
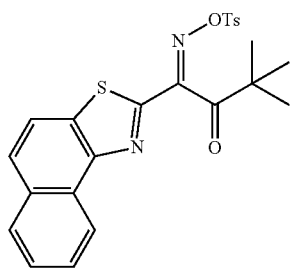

B-24
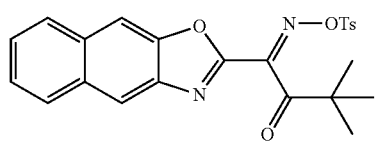

B-25
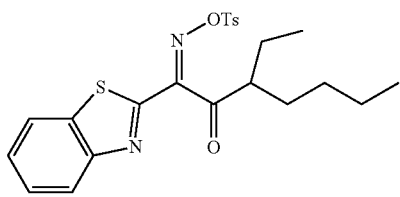

-continued

B-26
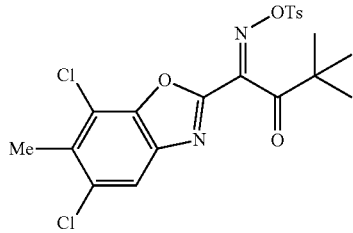

B-27
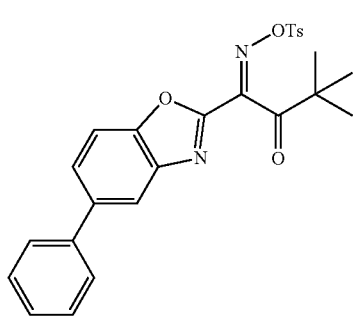

B-28
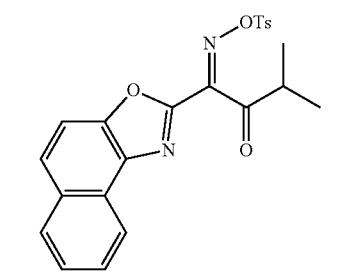

B-29
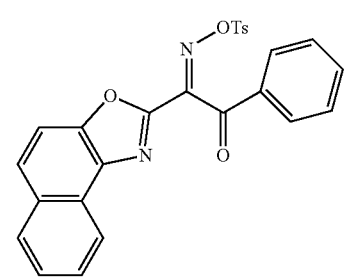

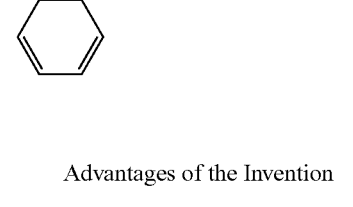

Advantages of the Invention

The present invention made it possible to provide photosensitive resin compositions having high sensitivity and storage stability.

THE MOST PREFERRED EMBODIMENTS OF THE INVENTION

Figure 1:
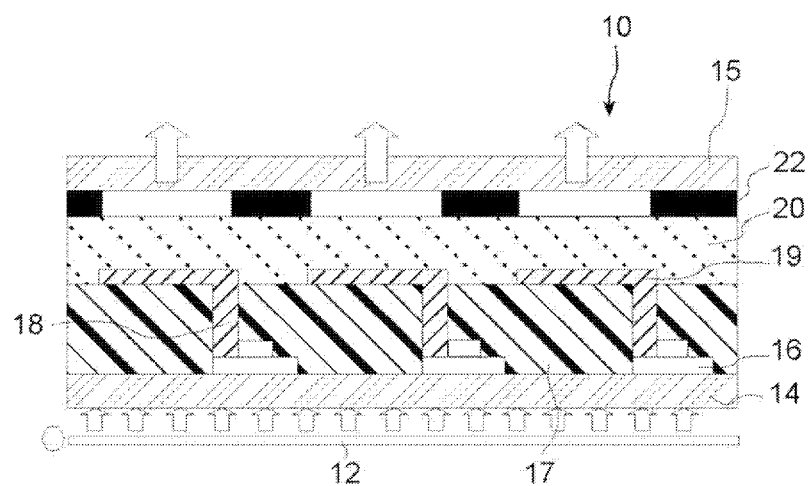
FIG. 1 shows a schematic diagram of an example of a liquid crystal display device. A schematic sectional view of an active matrix array in a liquid crystal display device is shown, which comprises a cured film 17 as an interlayer insulating layer.

The present invention will be explained in detail below. Some features may be explained below with reference to typical embodiments of the present invention, but the present invention is not limited to such embodiments. As used herein, the numerical ranges expressed with "to" are used to mean the ranges including the values indicated before and after "to" as lower and upper limits.

As used herein, any reference to a group (group of atoms) without indicating that the group is substituted or unsubstituted includes the group not only unsubstituted but also substituted. For example, the expression "alkyl group" means to include not only an alkyl group having no substituent (an unsubstituted alkyl group) but also an alkyl group having a substituent (a substituted alkyl group).

The photosensitive resin compositions of the present invention (hereinafter sometimes referred to as "compositions of the present invention") are preferably used as positive working photosensitive resin compositions.

The photosensitive resin compositions of the present invention are characterized in that they comprise:
(A) a polymer component including a polymer satisfying at least one of (1) and (2) below:
(1) a polymer comprising (a1) a structural unit containing a group in which an acid group is protected by an acid-dissociable group, and (a2) a structural unit containing a crosslinkable group, and
(2) a polymer comprising (a1) a structural unit containing a group in which an acid group is protected by an acid-dissociable group, and a polymer comprising (a2) a structural unit containing a crosslinkable group;
(B) a compound represented by formula (I) below:

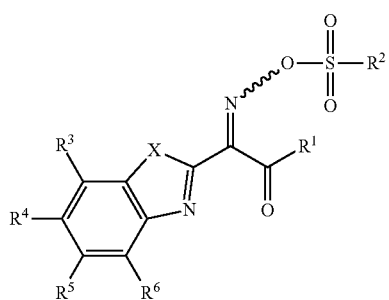

wherein $R^1$ represents an alkyl group or an aryl group; $R^2$ represents an alkyl group, an aryl group or a heteroaryl group; $R^3$ to $R^6$ each represent a hydrogen atom, an alkyl group, an aryl group or a halogen atom; $R^3$ and $R^4$, $R^4$ and $R^5$, or $R^5$ and $R^6$ may be taken together to form an alicyclic ring or an aromatic ring; and X represents —O— or —S—; and (C) a solvent.

The present invention makes it possible to provide photosensitive resin compositions having high sensitivity and storage stability.

Further, transparency after heating can also be improved. The compositions of the present invention will be explained in detail below.

<(A) Polymer Component>

The compositions of the present invention comprise a polymer component including at least one of (1) a polymer comprising (a1) a structural unit containing a group in which an acid group is protected by an acid-dissociable group, and (a2) a structural unit containing a crosslinkable group; and (2) a polymer comprising (a1) a structural unit containing a group in which an acid group is protected by an acid-dissociable group, and a polymer comprising (a2) a structural unit containing a crosslinkable group. Further, they may comprise polymers other than these components. As used herein, the polymer component (A) (hereinafter sometimes referred to as "component (A)") means to include (1) and/or (2) defined above as well as other polymers added as appropriate, unless otherwise specified.

<<Structural Unit (A1)>>

Component A comprises at least (a1) a structural unit containing a group in which an acid group is protected by an acid-dissociable group. When the component (A) comprises the structural unit (a1), very sensitive photosensitive resin compositions can be obtained.

In the present invention, the "group in which an acid group is protected by an acid-dissociable group" is not specifically limited, and known acid groups and acid-decomposable groups can be used. Specific acid groups preferably include a carboxyl group and a phenolic hydroxyl group. On the other hand, acid-decomposable groups that can be used include groups that are relatively easy to cleave by acids (e.g., acetal functional groups such as an ester structure represented by formula (Al) described later, a tetrahydropyranyl ester group, or a tetrahydrofuranyl ester group) and groups that are relatively difficult to cleave by acids (e.g., tertiary alkyl groups such as a tert-butyl ester group, and tertiary alkyl carbonate groups such as a tert-butyl carbonate group).

The structural unit containing a group in which an acid group is protected by an acid-dissociable group (a1) is preferably a structural unit containing a group in which a carboxyl group is protected by an acid-dissociable group or a structural unit containing a group in which a phenolic hydroxyl group is protected by an acid-dissociable group.

The structural unit containing a group in which a carboxyl group is protected by an acid-dissociable group (a1-1) and the structural unit containing a group in which a phenolic hydroxyl group is protected by an acid-dissociable group (a1-2) will be explained in order below.

<<<(a1-1) Structural Unit Containing a Group in which a Carboxyl Group is Protected by an Acid-Dissociable Group>>>

The structural unit containing a group in which a carboxyl group is protected by an acid-dissociable group (a1-1) is a structural unit containing a group in which a carboxyl group protected by the acid-decomposable group explained in detail below.

The structural unit containing a carboxyl group that can be used as the structural unit containing a group in which a carboxyl group is protected by an acid-dissociable group (a1-1) is not specifically limited, and known structural units can be used.

For example, it may be (a1-1-1) a structural unit derived from an unsaturated carboxylic acid containing at least one carboxyl group in the molecule such as an unsaturated monocarboxylic acid, unsaturated dicarboxylic acid or unsaturated tricarboxylic acid or the like, or (a1-1-2) a structural unit containing both of an ethylenically unsaturated group and a structure derived from an acid anhydride.

The structural unit derived from an unsaturated carboxylic acid containing at least one carboxyl group in the molecule or the like (a1-1-1) and the structural unit containing both of an ethylenically unsaturated group and a structure derived from an acid anhydride (a1-1-2) used as the structural unit containing a carboxyl group will be explained in order below.

<<<<(a1-1-1) Structural Unit Derived from an Unsaturated Carboxylic Acid Containing at Least One Carboxyl Group in the Molecule or the Like>>>>

Unsaturated carboxylic acids used in the present invention for the structural unit derived from an unsaturated carboxylic acid containing at least one carboxyl group in the molecule or the like (a1-1-1) include the following. Unsaturated monocarboxylic acids include, for example, acrylic acid, methacrylic acid, crotonic acid, α-chloroacrylic acid, cinnamic acid, 2-(meth)acryloyloxyethyl succinic acid, 2-(meth)acryloyloxyethyl hexahydrophthalic acid, 2-(meth)acryloyloxyethyl phthalic acid and the like.

Unsaturated dicarboxylic acids include, for example, maleic acid, fumaric acid, itaconic acid, citraconic acid, mesaconic acid and the like. Unsaturated polycarboxylic acids used to obtain the structural unit containing a carboxyl group may be their anhydrides. Specifically, examples include maleic anhydride, itaconic anhydride, citraconic anhydride and the like.

Unsaturated polycarboxylic acids may also be mono(2-methacryloyloxyalkyl)esters of polycarboxylic acids such as mono(2-acryloyloxyethyl)succinate, mono(2-methacryloyloxyethyl)succinate, mono(2-acryloyloxyethyl)phthalate, mono(2-methacryloyloxyethyl)phthalate and the like. Further, unsaturated polycarboxylic acids may also be mono (meth)acrylates of dicarboxy terminated polymers thereof such as ω-carboxypolycaprolactone monoacrylate, ω-carboxypolycaprolactone monomethacrylate and the like. Still further examples of unsaturated carboxylic acids that can be used include 2-carboxyethyl acrylate ester, 2-carboxyethyl methacrylate ester, monoalkyl maleate esters, monoalkyl fumarate esters, 4-carboxystyrene and the like.

Among others, acrylic acid, methacrylic acid, 2-(meth)acryloyloxyethyl succinic acid, 2-(meth)acryloyloxyethyl hexahydrophthalic acid, 2-(meth)acryloyloxyethyl phthalic acid or an unsaturated polycarboxylic anhydride or the like is preferably used to form the structural unit derived from an unsaturated carboxylic acid containing at least one carboxyl group in the molecule or the like (a1-1-1), more preferably acrylic acid, methacrylic acid, or 2-(meth)acryloyloxyethyl hexahydrophthalic acid to improve developability.

The structural unit derived from an unsaturated carboxylic acid containing at least one carboxyl group in the molecule or the like (a1-1) may consist of a single unit or two or more different units.

<<<<(a1-1-2) Structural Unit Containing Both of an Ethylenically Unsaturated Group and a Structure Derived from an Acid Anhydride>>>>

The structural unit containing both of an ethylenically unsaturated group and a structure derived from an acid anhydride (a1-1-2) is preferably a unit derived from a monomer obtained by reacting a hydroxyl group present in a structural unit containing an ethylenically unsaturated group with an acid anhydride.

Examples of the acid anhydride that can be used include known ones, specifically dibasic acid anhydrides such as maleic anhydride, succinic anhydride, itaconic anhydride, phthalic anhydride, tetrahydrophthalic anhydride, hexahydrophthalic anhydride, chlorendic anhydride and the like; as well as trimellitic anhydride, pyromellitic anhydride, benzophenone tetracarboxylic anhydride, biphenyl tetracarboxylic anhydride and the like. Among them, phthalic anhydride, tetrahydrophthalic anhydride, or succinic anhydride is preferred to improve developability.

The proportion of the acid anhydride to be reacted with the hydroxyl group is preferably 10 to 100 mol %, more preferably 30 to 100 mol % to improve developability.

<<<<Acid-Decomposable Groups that can be Used in the Structural Unit (a1-1)>>>>

The acid-decomposable groups that can be used in the structural unit containing a group in which a carboxyl group is protected by an acid-dissociable group (a1-1) include the acid-decomposable groups described above.

Among these acid-decomposable groups, preferred are those by which the carboxyl group is protected as an acetal to improve fundamental properties of the photosensitive resin compositions, especially sensitivity and pattern shape, the ease of forming contact holes, and storage stability of the photosensitive resin compositions. Among the acid-decomposable groups, more preferred are those by which the carboxyl group is protected as an acetal represented by formula (a1-10) below to improve sensitivity. It should be noted that when the carboxyl group is a carboxyl group protected as an acetal represented by formula (a1-10) below, the protected carboxyl group as a whole has the structure —(C=O)—O—CR$^{101}$R$^{102}$(OR$^{103}$)

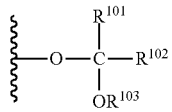

formula (a1-10)

In formula (a1-10), R$^{101}$ and R$^{102}$ each represent a hydrogen atom or an alkyl group, provided that both of R$^{101}$ and R$^{102}$ do not represent a hydrogen atom; R$^{103}$ represents an alkyl group; R$^{101}$ or R$^{102}$ may be taken together with R$^{103}$ to form a cyclic ether.

In formula (a1-10) above, R$^{101}$ to R$^{103}$ each represent a hydrogen atom or an alkyl group, wherein the alkyl group may be straight-chain, branched-chain or cyclic. However, both of R$^{101}$ and R$^{102}$ do not represent a hydrogen atom, and at least one of R$^{101}$ and R$^{102}$ represents an alkyl group.

When R$^{101}$, R$^{102}$ and R$^{103}$ represent an alkyl group in formula (a1-10) above, the alkyl group may be straight-chain, branched-chain or cyclic.

The straight-chain or branched-chain alkyl group preferably contains 1 to 12 carbon atoms, more preferably 1 to 6 carbon atoms, still more preferably 1 to 4 carbon atoms. Specifically, examples include methyl, ethyl, n-propyl, i-propyl, n-butyl, i-butyl, sec-butyl, tert-butyl, n-pentyl, neopentyl, n-hexyl, thexyl (2,3-dimethyl-2-butyl), n-heptyl, n-octyl, 2-ethylhexyl, n-nonyl, n-decyl and the like.

The cyclic alkyl group preferably contains 3 to 12 carbon atoms, more preferably 4 to 8 carbon atoms, still more preferably 4 to 6 carbon atoms. Such cyclic alkyl groups include, for example, cyclopropyl, cyclobutyl, cyclopentyl, cyclohexyl, cycloheptyl, cyclooctyl, norbornyl, isobornyl and the like.

The alkyl group may be substituted by a substituent such as a halogen atom, an aryl group or an alkoxy group. When it is substituted by a halogen atom, R$^{101}$, R$^{102}$, and R$^{103}$ represent a haloalkyl group, or when it is substituted by an aryl group, R$^{101}$, R$^{102}$, and R$^{103}$ represent an aralkyl group.

Examples of the halogen atom include fluorine atom, chlorine atom, bromine atom, and iodine atom, among which fluorine atom or chlorine atom is preferred.

Further, the aryl group is preferably an aryl group containing 6 to 20 carbon atoms, more preferably 6 to 12 carbon atoms, examples of which specifically include phenyl, α-methylphenyl, naphthyl and the like, and examples of aryl-substituted alkyl groups, i.e., aralkyl groups include benzyl, α-methylbenzyl, phenethyl, naphthylmethyl and the like.

The alkoxy group is preferably an alkoxy group containing 1 to 6 carbon atoms, more preferably 1 to 4 carbon atoms, still more preferably methoxy or ethoxy.

When the alkyl group is a cycloalkyl group, the cycloalkyl group may be substituted by a straight-chain or branched-chain alkyl group containing 1 to 10 carbon atoms, or when the alkyl group is a straight-chain or branched-chain alkyl group, it may be substituted by a cycloalkyl group containing 3 to 12 carbon atoms.

These substituents may be further substituted by the substituents described above.

When $R^{101}$, $R^{102}$ and $R^{103}$ represent an aryl group in formula (a1-10) above, the aryl group preferably contains 6 to 12 carbon atoms, more preferably 6 to 10 carbon atoms. The aryl group may be substituted by a substituent, examples of which preferably include alkyl groups containing 1 to 6 carbon atoms. Examples of aryl groups include, for example, phenyl, tolyl, cumenyl, 1-naphthyl and the like Alternatively, $R^{101}$, $R^{102}$ and $R^{103}$ can be taken together with the carbon atom to which they are attached to form a ring.

The ring structures formed by $R^{101}$ and $R^{102}$, $R^{101}$ and $R^{103}$, or $R^{102}$ and $R^{103}$ taken together include, for example, cyclobutyl, cyclopentyl, cyclohexyl, cycloheptyl, tetrahydrofuranyl, adamantyl and tetrahydropyranyl and the like.

In formula (a1-10) above, any one of $R^{101}$ and $R^{102}$ is preferably a hydrogen atom or a methyl group.

Radically polymerizable monomers used for forming the structural unit containing a protected carboxyl group represented by formula (a1-10) above may be commercially available or may be synthesized by a known method. For example, they can be synthesized by the synthesis method described in paragraphs 0037 to 0040 of JP-A2011-221494 or the like.

A first preferred embodiment of the structural unit containing a group in which a carboxyl group is protected by an acid-dissociable group (a1-1) is a structural unit represented by the formula shown below:

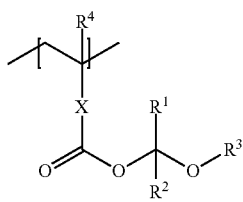

wherein $R^1$ and $R^2$ each represent a hydrogen atom, an alkyl group or an aryl group, and at least any one of $R^1$ and $R^2$ represents an alkyl group or an aryl group, $R^3$ represents an alkyl group or an aryl group, or $R^1$ or $R^2$ may be joined with $R^3$ to form a cyclic ether, $R^4$ represents a hydrogen atom or a methyl group, and X represents a single bond or an arylene group.

When $R^1$ and $R^2$ represent an alkyl group, it is preferably an alkyl group containing 1 to 10 carbon atoms. When $R^1$ and $R^2$ represent an aryl group, it is preferably a phenyl group. Preferably, $R^1$ and $R^2$ each represent a hydrogen atom or an alkyl group containing 1 to 4 carbon atoms.

$R^3$ represents an alkyl group or an aryl group, preferably an alkyl group containing 1 to 10 carbon atoms, more preferably an alkyl group containing 1 to 6 carbon atoms.

X represents a single bond or an arylene group, preferably a single bond.

A second preferred embodiment of the structural unit containing a group in which a carboxyl group is protected by an acid-dissociable group (a1-1) is a structural unit represented by the formula shown below:

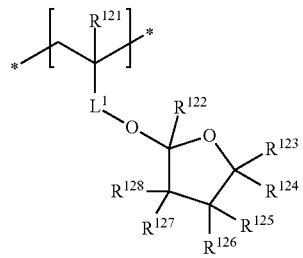

wherein $R^{121}$ represents a hydrogen atom or an alkyl group containing 1 to 4 carbon atoms, $L^1$ represents a carbonyl group or a phenylene group, and $R^{122}$ to $R^{128}$ each represent a hydrogen atom or an alkyl group containing 1 to 4 carbon atoms.

Preferably, $R^{121}$ represents a hydrogen atom or a methyl group.

Preferably, $L^1$ represents a carbonyl group.

Preferably, $R^{122}$ to $R^{128}$ represent a hydrogen atom.

Preferred specific examples of the structural unit containing a group in which a carboxyl group is protected by an acid-dissociable group (a1-1) include the structural units shown below, wherein R represents a hydrogen atom or a methyl group.

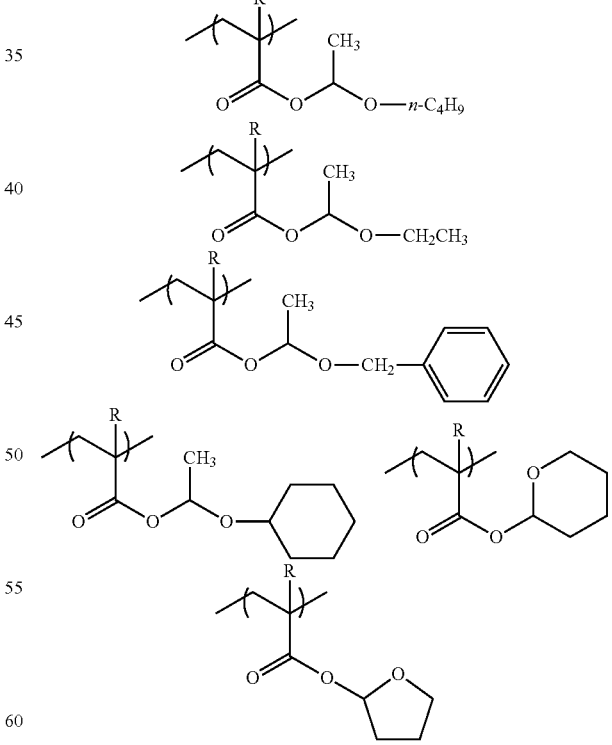

<<<(a1-2) Structural Unit Containing a Group in which a Phenolic Hydroxyl Group is Protected by an Acid-Dissociable Group>>>

The structural unit containing a group in which a phenolic hydroxyl group is protected by an acid-dissociable group (a1-2) is a structural unit containing a group in which a phenolic hydroxyl group is protected by an acid-dissociable group explained in detail below.

<<<<(a1-2-1) Structural Unit Containing a Phenolic Hydroxyl Group>>>>

Examples of the structural unit containing a phenolic hydroxyl group include hydroxystyrenic structural units and structural units in novolac resins, among which preferred are structural units derived from hydroxystyrene or α-methylhydroxystyrene to improve sensitivity. Further, the structural unit containing a phenolic hydroxyl group is also preferably a structural unit represented by formula (a1-20) below to improve sensitivity.

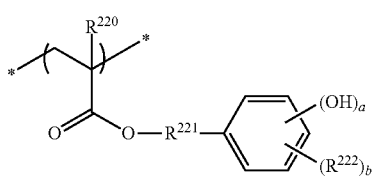

In formula (a1-20), $R^{220}$ represents a hydrogen atom or a methyl group, $R^{221}$ represents a single bond or a divalent linking group, $R^{222}$ represents a halogen atom or a branched-chain alkyl group containing 1 to 5 carbon atoms, a represents an integer of 1 to 5, and b represents an integer of 0 to 4, provided that a+b is 5 or less. When two more $R^{222}$ moieties exist, these $R^{222}$ moieties may be different or the same.

In formula (a1-20) above, $R^{220}$ represents a hydrogen atom or a methyl group, preferably a methyl group.

$R^{221}$ represents a single bond or a divalent linking group. It is preferably a single bond because sensitivity can be improved and the transparency of cured films can also be improved.

Examples of divalent linking groups for $R^{221}$ include alkylene groups, and specific examples of alkylene groups for $R^{221}$ include methylene, ethylene, propylene, isopropylene, n-butylene, isobutylene, tert-butylene, pentylene, isopentylene, neopentylene, hexylene and the like. Among others, $R^{221}$ preferably represents a single bond, a methylene group, or an ethylene group. Further, the divalent linking groups may be substituted by a substituent such as a halogen atom, a hydroxyl group, an alkoxy group or the like. Further, a represents an integer of 1 to 5, preferably a is 1 or 2, more preferably a is 1 because of the advantages of the present invention and easy preparation.

The hydroxyl group is preferably attached to the benzene ring at the 4-position with respect to the carbon atom (the 1-position) attached to $R^{221}$.

$R^{222}$ represents a halogen atom or a branched-chain alkyl group containing 1 to 5 carbon atoms. Specifically, examples include fluorine atom, chlorine atom, bromine atom, methyl, ethyl, propyl, isopropyl, n-butyl, isobutyl, tert-butyl, pentyl, isopentyl, neopentyl and the like. Among others, chlorine atom, bromine atom, methyl or ethyl is preferred because of easy preparation. Further, b represents 0 or an integer of 1 to 4.

<<<<Acid-Decomposable Groups that can be Used in the Structural Unit (a1-2)>>>>

The acid-decomposable groups that can be used in the structural unit containing a group in which a phenolic hydroxyl group is protected by an acid-dissociable group (a1-2) are not specifically limited, and include known ones similarly to the acid-decomposable groups that can be used in the structural unit containing a group in which a carboxyl group is protected by an acid-dissociable group (a1-1). Among the acid-decomposable groups, preferred are those providing a structural unit containing a phenolic hydroxyl group protected as an acetal to improve fundamental properties of the photosensitive resin compositions, especially sensitivity and pattern shape, storage stability of the photosensitive resin compositions, and the ease of forming contact holes. Among the acid-decomposable groups, more preferred are those by which the phenolic hydroxyl group is protected as an acetal represented by formula (a1-10) above to improve sensitivity. It should be noted that when the phenolic hydroxyl group is a phenolic hydroxyl group protected as an acetal represented by formula (a1-10) above, the protected phenolic hydroxyl group as a whole has the structure —Ar—O—$CR^{101}R^{102}(OR^{103})$ wherein Ar represents an arylene group.

A preferred example of an acetal ester structure of the phenolic hydroxyl group is $R^{101}=R^{102}=R^{103}=$methyl or $R^{101}=R^{102}=$methyl in combination with $R^{103}=$benzyl.

Radically polymerizable monomers used for forming the structural unit containing a phenolic hydroxyl group protected as an acetal include, for example, those described in paragraph 0042 of JP-A2011-215590 and the like.

Among them, 4-hydroxyphenyl methacrylate protected by 1-alkoxyalkyl and 4-hydroxyphenyl methacrylate protected by tetrahydropyranyl are preferred to improve transparency.

Specific examples of acetal protecting groups of the phenolic hydroxyl group include 1-alkoxyalkyl groups such as 1-ethoxyethyl, 1-methoxyethyl, 1-n-butoxyethyl, 1-isobutoxyethyl, 1-(2-chloroethoxy)ethyl, 1-(2-ethylhexyloxy)ethyl, 1-n-propoxyethyl, 1-cyclohexyloxyethyl, 1-(2-cyclohexylethoxy)ethyl, 1-benzyloxyethyl and the like, and these can be used alone or as a combination of two or more of them.

Radically polymerizable monomers used for forming the structural unit containing a group in which a phenolic hydroxyl group is protected by an acid-dissociable group (a1-2) may be commercially available or may be synthesized by a known method. For example, they can be synthesized by reacting a compound containing a phenolic hydroxyl group with vinyl ether in the presence of an acid catalyst. Alternatively, they may be synthesized by copolymerizing a monomer containing a phenolic hydroxyl group with another monomer in advance, and then reacting the resulting copolymer with vinyl ether in the presence of an acid catalyst.

Preferred specific examples of the structural unit containing a group in which a phenolic hydroxyl group is protected by an acid-dissociable group (a1-2) include the structural units shown below, but the present invention is not limited to them.

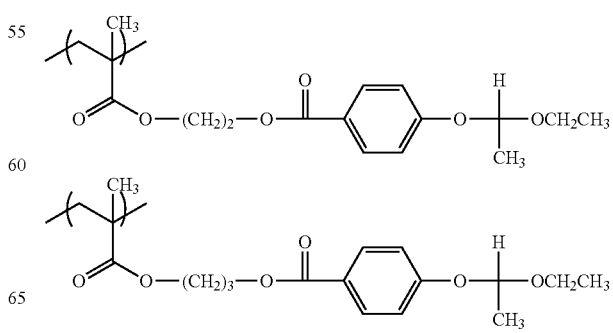

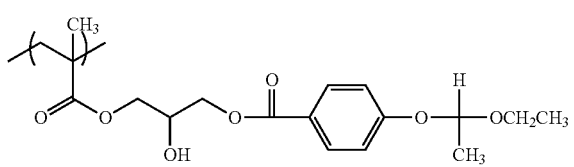
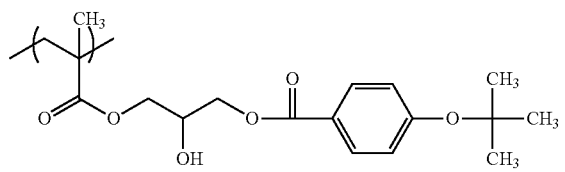
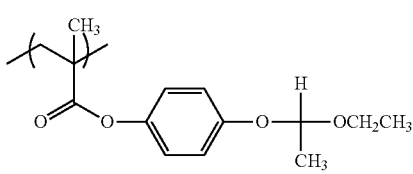
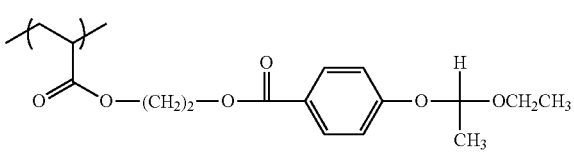
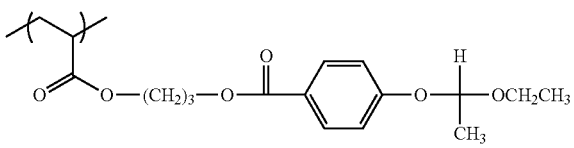
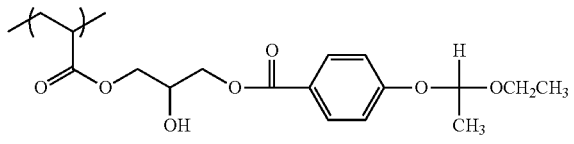
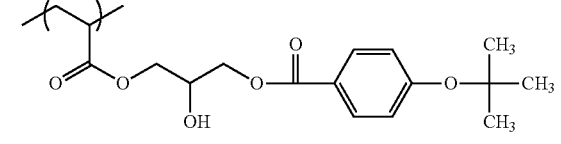
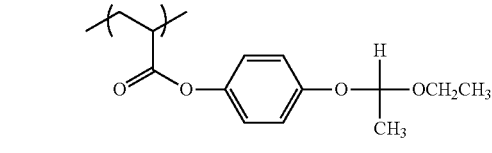
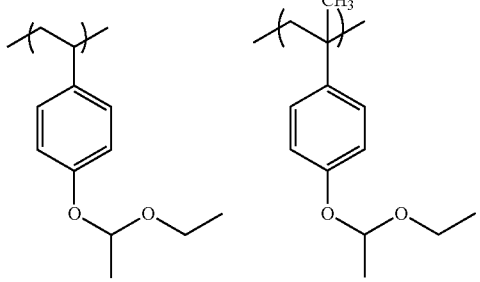

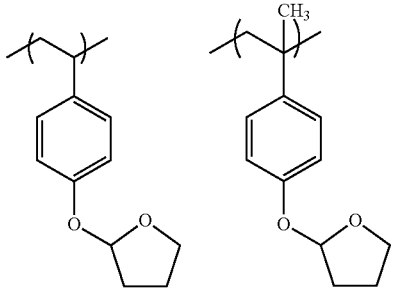

<<<Preferred Embodiments of the Structural Unit (a1)>>>

If a polymer comprising the structural unit (a1) is substantially free from the structural unit (a2), the structural unit (a1) is preferably present at 20 to 100 mol %, more preferably 30 to 90 mol % in the polymer comprising the structural unit (a1).

If a polymer comprising the structural unit (a1) further comprises the structural unit (a2) described below, the structural unit (a1) is preferably present at 3 to 70 mol %, more preferably 10 to 60 mol % in the polymer comprising the structural unit (a1) and the structural unit (a2) to improve sensitivity.

Especially when the acid-decomposable group that can be used in the structural unit (a1) provides a structural unit containing a carboxyl group protected as an acetal, it is preferably present at 20 to 50 mol %.

The structural unit containing a group in which a carboxyl group is protected by an acid-dissociable group (a1-1) is characterized in that it is more rapidly developed as compared with the structural unit containing a group in which a phenolic hydroxyl group is protected by an acid-dissociable group (a1-2).

Therefore, if rapid development is desired, the structural unit containing a group in which a carboxyl group is protected by an acid-dissociable group (a1-1) is preferred. Conversely, if slow development is desired, the structural unit containing a group in which a phenolic hydroxyl group is protected by an acid-dissociable group (a1-2) is preferably used.

The structural unit containing a group in which a carboxyl group is protected by an acid-dissociable group (a1-1) is characterized in that it is more rapidly developed as compared with the structural unit containing a group in which a phenolic hydroxyl group is protected by an acid-dissociable group (a1-2).

Therefore, if rapid development is desired, the structural unit containing a group in which a carboxyl group is protected by an acid-dissociable group (a1-1) is preferred. Conversely, if slow development is desired, the structural unit containing a group in which a phenolic hydroxyl group is protected by an acid-dissociable group (a1-2) is preferably used.

<<(a2) Structural Unit Containing a Crosslinkable Group>>

The component (A) comprises a structural unit containing a crosslinkable group (a2). The crosslinkable group is not specifically limited so far as it is a group that undergoes a curing reaction by heating. A preferred embodiment of the structural unit containing a crosslinkable group includes a structural unit containing at least one member selected from the group consisting of an epoxy group, an oxetanyl group, a group represented by —NH—CH$_2$—O—R (wherein R represents an alkyl group containing 1 to 20 carbon atoms) and an ethylenically unsaturated group, preferably at least one member selected from an epoxy group, an oxetanyl group, and a group represented by —NH—CH$_2$—O—R (wherein R represents an alkyl group containing 1 to 20 carbon atoms).

Especially, the component (A) in the photosensitive resin compositions of the present invention preferably comprises a structural unit containing at least one of an epoxy group and an oxetanyl group. More specifically, it comprises the following.

<<<(a2-1) Structural Unit Containing an Epoxy Group and/or an Oxetanyl Group>>>

The polymer (A) preferably comprises a structural unit containing an epoxy group and/or an oxetanyl group (structural unit (a2-1)).

The 3-membered cyclic ether group described above is also known as epoxy group, and the 4-membered cyclic ether group is also known as oxetanyl group.

The structural unit containing an epoxy group and/or an oxetanyl group (a2-1) may contain at least one epoxy group or oxetanyl group in one structural unit, specifically one or more epoxy groups and one or more oxetanyl groups, or two or more epoxy groups, or two or more oxetanyl groups, preferably, but not specifically limited to, a total of one to three epoxy groups and/or oxetanyl groups, more preferably a total of one or two epoxy groups and/or oxetanyl groups, still more preferably one epoxy group or oxetanyl group.

Specific examples of radically polymerizable monomers used to form the structural unit containing an epoxy group include, for example, glycidyl acrylate, glycidyl methacrylate, α-ethylglycidyl acrylate, α-n-propylglycidyl acrylate, α-n-butylglycidyl acrylate, 3,4-epoxybutyl acrylate, 3,4-epoxybutyl methacrylate, 3,4-epoxycyclohexylmethyl acrylate, 3,4-epoxycyclohexylmethyl methacrylate, α-ethyl-3,4-epoxycyclohexylmethyl acrylate, o-vinylbenzyl glycidyl ether, m-vinylbenzyl glycidyl ether, p-vinylbenzyl glycidyl ether, the compounds containing an alicyclic epoxy skeleton described in paragraphs 0031 to 0035 of Japanese Patent No. 4168443 and the like, the contents of which are incorporated herein by reference.

Specific examples of radically polymerizable monomers used to form the structural unit containing an oxetanyl group include, for example, the (meth)acrylic acid esters containing an oxetanyl group described in paragraphs 0011 to 0016 of JP-A2001-330953 and the like, the contents of which are incorporated herein by reference.

Specific examples of radically polymerizable monomers used to form the structural unit containing an epoxy group and/or an oxetanyl group (a2-1) preferably include monomers containing a methacrylate ester structure and monomers containing an acrylate ester structure.

Among them, the most preferred are glycidyl methacrylate, 3,4-epoxycyclohexylmethyl acrylate, 3,4-epoxycyclohexylmethyl methacrylate, (3-ethyloxetan-3-yl)methyl acrylate, and (3-ethyloxetan-3-yl)methyl methacrylate. These structural units can be used alone or as a combination of two or more of them.

Preferred specific examples of the structural unit containing an epoxy group and/or an oxetanyl group (a2-1) include the structural units shown below, wherein R represents a hydrogen atom or a methyl group.

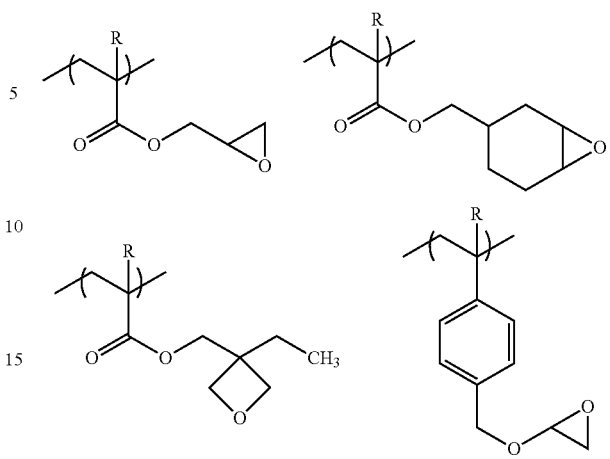

<<<(a2-2) Structural Unit Containing an Ethylenically Unsaturated Group>>>

One example of the structural unit containing a crosslinkable group (a2) is a structural unit containing an ethylenically unsaturated group (a2-2) (hereinafter sometimes referred to as "structural unit (a2-2)"). The structural unit containing an ethylenically unsaturated group (a2-2) is preferably a structural unit containing an ethylenically unsaturated group in the side chain, more preferably a structural unit containing an ethylenically unsaturated group at the end and having a side chain containing 3 to 16 carbon atoms, still more preferably a structural unit having a side chain represented by formula (a2-2-1) below.

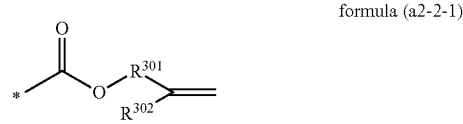

formula (a2-2-1)

In formula (a2-2-1), $R^{301}$ represents a divalent linking group containing 1 to 13 carbon atoms, $R^{302}$ represents a hydrogen atom or a methyl group, and * represents the attachment point of the structural unit containing a crosslinkable group (a2) to the main chain.

$R^{301}$ represents a divalent linking group containing 1 to 13 carbon atoms, which contains an alkenyl group, a cycloalkenyl group, an arylene group or a combination of these groups and may contain a bond such as an ester bond, an ether bond, an amide bond, a urethane bond or the like. Further, the divalent linking group may be substituted at any position by a substituent such as a hydroxyl group, a carboxyl group or the like. Specific examples of $R^{301}$ include the following divalent linking groups.

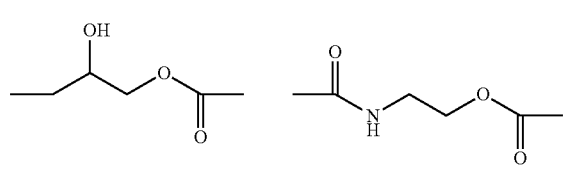

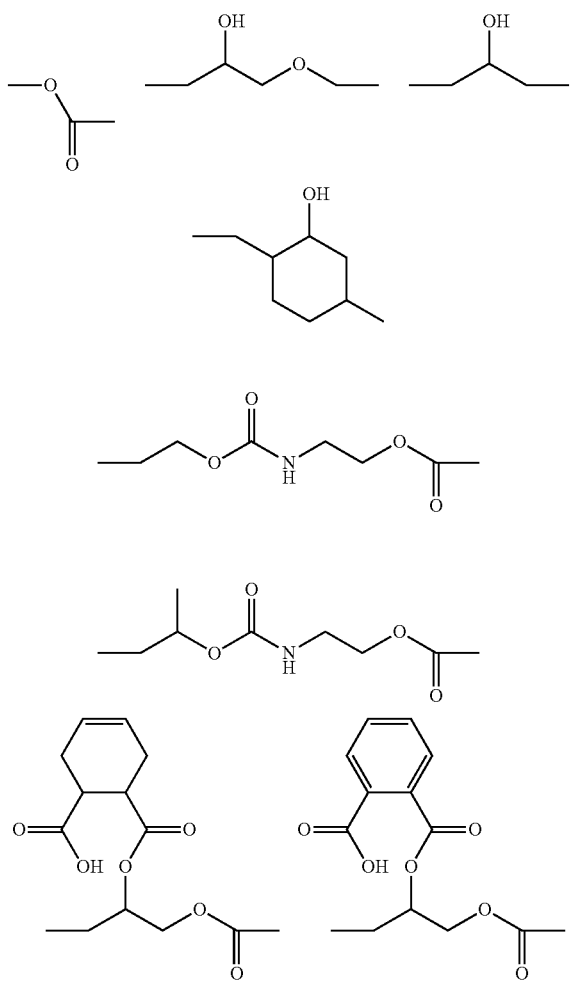

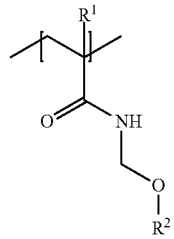

formula (a2-30)

In formula (a2-30), $R^1$ represents a hydrogen atom or a methyl group, and $R^2$ represents an alkyl group containing 1 to 20 carbon atoms.

Preferably, $R^2$ represents an alkyl group containing 1 to 9 carbon atoms, more preferably an alkyl group containing 1 to 4 carbon atoms. Further, the alkyl group may be a straight-chain, branched-chain or cyclic alkyl group, but it is preferably a straight-chain or branched-chain alkyl group.

Specific examples of $R^2$ include methyl, ethyl, n-butyl, i-butyl, cyclohexyl, and n-hexyl. Among others, i-butyl, n-butyl and methyl are preferred.

<<<Preferred Embodiments of the Structural Unit (a2)>>>

If a polymer comprising the structural unit (a2) is substantially free from the structural unit (a1), the structural unit (a2) is preferably present at 5 to 90 mol %, more preferably 20 to 80 mol % in the polymer comprising the structural unit (a2).

If a polymer comprising the structural unit (a2) further comprises the structural unit (a1), the structural unit (a2) is preferably present at 3 to 70 mol %, more preferably 10 to 60 mol % in the polymer comprising the structural unit (a1) and the structural unit (a2) to improve chemical resistance.

In the present invention, any embodiment preferably comprises the structural unit (a2) at 3 to 70 mol %, more preferably 10 to 60 mol % among all of the structural units of the component (A).

When the proportion is in the numerical ranges defined above, cured films obtained from the photosensitive resin compositions have improved transparency and chemical resistance.

<<(a3) Additional Structural Units>>

In the present invention, the component (A) may comprise additional structural units (a3) other than the structural unit (a1) and/or (a2) in addition to these units. The polymer component (1) and/or (2) may comprise these additional structural units. Alternatively, a polymer component substantially free from (a1) and (a2) and comprising additional structural units (a3) may be contained in addition to the polymer component (1) or (2). When a polymer component substantially free from (a1) and (a2) and comprising additional structural units (a3) is contained in addition to the polymer component (1) or (2), such polymer component is preferably contained in amount of 60% by mass or less, more preferably 40% by mass or less, still more preferably 20% by mass or less among all of the polymer components.

Monomers forming the additional structural units (a3) are not specifically limited, and include, for example, styrenes, (meth)acrylic acid alkyl esters, (meth)acrylic acid cyclic alkyl esters, (meth)acrylic acid aryl esters, unsaturated dicarboxylic acid diesters, unsaturated bicyclic compounds, maleimide compounds, unsaturated aromatic compounds, conjugated diene compounds, unsaturated monocarboxylic acids, unsaturated dicarboxylic acids, unsaturated dicarboxylic anhydrides, and other unsaturated compounds. Further, structural units containing an acid group may be contained as described later.

Among the side chains represented by formula (a2-2-1) above, aliphatic side chains including the divalent linking groups represented by $R^{301}$ are preferred.

Description about other structural units containing an ethylenically unsaturated group (a2-2) can be found in paragraphs 0072 to 0090 of JP-A2011-215580, the contents of which are incorporated herein by reference.

<<<(a2-3) Structural Unit Containing a Group Represented by —NH—CH$_2$—O—R Wherein R Represents an Alkyl Group Containing 1 to 20 Carbon Atoms>>>

The polymer used in the present invention also preferably comprises a structural unit containing a group represented by —NH—CH$_2$—O—R wherein R represents an alkyl group containing 1 to 20 carbon atoms (a2-3). When the structural unit (a2-3) is contained, a curing reaction can be induced by mild heating so that cured films having various excellent properties can be obtained. Preferably, R represents an alkyl group containing 1 to 9 carbon atoms, more preferably an alkyl group containing 1 to 4 carbon atoms. Further, the alkyl group may be a straight-chain, branched-chain or cyclic alkyl group, but it is preferably a straight-chain or branched-chain alkyl group. The structural unit (a2) is more preferably a structural unit containing a group represented by formula (a2-30) below:

The monomers forming the additional structural units (a3) can be used alone or as a combination of two or more of them.

Preferred embodiments of polymer components of the present invention are shown below, but the present invention is not limited to them.

(First Embodiment)

An embodiment wherein the polymer component (1) further comprises one or more additional structural units (a3).

(Second Embodiment)

An embodiment wherein the polymer comprising the structural unit containing a group in which an acid group is protected by an acid-dissociable group (a1) of the polymer component (2) further comprises one or more additional structural units (a3).

(Third Embodiment)

An embodiment wherein the polymer comprising the structural unit containing a crosslinkable group (a2) of the polymer component (2) further comprises one or more additional structural units (a3).

(Fourth Embodiment)

An embodiment according to any one of the first to third embodiments, wherein the additional structural units (a3) include a structural unit containing at least an acid group.

(Fifth Embodiment)

An embodiment comprising a polymer which is substantially free from (a1) and (a2) and comprises additional structural units (a3) in addition to the polymer component (1) or (2).

(Sixth Embodiment)

An embodiment comprising a combination of two or more of the first to fifth embodiments.

(Seventh Embodiment)

An embodiment comprising at least the polymer component (2), especially an embodiment according to any one of the first to sixth embodiments comprising at least the polymer component (2)

The structural units (a3) specifically include structural units consisting of styrene, tert-butoxystyrene, methylstyrene, hydroxystyrene, α-methylstyrene, acetoxystyrene, methoxystyrene, ethoxystyrene, chlorostyrene, methyl vinylbenzoate, ethyl vinylbenzoate, 4-hydroxybenzoic acid (3-methacryloyloxypropyl)ester, (meth)acrylic acid, methyl (meth)acrylate, ethyl(meth)acrylate, n-propyl(meth)acrylate, isopropyl(meth)acrylate, 2-hydroxyethyl(meth)acrylate, 2-hydroxypropyl(meth)acrylate, benzyl(meth)acrylate, isobornyl(meth)acrylate, acrylonitrile, ethylene glycol monoacetoacetate mono(meth)acrylate and the like. In addition, the compounds described in paragraphs 0021 to 0024 of JP-A2004-264623 are also included.

Further, the additional structural units (a3) are preferably styrenes and groups having an alicyclic skeleton to improve electrical properties. Specifically, examples include styrene, tert-butoxystyrene, methylstyrene, hydroxystyrene, α-methylstyrene, dicyclopentanyl(meth)acrylate, cyclohexyl(meth)acrylate, isobornyl(meth)acrylate, benzyl(meth)acrylate and the like.

Furthermore, the additional structural units (a3) are preferably (meth)acrylic acid alkyl esters to improve adhesion. Specifically, examples include methyl(meth)acrylate, ethyl (meth)acrylate, propyl(meth)acrylate, n-butyl(meth)acrylate and the like, more preferably methyl(meth)acrylate. Among the structural units constituting the polymer (A), the content of the structural units (a3) is preferably 60 mol % or less, more preferably 50 mol % or less, still more preferably 40 mol % or less.

The lower limit may be 0 mol %, or for example, 1 mol % or more, or even 5 mol % or more. When it is within the numerical ranges defined above, various properties of cured films obtained from the photosensitive resin compositions are improved.

The additional structural units (a3) preferably contain an acid group. When they contain an acid group, they are more soluble in alkaline developers so that the advantages of the present invention are more effectively produced. As used herein, the "acid group" refers to a proton-dissociating group having a pKa of less than 7. The acid group is typically incorporated into a polymer as a structural unit containing the acid group by using a monomer capable of forming the acid group. When the polymer comprises a structural unit containing such an acid group, it tends to be more soluble in alkaline developers.

Examples of acid groups used in the present invention include those derived from carboxylic acid groups, those derived from sulfonamide group, those derived from phosphonic acid groups, those derived from sulfonic acid groups, those derived from phenolic hydroxyl groups, sulfonamide groups, sulfonyl imide groups and the like, preferably those derived from carboxylic acid groups and/or those derived from phenolic hydroxyl groups.

More preferably, the structural unit containing an acid group used in the present invention is a structural unit derived from styrene, or a structural unit derived from a vinyl compound, or a structural unit derived from (meth)acrylic acid and/or an ester thereof.

In the present invention, a structural unit containing a carboxyl group or a structural unit containing a phenolic hydroxyl group is especially preferably contained to improve sensitivity.

The structural unit containing an acid group is preferably present at 1 to 80 mol %, more preferably 1 to 50 mol %, still more preferably 5 to 40 mol %, especially preferably 5 to 30 mol %, most preferably 5 to 20 mol % of the structural units of all of the polymer components.

In the present invention, a polymer substantially free from (a1) and (a2) and comprising additional structural units (a3) may be contained in addition to the polymer component (1) or (2).

Such a polymer is preferably a resin containing a carboxyl group in the side chain. For example, preferred examples include methacrylic acid copolymers, acrylic acid copolymers, itaconic acid copolymers, crotonic acid copolymers, maleic acid copolymers, partially esterified maleic acid copolymers and the like, as well as acidic cellulose derivatives containing a carboxyl group in the side chain, adducts of polymers containing a hydroxyl group with an acid anhydride and the like, and high molecular polymers containing a (meth)acryloyl group in the side chain as described in JP-A-S59-44615, JP-B-S54-34327, JP-B-S58-12577, JP-B-S54-25957, JP-A-S59-53836, and JP-A-S59-71048.

For example, they include benzyl(meth)acrylate/(meth) acrylic acid copolymers, 2-hydroxyethyl(meth)acrylate/benzyl(meth)acrylate/(meth)acrylic acid copolymers; and the 2-hydroxypropyl(meth)acrylate/polystyrene macromonomer/benzyl methacrylate/methacrylic acid copolymers, 2-hydroxy-3-phenoxypropyl acrylate/polymethyl methacrylate macromonomer/benzyl methacrylate/methacrylic acid copolymers, 2-hydroxyethyl methacrylate/polystyrene macromonomer/methyl methacrylate/methacrylic acid copolymers, and 2-hydroxyethyl methacrylate/polystyrene macromonomer/benzyl methacrylate/methacrylic acid copolymers described in JP-A-H7-140654; and the like.

Other examples that can be used include the known high molecular compounds described in JP-A-H7-207211, JP-A-H8-259876, JP-A-H10-300922, JP-A-H11-140144, JP-A-

H11-174224, JP-A2000-56118, JP-A2003-233179, JP-A2009-52020 and the like, the contents of which are incorporated herein by reference.

Only one or more than one of these polymers may be contained.

These polymers are also commercially available, such as SMA 1000P, SMA 2000P, SMA 3000P, SMA 1440F, SMA 17352P, SMA 2625P and SMA 3840F (all from Sartomer); ARUFON UC-3000, ARUFON UC-3510, ARUFON UC-3900, ARUFON UC-3910, ARUFON UC-3920 and ARUFON UC-3080 (all from Toagosei Co., Ltd.); Joncryl 690, Joncryl 678, Joncryl 67 and Joncryl 586(all from BASF); and the like.

<<Molecular Weight of the Polymer (A)>>

The polymer (A) preferably has a molecular weight in the range of 1,000 to 200,000, more preferably 2,000 to 50,000 expressed as a polystyrene equivalent weight average molecular weight. When it is in the numerical ranges defined above, various properties are improved. The ratio between the number average molecular weight and the weight average molecular weight (dispersity) is preferably 1.0 to 5.0, more preferably 1.5 to 3.5.

<<Processes for Preparing the Polymer (A)>>

According to one example of various known processes for synthesizing the component (A), it can be synthesized by polymerizing a radically polymerizable monomer mixture comprising radically polymerizable monomers used for forming at least structural units represented by (a1) and (a3) above in an organic solvent using a radical polymerization initiator.

Alternatively, it can also be synthesized by a so-called polymer reaction.

The photosensitive resin compositions of the present invention preferably comprise the component (A) in a proportion of 50 to 99.9 parts by mass, more preferably 70 to 98 parts by mass per 100 parts by mass of the total solids.

<(B) Compound Represented by Formula (I)>

The photosensitive resin compositions of the present invention comprise (B) a compound represented by formula (I), and the compound (B) represented by formula (I) serves as a photoacid generator.

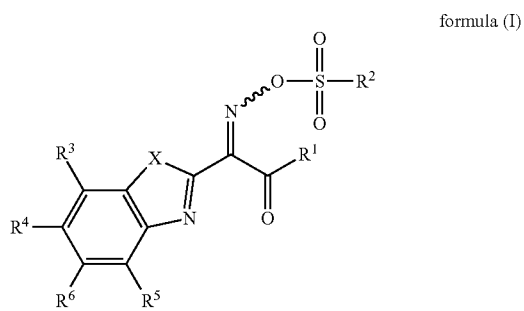

formula (I)

In formula (I), $R^1$ represents an alkyl group or an aryl group, $R^2$ represents an alkyl group, an aryl group or a heteroaryl group. $R^3$ to $R^6$ each represent a hydrogen atom, an alkyl group, an aryl group or a halogen atom. Alternatively, $R^3$ and $R^4$, $R^4$ and $R^5$, or $R^5$ and $R^6$ may be taken together to form an alicyclic ring or an aromatic ring. X represents —O— or —S—.

$R^1$ represents an alkyl group or an aryl group. The alkyl group is preferably an alkyl group having a branched-chain structure or an alkyl group having a cyclic structure. Preferably, the alkyl group contains 3 to 10 carbon atoms. Especially, the alkyl group preferably contains 3 to 6 carbon atoms when it has a branched-chain structure, or the alkyl group preferably contains 5 to 7 carbon atoms when it has a cyclic structure.

Alkyl groups include, for example, propyl, isopropyl, n-butyl, s-butyl, isobutyl, tert-butyl, pentyl, isopentyl, neopentyl, 1,1-dimethylpropyl, hexyl, 2-ethylhexyl, cyclohexyl, cyclopentyl, octyl and the like, preferably isopropyl, tert-butyl, neopentyl, and cyclohexyl.

Preferably, the aryl group contains 6 to 12 carbon atoms, more preferably 6 to 8 carbon atoms, still more preferably 6 to 7 carbon atoms. Such aryl groups include phenyl, naphthyl and the like, preferably phenyl.

The alkyl group and aryl group represented by $R^1$ may be substituted by a substituent. The substituent may be, for example, a halogen atom (fluorine atom, chlorine atom, bromine atom, iodine atom), a straight-chain, branched-chain or cyclic alkyl group (e.g., methyl, ethyl, propyl and the like), alkenyl, alkynyl, aryl, acyl, alkoxycarbonyl, aryloxycarbonyl, carbamoyl, cyano, carboxyl, hydroxyl, alkoxy, aryloxy, alkylthio, arylthio, heterocyclyloxy, acyloxy, amino, nitro, hydrazino, heterocyclyl or the like. The substituent may be further substituted by these groups.

Preferred are halogen atoms and methyl.

In the photosensitive resin compositions of the present invention, $R^1$ preferably represents an alkyl group to improve transparency, or $R^1$ preferably represents a branched-chain alkyl group containing 3 to 6 carbon atoms, a cyclic alkyl group containing 5 to 7 carbon atoms, or a phenyl group, more preferably a branched-chain alkyl group containing 3 to 6 carbon atoms, or a cyclic alkyl group containing 5 to 7 carbon atoms to improve both storage stability and sensitivity. By employing such a bulky group (especially a bulky alkyl group) for $R^1$, transparency can be further improved.

Among bulky substituents, preferred are isopropyl, tert-butyl, neopentyl, and cyclohexyl, more preferably tert-butyl, and cyclohexyl.

$R^2$ represents an alkyl group, an aryl group or a heteroaryl group. The alkyl group represented by $R^2$ is preferably a straight-chain, branched-chain or cyclic alkyl group containing 1 to 10 carbon atoms. The alkyl group may be, for example, methyl, ethyl, propyl, isopropyl, n-butyl, tert-butyl, pentyl, neopentyl, hexyl, cyclohexyl or the like, preferably methyl.

The aryl group is preferably an aryl group containing 6 to 10 carbon atoms. The aryl group may be phenyl, naphthyl, p-toluoyl(p-methylphenyl) or the like, preferably phenyl or p-toluoyl.

The heteroaryl group may be, for example, pyrrole, indole, carbazole, furan, thiophene or the like.

The alkyl group, aryl group, and heteroaryl group represented by $R^2$ may be substituted by a substituent. The substituent is as defined for the substituent by which the alkyl group and aryl group represented by $R^1$ may be substituted.

Preferably, $R^2$ represents an alkyl group or an aryl group, more preferably an aryl group, still more preferably a phenyl group.

The substituent on the phenyl group is preferably methyl.

$R^3$ to $R^6$ each represent a hydrogen atom, an alkyl group, an aryl group or a halogen atom (fluorine atom, chlorine atom, bromine atom, iodine atom). The alkyl group represented by $R^3$ to $R^6$ is as defined for the alkyl group represented by $R^2$, and also covers similar preferred ranges. Further, the aryl group represented by $R^3$ to $R^6$ is as defined for the aryl group represented by $R^1$, and also covers similar preferred ranges.

Among $R^3$ to $R^6$, $R^3$ and $R^4$, $R^4$ and $R^5$, or $R^5$ and $R^6$ may be taken together to form a ring, preferably an alicyclic ring or an aromatic ring, more preferably a benzene ring.

Preferably, $R^3$ to $R^6$ represent a hydrogen atom, an alkyl group, or a halogen atom (fluorine atom, chlorine atom, bromine atom), or $R^3$ and $R^4$, $R^4$ and $R^5$, or $R^5$ and $R^6$ are taken together to form a benzene ring, more preferably they represent a hydrogen atom, a methyl group, a fluorine atom, a chlorine atom, or a bromine atom, or $R^3$ and $R^4$, $R^4$ and $R^5$, or $R^5$ and $R^6$ are taken together to form a benzene ring.

Preferred embodiments of $R^3$ to $R^6$ are as follows.

(Embodiment 1)

At least one represents a hydrogen atom, preferably at least two represent a hydrogen atom.

(Embodiment 2)

The total number of alkyl groups, aryl groups, or halogen atoms is three or less, preferably one or less.

(Embodiment 3)

$R^3$ and $R^4$, $R^4$ and $R^5$, or $R^5$ and $R^6$ are taken together to form a benzene ring.

(Embodiment 4)

An embodiment satisfying the embodiments 1 and 2 and/or an embodiment satisfying the embodiments 1 and 3.

X represents —O— or —S—.

Specific examples of formula (I) above include the compounds shown below, but the present invention is not specifically limited to them. It should be noted that in the exemplary compounds, Ts represents tosyl(p-toluenesulfonyl), Me represents methyl, Bu represents n-butyl, and Ph represents phenyl.

B-1

B-2

B-3

B-4

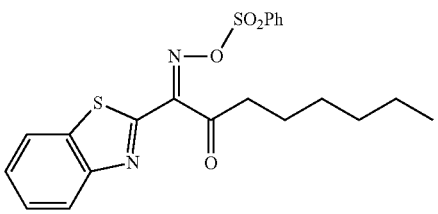

B-5

B-6

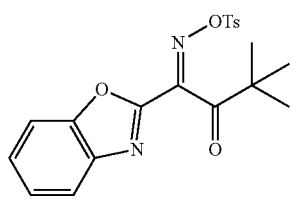

B-7

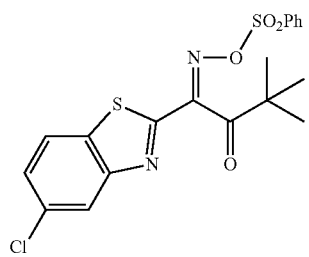

B-8

B-9

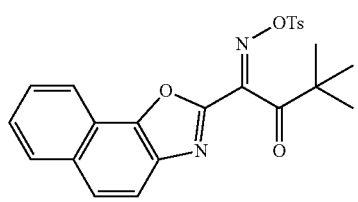

B-10

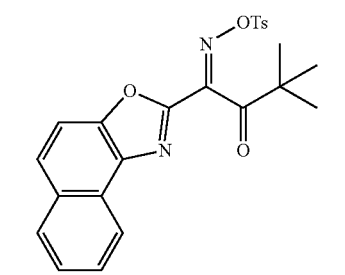

B-11

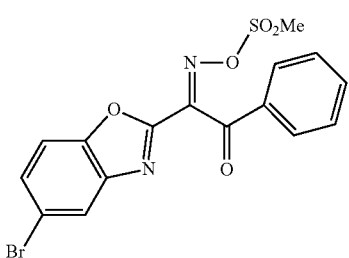

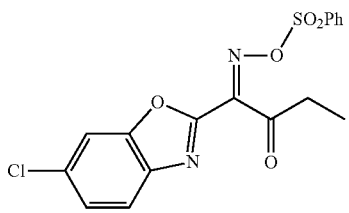

-continued
B-12
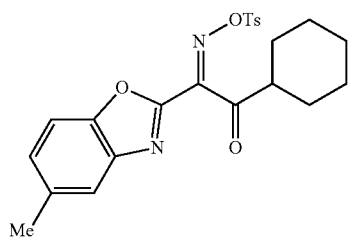
B-13
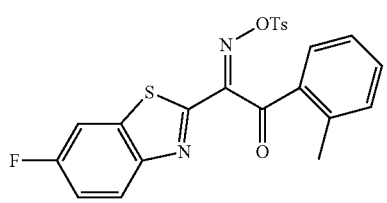
B-14
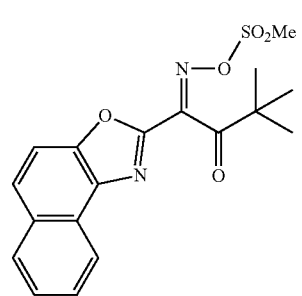
B-15
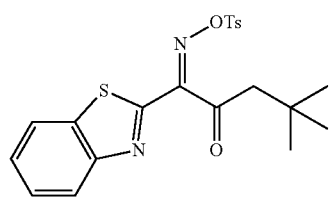
B-16
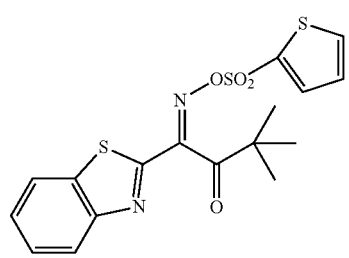
B-17
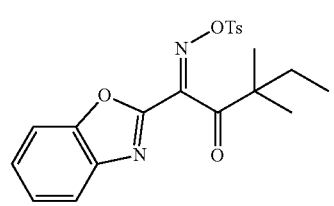
B-18
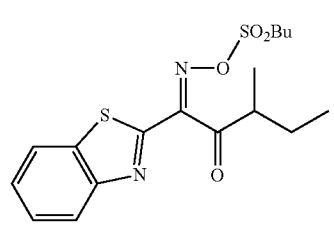
-continued
B-19
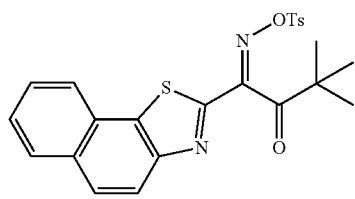
B-20
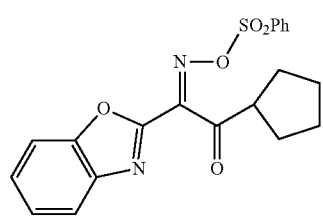
B-21
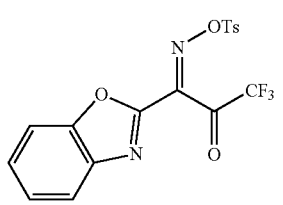
B-22
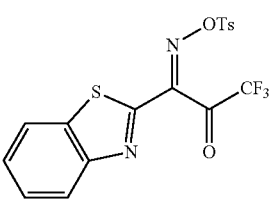
B-23
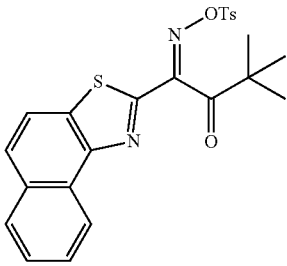
B-24
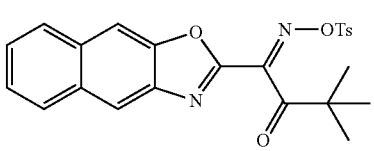
B-25
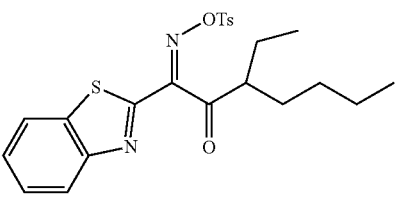

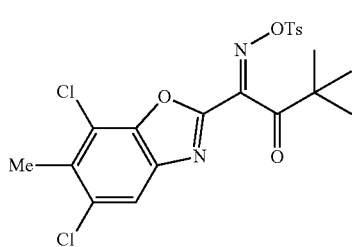
B-26

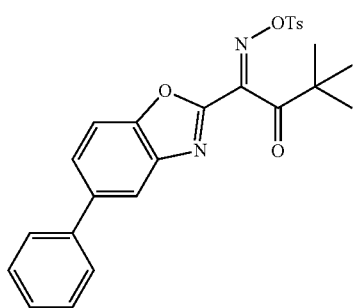
B-27

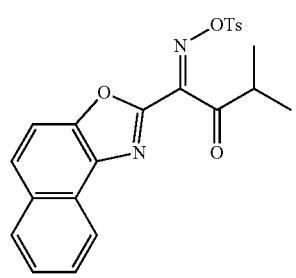
B-28

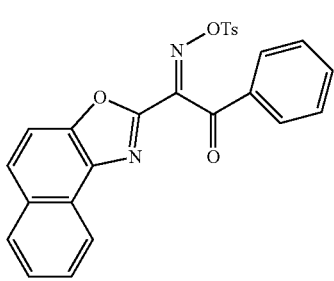
B-29

In the photosensitive resin compositions of the present invention, the compound (B) represented by formula (I) is preferably used in an amount of 0.1 to 10 parts by mass, more preferably 0.5 to 5 parts by mass per 100 parts by mass of the total resin components (preferably the total solids, more preferably the total of the polymers) in the photosensitive resin compositions. Two or more compounds can be used in combination. In the present invention, other acid generators may be contained.

<(C) Solvent>

The photosensitive resin compositions of the present invention comprise a solvent (C). The photosensitive resin compositions of the present invention are preferably prepared as a solution of essential components of the present invention and optional components as described later dissolved in a solvent (C).

Solvents (C) that can be used in the photosensitive resin compositions of the present invention include known solvents such as ethylene glycol monoalkyl ethers, ethylene glycol dialkyl ethers, ethylene glycol monoalkyl ether acetates, propylene glycol monoalkyl ethers, propylene glycol dialkyl ethers, propylene glycol monoalkyl ether acetates, diethylene glycol dialkyl ethers, diethylene glycol monoalkyl ether acetates, dipropylene glycol monoalkyl ethers, dipropylene glycol dialkyl ethers, dipropylene glycol monoalkyl ether acetates, esters, ketones, amides, lactones and the like. Further, specific examples of the solvent (D) used in the photosensitive resin compositions of the present invention include the solvents described in paragraphs 0174 to 0178 of JP-A2011-221494, the contents of which are incorporated herein by reference.

In addition to these solvents, other solvents can be added as appropriate, such as benzyl ethyl ether, dihexyl ether, ethylene glycol monophenyl ether acetate, diethylene glycol monomethyl ether, diethylene glycol monoethyl ether, isophorone, capronic acid, caprylic acid, 1-octanol, 1-nonanol, benzyl alcohol, anisole, benzyl acetate, ethyl benzoate, diethyl oxalate, diethyl maleate, ethylene carbonate, propylene carbonate and the like. These solvents can be used alone or as a mixture of two or more of them. The solvents that can be used in the present invention are preferably used alone or as a combination of two of them, more preferably as a combination of two of them, still more preferably as a combination of a propylene glycol monoalkyl ether acetate or dialkyl ether or diacetate and a diethylene glycol dialkyl ether, or a combination of an ester and a butylene glycol alkyl ether acetate.

Further, the component C is preferably a solvent having a boiling point of 130° C. or more and less than 160° C., or a solvent having a boiling point of 160° C. or more, or a mixture thereof. Examples of solvents having a boiling point of 130° C. or more and less than 160° C. include propylene glycol monomethyl ether acetate (b.p. 146° C.), propylene glycol monoethyl ether acetate (b.p. 158° C.), propylene glycol methyl-n-butyl ether (b.p. 155° C.), and propylene glycol methyl-n-propyl ether (b.p. 131° C.).

Examples of solvents having a boiling point of 160° C. or more include ethyl 3-ethoxyproionate (b.p. 170° C.), diethylene glycol methyl ethyl ether (b.p. 176° C.), propylene glycol monomethyl ether propionate (b.p. 160° C.), dipropylene glycol methyl ether acetate (b.p. 213° C.), 3-methoxybutyl ether acetate (b.p. 171° C.), diethylene glycol diethyl ether (b.p. 189° C.), diethylene glycol dimethyl ether (b.p. 162° C.), propylene glycol diacetate (b.p. 190° C.), diethylene glycol monoethyl ether acetate (b.p. 220° C.), dipropylene glycol dimethyl ether (b.p. 175° C.), and 1,3-butylene glycol diacetate (b.p. 232° C.).

Preferably, the photosensitive resin compositions of the present invention comprise the solvent (C) in an amount of 50 to 95 parts by mass, more preferably 60 to 90 parts by mass per 100 parts by mass of the total resin components in the photosensitive resin compositions.

<Other Components>

In addition to the components described above, the photosensitive resin compositions of the present invention can also preferably comprise (D) an alkoxysilane compound, (E) a crosslinking agent, (F) a sensitizer, (G) a basic compound, (H) a surfactant, and (I) an antioxidant, as appropriate. In addition, the photosensitive resin compositions of the present invention can also comprise known additives such as acid amplifiers, accelerators, plasticizers, heat-induced free radical generators, thermal acid generators, UV absorbers, thickeners, and organic or inorganic suspending agents.

(D) Alkoxysilane Compound

The photosensitive resin compositions of the present invention are characterized in that they comprise (D) an alkoxysilane compound (also referred to as "component (D)"). When an alkoxysilane compound is used, the adhesion of films formed from the photosensitive resin compositions of the present invention to substrates can be improved or the properties of films formed from the photosensitive resin compositions of the present invention can be optimized. The alkoxysilane compound is preferably a dialkoxysilane compound or a trialkoxysilane compound, more preferably a trialkoxysilane compound. Preferably, the alkoxy group of the alkoxysilane compound contains 1 to 5 carbon atoms.

The alkoxysilane compound (D) that can be used in the photosensitive resin compositions of the present invention is preferably a compound that improves adhesion of insulating layers to inorganic materials constituting substrates including, for example, silicon compounds such as silicon, silicon oxide, silicon nitride and the like; and metals such as gold, copper, molybdenum, titanium, aluminum and the like. Specifically, known silane coupling agents and the like are also suitable.

Silane coupling agents include, for example, γ-aminopropyltrimethoxysilane, γ-aminopropyltriethoxysilane, γ-glycidoxypropyltrialkoxysilane, γ-glycidoxypropylalkyldialkoxysilane, γ-methacryloxypropyltrialkoxysilane, γ-methacryloxypropylalkyldialkoxysilane, γ-chloropropyltrialkoxysilane, γ-mercaptopropyltrialkoxysilane, β-(3,4-epoxycyclohexyl)ethyltrialkoxysilane, and vinyltrialkoxysilane. Among them, γ-glycidoxypropyltrialkoxysilane and γ-methacryloxypropyltrialkoxysilane are more preferred, still more preferably γ-glycidoxypropyltrialkoxysilane, even more preferably 3-glycidoxypropyltrimethoxysilane. These can be used alone or as a combination of two or more of them.

The following compounds can also preferably be employed.

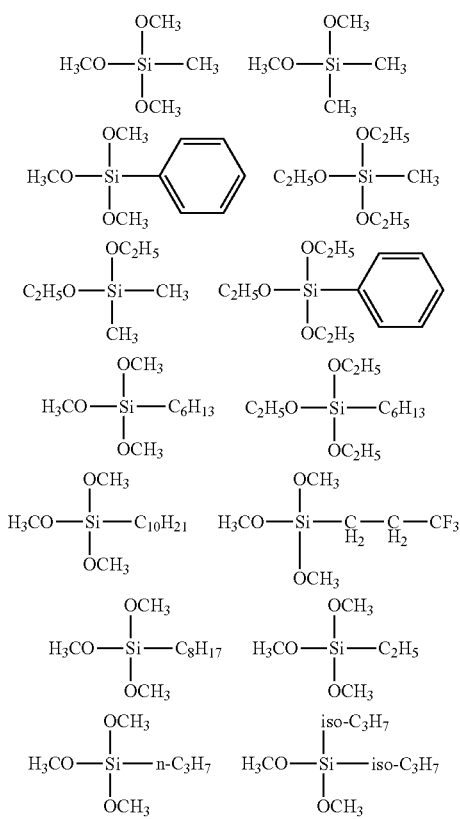

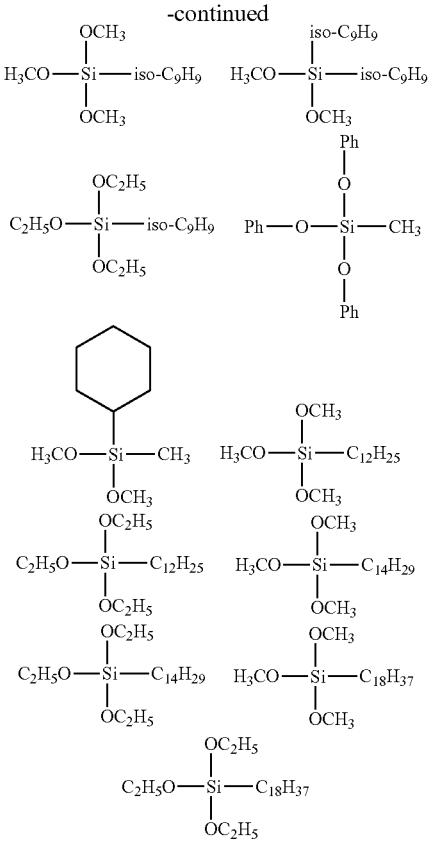

In the compounds shown above, Ph represents a phenyl group.

The alkoxysilane compound (D) in the photosensitive resin compositions of the present invention is not specifically limited to these compounds, and known ones can be used. Preferably, the photosensitive resin compositions of the present invention comprise the alkoxysilane compound (D) in an amount of 0.1 to 30 parts by mass, more preferably 0.5 to 20 parts by mass per 100 parts by mass of the total solids in the photosensitive compositions.

(E) Crosslinking Agent

The photosensitive resin compositions of the present invention preferably comprise a crosslinking agent, as appropriate. When a crosslinking agent is added, stronger cured films can be obtained from the photosensitive resin compositions of the present invention.

The crosslinking agent is not limited so far as it induces a crosslinking reaction by heat (except for the component A). For example, the compounds described below can be added, such as compounds containing two or more epoxy groups or oxetanyl groups in the molecule, or alkoxymethyl-containing crosslinking agents, or compounds containing at least one ethylenically unsaturated double bond, or blocked isocyanate compounds or the like.

Preferably, the crosslinking agent is added to the photosensitive resin compositions of the present invention in amount of 0.01 to 50 parts by mass, more preferably 0.1 to 30 parts by mass, still more preferably 0.5 to 20 parts by mass per 100 parts by mass of the total solids of the photosensitive resin compositions.

When it is added in the ranges defined above, cured films having high mechanical strength and solvent resistance can be obtained.

Two or more crosslinking agents can also be used in combination, in which case the total amount of the crosslinking agents should be in the ranges defined above.

<Compounds Containing Two or More Epoxy Groups or Oxetanyl Groups in the Molecule>

Specific examples of compounds containing two or more epoxy groups in the molecule include bisphenol A epoxy resins, bisphenol F epoxy resins, phenol novolac epoxy resins, cresol novolac epoxy resins, aliphatic epoxy resins and the like.

These are commercially available. For example, they include the commercially available products described in paragraph 0189 of JP-A2011-221494 such as JER157S70 and JER157S65 (from Mitsubishi Chemical Holdings Corporation) and the like. Other examples include ADEKA RESIN series EP-4000S, EP-4003S, EP-4010S and EP-4011S (all from ADEKA CORPORATION); NC-2000, NC-3000, NC-7300, XD-1000, EPPN-501 and EPPN-502 (all from ADEKA CORPORATION); Denacol EX-611, EX-612, EX-614, EX-614B, EX-622, EX-512, EX-521, EX-411, EX-421, EX-313, EX-314, EX-321, EX-211, EX-212, EX-810, EX-811, EX-850, EX-851, EX-821, EX-830, EX-832, EX-841, EX-911, EX-941, EX-920, EX-931, EX-212L, EX-214L, EX-216L, EX-321L, EX-850L, DLC-201, DLC-203, DLC-204, DLC-205, DLC-206, DLC-301 and DLC-402 (all from Nagase ChemteX Corporation); YH-300, YH-301, YH-302, YH-315, YH-324 and YH-325 (all from the new Nippon Steel Chemical Co., Ltd.); CELLOXIDE 2021P, 2081, 3000, EHPE3150, EPOLEAD GT400, CELVENUS B0134 and B0177 (Daicel Corporation); and the like.

These can be used alone or as a combination of two or more of them.

Among them, more preferred are bisphenol A epoxy resins, bisphenol F epoxy resins, phenol novolac epoxy resins and aliphatic epoxy resins, among which bisphenol A epoxy resins are especially preferred.

Specific examples of compounds containing two or more oxetanyl groups in the molecule that can be used include ARON OXETANE OXT-121, OXT-221, OX-SQ and PNOX (all from Toagosei Co., Ltd.).

Further, the compounds containing an oxetanyl group are preferably used alone or as a mixture with an epoxy-containing compound.

Further, other crosslinking agents that can be preferably used include the alkoxymethyl-containing crosslinking agents and the compounds containing at least one ethylenically unsaturated double bond described in paragraphs 0107 to 0108 of JP-A2012-8223 and the like, the contents of which are incorporated herein by reference. The alkoxymethyl-containing crosslinking agents preferably include alkoxymethylated glycoluril.

<Blocked Isocyanate Compounds>

In the photosensitive resin compositions of the present invention, blocked isocyanate compounds can also be preferably employed as crosslinking agents. The blocked isocyanate compounds are not specifically limited so far as they are compounds containing a blocked isocyanate group, but preferably compounds containing two or more blocked isocyanate groups in one molecule to improve curability.

As used herein, the "blocked isocyanate group" refers to a group capable of generating an isocyanate group by heat, and preferably includes, for example, a group containing an isocyanate group protected by reaction with a blocking agent. Preferably, the blocked isocyanate group is a group capable of generating an isocyanate group by heating at 90° C. to 250° C.

The blocked isocyanate compounds may have any skeleton containing two isocyanate groups in one molecule without any specific limitation, and may be aliphatic, alicyclic or aromatic polyisocyanates, and examples that can be conveniently used include, for example, isocyanate compounds such as 2,4-tolylene diisocyanate, 2,6-tolylene diisocyanate, isophorone diisocyanate, 1,6-hexamethylene diisocyanate, 1,3-trimethylene diisocyanate, 1,4-tetramethylene diisocyanate, 2,2,4-trimethylhexamethylene diisocyanate, 2,4,4-trimethylhexamethylene diisocyanate, 1,9-nonamethylene diisocyanate, 1,10-decamethylene diisocyanate, 1,4-cyclohexane diisocyanate, 2,2'-diethyl ether diisocyanate, 4,4'-diphenylmethane diisocyanate, o-xylene diisocyanate, m-xylene diisocyanate, p-xylene diisocyanate, methylene bis(cyclohexyl isocyanate), 1,3-dimethylenecyclohexane diisocyanate, 1,4-dimethylenecyclohexane diisocyanate, 1,5-naphthalene diisocyanate, p-phenylene diisocyanate, 3,3'-methylene ditolylene-4,4'-diisocyanate, 4,4'-diphenyl ether diisocyanate, tetrachlorophenylene diisocyanate, norbornane diisocyanate, hydrogenated 1,3-xylylene diisocyanate, hydrogenated 1,4-xylylene diisocyanate and the like; and compounds having a prepolymer skeleton derived from these compounds. Among them, tolylene diisocyanate (TDI), diphenylmethane diisocyanate (MDI), hexamethylene diisocyanate (HDI), and isophorone diisocyanate (IPDI) are especially preferred.

Parent structures of the blocked isocyanate compounds in the photosensitive resin compositions of the present invention include biurets, isocyanurates, adducts, difunctional prepolymers and the like.

Blocking agents forming blocked structures of the blocked isocyanate compounds include oxime compounds, lactam compounds, phenol compounds, alcohol compounds, amine compounds, active methylene compounds, pyrazole compounds, mercaptan compounds, imidazole compounds, imide compounds and the like. Among them, blocking agents selected from oxime compounds, lactam compounds, phenol compounds, alcohol compounds, amine compounds, active methylene compounds, and pyrazole compounds are especially preferred.

The oxime compounds include oximes and ketoximes, examples of which specifically include acetoxime, formaldoxime, cyclohexane oxime, methyl ethyl ketone oxime, cyclohexanone oxime, benzophenone oxime, acetoxime and the like. Examples of the lactam compounds include ε-caprolactam, γ-butyrolactam and the like.

Examples of the phenol compounds include phenol, naphthol, cresol, xylenol, halogen-substituted phenol and the like.

Examples of the alcohol compounds include methanol, ethanol, propanol, butanol, cyclohexanol, ethylene glycol monoalkyl ether, propylene glycol monoalkyl ether, alkyl lactates and the like.

The amine compounds include primary amines and secondary amines, which may be any of aromatic amines, aliphatic amines or alicyclic amines, examples of which include aniline, diphenylamine, ethyleneimine, polyethyleneimine and the like.

Examples of the active methylene compounds include diethyl malonate, dimethyl malonate, ethyl acetoacetate, methyl acetoacetate and the like.

Examples of the pyrazole compounds include pyrazole, methylpyrazole, dimethylpyrazole and the like.

Examples of the mercaptan compounds include alkyl mercaptans, aryl mercaptans and the like.

Blocked isocyanate compounds that can be used in the photosensitive resin compositions of the present invention are commercially available, and examples that can be preferably used include CORONATE AP STABLE M, CORONATE 2503, 2515, 2507, 2513 and 2555, and Millionate MS-50 (all from Nippon Polyurethane Industry Co., Ltd.); TAKENATE B-830, B-815N, B-820NSU, B-842N, B-846N, B-870N, B-874N and B-882N (all from Mitsui Chemicals, Inc.); Duranate 17B-60PX, 17B-60P, TPA-B80X, TPA-B80E, MF-B60X, MF-B60B, MF-K60X, MF-K60B, E402-B80B, SBN-70D, SBB-70P and K6000 (all from Asahi Kasei Chemicals Corp.); Desmodur BL1100, BL1265 MPA/X, BL3575/1, BL3272MPA, BL3370MPA, BL3475BA/SN, BL5375MPA, VPLS2078/2, BL4265SN, PL340 and PL350, and Sumidur BL3175 (all from Sumika Bayer Urethane Co., Ltd.); and the like.

(F) Sensitizer

The photosensitive resin compositions of the present invention preferably comprise a sensitizer in combination with the photoacid generator (B) to promote its decomposition. The sensitizer is electronically excited once it absorbs active rays or radiation. The electronically excited sensitizer comes into contact with the photoacid generator to induce a phenomenon such as electron transfer, energy transfer, heat generation or the like. As a result, the photoacid generator undergoes a chemical change so that it decomposes to generate an acid. Preferred examples of sensitizers include compounds belonging to the following classes and having an absorption wavelength in any of the wavelength region of 350 nm to 450 nm.

Polynuclear aromatics (e.g., pyrene, perylene, triphenylene, anthracene, 9,10-dibutoxyanthracene, 9,10-diethoxyanthracene, 3,7-dimethoxyanthracene, 9,10-dipropyloxyanthracene); xanthenes (e.g., fluorescein, eosine, erythrosine, rhodamine B, rose bengal); xanthones (e.g., xanthone, thioxanthone, dimethylthioxanthone, diethylthioxanthone); cyanines (e.g., thiacarbocyanine, oxacarbocyanine); merocyanines (e.g., merocyanine, carbomerocyanine); rhodacyanines; oxonols; thiazines (e.g., thionine, methylene blue, toluidine blue); acridines (e.g., acridine orange, chloroflavine, acriflavine); acridones (e.g., acridone, 10-butyl-2-chloroacridone, 10-butylacridone); anthraquinones (e.g., anthraquinone); squaryliums (e.g., squarylium); styryls and styryl-based compounds (e.g., 2-[2-[4-(dimethylamino)phenyl]ethenyl]benzoxazole); and coumarins (e.g., 7-diethylamino-4-methylcoumarin, 7-hydroxy-4-methylcoumarin, 2,3,6,7-tetrahydro-9-methyl-1H,5H, 11H-[1]benzopyrano [6,7,8-i j]quinolizin-11-one).

Among these sensitizers, preferred are polynuclear aromatics, acridones, styryls and styryl-based compounds, and coumarins, more preferably polynuclear aromatics. Among polynuclear aromatics, most preferred are anthracene derivatives.

Preferably, the photosensitive resin compositions of the present invention contain the sensitizer in an amount of 0 to 1000 parts by mass, more preferably 10 to 500 parts by mass, still more preferably 50 to 200 parts by mass per 100 parts by mass of the photoacid generator in the photosensitive resin compositions.

Two or more of them can also be used in combination.

(G) Basic Compound

The photosensitive resin compositions of the present invention may comprise (G) a basic compound. The basic compound (G) that can be used is arbitrarily chosen from those used in chemically amplified resists. For example, they include aliphatic amines, aromatic amines, heterocyclic amines, quaternary ammonium hydroxide, quaternary ammonium salts of carboxylic acids and the like. Specific examples of them include the compounds described in paragraphs 0204 to 0207 of JP-A2011-221494, the contents of which are incorporated herein by reference. Alternatively, thioureas such as N-cyclohexyl-N'-[2-(4-morpholinyl)ethyl] thiourea may also be used.

Basic compounds that can be used in the present invention may be used alone or as a combination of two or more of them.

The content of the additional basic compound (G) in the photosensitive resin compositions of the present invention is preferably 0.001 to 3 parts by mass, more preferably 0.005 to 1 parts by mass per 100 parts by mass of the total solids in the photosensitive resin compositions if such an additional basic compound is contained.

(H) Surfactant

The photosensitive resin compositions of the present invention may comprise (H) a surfactant. Any of anionic, cationic, nonionic or zwitterionic surfactants can be used as the surfactant (H), but preferred surfactants are nonionic surfactants.

Examples of nonionic surfactants include polyoxyethylene higher alkyl ethers, polyoxyethylene higher alkyl phenyl ethers, higher fatty acid diesters of polyoxyethylene glycol, silicone surfactants, and fluorosurfactants. They are commercially available under the brand name series KP (from Shin-Etsu Chemical Co., Ltd.), POLYFLOW (from Kyoeisha Chemical Co., Ltd.), Eftop (from JEMCO, Inc.), MEGAFACE (from DIC Corporation), Fluorad (from Sumitomo 3M Limited), AsahiGuard and SURFLON (from Asahi Glass Co., Ltd.), PolyFox (from OMNOVA Solutions Inc.), SH-8400 (from Dow Corning Toray Co., Ltd.) and the like.

Further, preferred examples of surfactants include copolymers comprising the structural unit A and structural unit B represented by formula (H-1) below and having a weight average molecular weight (Mw) of 1,000 or more and 10,000 or less when determined as a polystyrene equivalent molecular weight by Gel Permeation Chromatography in tetrahydrofuran (THF) as a solvent.

formula (H-1)

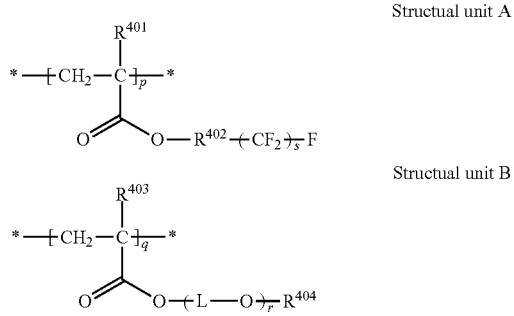

In formula (H-1), $R^{401}$ and $R^{403}$ each represent a hydrogen atom or GP a methyl group, $R^{402}$ represents a straight-chain alkylene group containing 1 to 4 carbon atoms, $R^{404}$ represents a hydrogen atom or an alkyl group containing 1 to 4 carbon atoms, L represents an alkylene group containing 3 to 6 carbon atoms, p and q are the percentages by mass representing the monomer ratio in the polymer, p represents a value of 10% by mass or more and 80% by mass or less, q represents a value of 20% by mass or more and 90% by mass or less, r represents an integer of 1 to 18, and s represents an integer of 1 to 10.

In the formula above, L preferably represents a branched-chain alkylene group represented by formula (H-2) below.

In formula (H-2), $R^{405}$ represents an alkyl group containing 1 to 4 carbon atoms, preferably an alkyl group containing 1 to 3 carbon atoms, more preferably an alkyl group containing 2 or 3 carbon atoms because of the compatibility and the wettability on the substrate surface. The sum of p and q (p+q) is preferably 100, i.e., 100% by mass.

formula (H-2)

More preferably, the copolymers have a weight average molecular weight (Mw) of 1,500 or more and 5,000 or less.

These surfactants can be used alone or as a mixture of two or more of them.

The amount of the surfactant (H) added to the photosensitive resin compositions of the present invention is preferably 10 parts by mass or less, more preferably 0.001 to 10 parts by mass, still more preferably 0.01 to 3 parts by mass per 100 parts by mass of the total solids in the photosensitive resin compositions.

(I) Antioxidant

The photosensitive resin compositions of the present invention may comprise an antioxidant. Known antioxidants can be contained. When an antioxidant is added, the following advantages are obtained: cured films can be prevented from staining; or the thickness loss by decomposition can be reduced; or transparency after heating can be improved.

Such antioxidants include, for example, phosphorus-based antioxidants, amides, hydrazides, hindered amine-based antioxidants, sulfur-based antioxidants, phenolic antioxidants, ascorbates, zinc sulfate, sugars, nitrites, sulfites, thiosulfates, hydroxylamine derivatives and the like. Among them, phenolic antioxidants, amide-based antioxidants, hydrazide-based antioxidants, and sulfur-based antioxidants are especially preferred to prevent cured films from staining and thickness loss. These may be used alone or as a mixture of two or more of them.

Commercially available products of phenolic antioxidants include, for example, ADEKA STAB AO-15, ADEKA STAB AO-18, ADEKA STAB AO-20, ADEKA STAB AO-23, ADEKA STAB AO-30, ADEKA STAB AO-37, ADEKA STAB AO-40, ADEKA STAB AO-50, ADEKA STAB AO-51, ADEKA STAB AO-60, ADEKA STAB AO-70, ADEKA STAB AO-80, ADEKA STAB AO-330, ADEKA STAB AO-412S, ADEKA STAB AO-503, ADEKA STAB A-611, ADEKA STAB A-612, ADEKA STAB A-613, ADEKA STAB PEP-4C, ADEKA STAB PEP-8, ADEKA STAB PEP-8W, ADEKA STAB PEP-24G, ADEKA STAB PEP-36, ADEKA STAB PEP-36Z, ADEKA STAB HP-10, ADEKA STAB 2112, ADEKA STAB 260, ADEKA STAB 522A, ADEKA STAB 1178, ADEKA STAB 1500, ADEKA STAB C, ADEKA STAB 135A, ADEKA STAB 3010, ADEKA STAB TPP, ADEKA STAB CDA-1, ADEKA STAB CDA-6, ADEKA STAB ZS-27, ADEKA STAB ZS-90 and ADEKA STAB ZS-91 (all from ADEKA CORPORATION); Irganox 245FF, Irganox 1010FF, Irganox 1010, Irganox MD1024, Irganox 1035FF, Irganox 1035, Irganox 1098, Irganox 1330, Irganox 1520L, Irganox 3114, Irganox 1726, Irgafos 168 and Irgamod 295 (from BASF Corporation); and the like. Among others, ADEKA STAB AO-60, ADEKA STAB AO-80, Irganox 1726, Irganox 1035, and Irganox 1098 can be conveniently used.

The content of the antioxidants is preferably 0.1 to 10% by mass, more preferably 0.2 to 5% by mass, especially preferably 0.5 to 4% by mass based on the total solids of the photosensitive resin compositions. When it is in the ranges defined above, the resulting films exhibit sufficient transparency and better sensitivity during patterning.

Further, additives other than the antioxidants that may be added to the photosensitive resin compositions of the present invention include various UV absorbers, metal deactivators and the like described in "New Developments in Polymer Additives (NIKKAN KOGYO SHIMBUN, LTD.)".

Acid Amplifier

In the photosensitive resin compositions of the present invention, an acid amplifier can be used to improve sensitivity.

The acid amplifier that can be used in the present invention is a compound that can further generate an acid by an acid catalytic reaction to increase the acid concentration in the reaction system and that is stably present in the absence of an acid. The strength of the acid generated by such a compound is preferably 3 or less, especially preferably 2 or less expressed as the acid dissociation constant pKa because the acid generated undergoes self-decomposition though the reaction proceeds acceleratingly as one or more acid is added in one cycle of reaction.

Specific examples of acid amplifiers include the compounds described in paragraphs 0203 to 0223 of JP-A-H10-1508; paragraphs 0016 to 0055 of JP-A-H10-282642; and page 39, line 12 to page 47, line 2 of JP-A-H9-512498; the contents of which are incorporated herein by reference.

Acid amplifiers that can be used in the present invention include compounds that are decomposed by the acid generated from the acid generator to generate an acid having a pKa of 3 or less such as dichloroacetic acid, trichloroacetic acid, methanesulfonic acid, benzenesulfonic acid, trifluoromethanesulfonic acid, phenylphosphonic acid or the like.

Specifically, examples include the following compounds and the like.

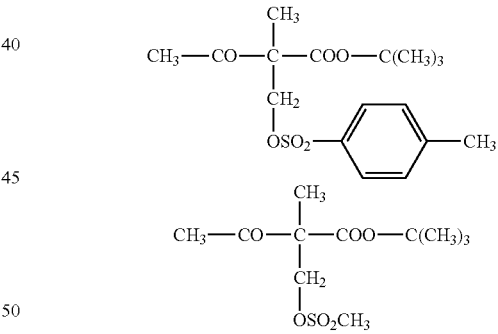

Preferably, the photosensitive compositions contain the acid amplifiers in an amount of 10 to 1,000 parts by mass, more preferably 20 to 500 parts by mass per 100 parts by mass of the photoacid generator to improve the dissolution rate contrast between exposed and unexposed areas.

[Accelerator]

The photosensitive resin compositions of the present invention can comprise an accelerator.

Description about accelerators can be found in paragraphs 0171 to 0172 of JP-A2012-042837, the contents of which are incorporated herein by reference.

The accelerators may be used alone or as a combination of two or more of them.

Preferably, the photosensitive resin compositions of the present invention contain the accelerators in an amount of 0 to 30 parts by mass, more preferably 0.1 to 20 parts by mass, most preferably 0.5 to 10 parts by mass per 100 parts by mass of the total solids of the photosensitive compositions to improve sensitivity and relative remaining film thickness after development.

Other additives that can be used include the heat-induced free radical generators described in paragraphs 0120 to 0121 of JP-A2012-8223; and the nitrogen-containing compounds and thermal acid generators described in WO2011/136074A1; the contents of which are incorporated herein by reference.

<Processes for Preparing the Photosensitive Resin Compositions>

The photosensitive resin compositions are prepared by mixing various components in predetermined proportions by a given method and dissolving them with stirring. For example, a resin composition can be prepared by dissolving each component in a solvent to prepare a solution in advance and then mixing the solutions in predetermined proportions. The solution of the composition thus prepared can also be used after it has been filtered through a filter having a pore size of 0.2 μm or the like

[Processes for Preparing Cured Films]

Next, processes for preparing cured films according to the present invention are explained.

Processes for preparing cured films according to the present invention preferably comprise the steps (1) to (5) of:
(1) coating a photosensitive resin composition of the present invention by coating on a substrate;
(2) removing the solvent from the applied photosensitive resin composition;
(3) exposing the photosensitive resin composition freed from the solvent to an active radiation;
(4) developing the exposed photosensitive resin composition by an aqueous developer; and
(5) postbaking the developed photosensitive resin composition to thermally cure it.

The individual steps will be explained in order below.

In the coating step (1), a photosensitive resin composition of the present invention is preferably applied by coating on a substrate to form a wet film containing a solvent.

Before the photosensitive resin composition is applied on the substrate, the substrate is preferably cleaned by alkaline cleaning or plasma cleaning or the like, and after the substrate has been cleaned, the substrate is more preferably further surface-treated with hexamethyldisilazane. This treatment tends to improve adhesion of the photosensitive resin composition to the substrate. The method by which the substrate surface is treated with hexamethyldisilazane is not specifically limited, but involves, for example, exposing the substrate to the vapor of hexamethyldisilazane or other means.

The substrate may be an inorganic substrate, a resin substrate or a resin composite material substrate or the like. Inorganic substrate include, for example, glass, quartz, silicone and silicon nitride substrates, as well as composite substrates obtained by depositing the vapor of molybdenum, titanium, aluminum, copper or the like on such substrates.

Resin substrates include substrates made of synthetic resins such as polybutylene terephthalate, polyethylene terephthalate, polyethylene naphthalate, polybutylene naphthalate, polystyrene, polycarbonate, polysulfone, polyethersulfone, polyallylate, allyl diglycol carbonate, polyamide, polyimide, polyamide-imide, polyetherimide, polybenzazol, polyphenylene sulfide, polycycloolefin, norbornene resins, fluororesins such as polychlorotrifluoroethylene, liquid crystal polymers, acrylic resins, epoxy resins, silicone resins, ionomer resins, cyanate resins, crosslinked fumaric acid diesters, cyclic polyolefins, aromatic ethers, maleimide-olefins, cellulose, episulfide compounds and the like.

These substrates are rarely used as such, but a multilayer structure such as a TFT device is typically formed thereon depending on the form of the end products.

Methods that can be used for coating the substrates are not specifically limited, but include, for example, slot die coating, spray coating, roll coating, spin coating, flow coating, slit and spin coating and the like. Further, the so-called prewetting technique as described in JP-A2009-145395 can also be applied.

The wet film thickness of the coating immediately after it has been applied is not specifically limited, and the coating can be applied in any thickness depending on the purposes, but it is typically used in a thickness ranging from 0.5 to 10 μm.

In the solvent removal step (2), the solvent is removed from the coating applied as described above by depressurization (vacuum) and/or heating to form a dry coating film on the substrate. Heating conditions during the solvent removal step preferably involve 70 to 130° C. for about 30 to 300 seconds. When the temperature and the period are in the ranges defined above, there is a tendency that adhesion of patterns is further improved and that residues can be further reduced.

In the exposure step (3), the coated substrate is irradiated with active rays through a mask having a desired pattern. In this step, the photoacid generator decomposes to generate an acid. The acid-decomposable group contained in the coating components is hydrolyzed by catalytic action of the generated acid to produce a carboxyl group or phenolic hydroxyl group.

Exposure sources of active rays that can be used include low pressure mercury lamps, high pressure mercury lamps, ultra-high pressure mercury lamps, chemical lamps, LED light sources, excimer laser oscillators and the like, and active rays that can be preferably used have a wavelength of 300 nm or more and 450 nm or less such as g-line (436 nm), i-line (365 nm), h-line (405 nm) or the like. Further, the irradiation light can be adjusted through spectral filters such as long-wavelength cut-off filters, short-wavelength cut-off filters, bandpass filter and the like as appropriate.

Exposure systems that can be used include various types of exposure systems such as mirror projection aligners, steppers, scanners, proximity systems, contact systems, microlens arrays, laser exposure systems and the like.

To accelerate the hydrolysis reaction in regions where the acid catalyst has been generated, the post-exposure bake (hereinafter sometimes referred to as "PEB") can be performed. PEB can promote the production of a carboxyl group or phenolic hydroxyl group from the acid-decomposable group. The temperature at which PEB takes place is preferably 30° C. or more and 130° C. or less, more preferably 40° C. or more and 110° C. or less, especially preferably 50° C. or more and 100° C. or less.

However, PEB may not necessarily take place but a positive image can be formed by development because the acid-decomposable group in the present invention has a low activation energy for acid decomposition so that it is readily decomposed by the acid derived from the acid generator via exposure to produce a carboxyl group or phenolic hydroxyl group.

In the developing step (4), the polymer containing the released carboxyl group or phenolic hydroxyl group is developed with an alkaline developer. The exposed areas comprising the resin composition containing the carboxyl group or phenolic hydroxyl group soluble in the alkaline developer are removed, whereby a positive image is formed.

The developer used in the developing step preferably comprises a basic compound. Basic compounds that can be used include, for example, aqueous solutions of alkali metal hydroxides such as lithium hydroxide, sodium hydroxide, potassium hydroxide and the like; alkali metal carbonate salts such as sodium carbonate, potassium carbonate and the like; alkali metal bicarbonate salts such as sodium bicarbonate, potassium bicarbonate and the like; ammonium hydroxides such as tetramethylammonium hydroxide, tetraethylammonium hydroxide, choline hydroxide and the like; sodium silicate, sodium metasilicate and the like. Further, aqueous solutions of the basic compounds described above further containing appropriate amounts of water-soluble organic solvents such as methanol or ethanol and surfactants can also be used as developers.

Preferred developers may include a 0.4% aqueous solution, a 0.5% aqueous solution, a 0.7% aqueous solution, and a 2.38% aqueous solution of tetraethylammonium hydroxide.

The pH of the developer is preferably 10.0 to 14.0.

The developing time is preferably 30 to 500 seconds, and any developing methods such as puddle process, dipping and the like may be applied. Development is followed by washing with running water typically for 30 to 300 seconds, whereby a desired pattern can be formed.

Development may be followed by a rinsing step. During the rinsing step, the substrate after development is rinsed with pure water or the like to remove the developer deposited on it and post-development residues. Known rinsing methods can be used.

For example, shower rinsing, dip rinsing and the like can be applied.

In the post baking step (5), the positive image thus formed is heated so that the acid-decomposable group is thermally decomposed to produce a carboxyl group or phenolic hydroxyl group, which can be crosslinked with a crosslinkable group, crosslinking agent or the like to form a cured film. This heating preferably takes place using a heater such as a hot plate or an oven at a predetermined temperature such as 180 to 250° C. for a predetermined period such as 5 to 90 minutes on a hot plate or 30 to 120 minutes in an oven. Such a crosslinking reaction is allowed to proceed, whereby protective layers or interlayer insulating layers having higher heat resistance, hardness and the like can be formed. Further, transparency can be further improved by performing the heat treatment in a nitrogen atmosphere.

Postbaking may be preceded by baking at a relatively low temperature (addition of an intermediate baking step). The intermediate baking step preferably comprises heating at 90 to 150° C. for 1 to 60 minutes followed by postbaking at a high temperature of 200° C. or more, if such a step is applied.

Alternatively, intermediate baking and postbaking may be performed by heating in three or more stages. The taper angles of patterns can be optimized by specially designing the intermediate baking and postbaking steps in this way. These heating steps can be performed by using a known heating method such as a hot plate, oven, infrared heater or the like.

Alternatively, postbaking may be preceded by wholly re-exposing the patterned substrate to active rays (post-exposure), whereby an acid can be generated from the photoacid generator present in unexposed areas to serve as a catalyst for promoting the crosslinking process, thus promoting the curing reaction of the film. When the post-exposure step is included, the exposure dose is preferably 100 to 3,000 mJ/cm$^2$, especially preferably 100 to 500 mJ/cm$^2$.

Further, the cured film obtained from the photosensitive resin composition of the present invention can also be used as a dry etching resist. When the cured film obtained by thermal curing through the postbaking step is used as a dry etching resist, it can be subjected to dry etching processes such as ashing, plasma etching, ozone etching and the like.

[Cured Films]

The cured films of the present invention are obtained by curing the photosensitive resin compositions of the present invention The cured films of the present invention can be conveniently used as interlayer insulating layers. Further, the cured films of the present invention are preferably obtained by the processes for forming cured films according to the present invention.

The photosensitive resin compositions of the present invention can provide interlayer insulating layers having high insulating ability and high transparency even when they are baked at high temperatures. The interlayer insulating layers using the photosensitive resin compositions of the present invention have high transparency and excellent cured film properties so that they are useful in applications for organic EL display devices and liquid crystal display devices.

[Liquid Crystal Display Devices]

The liquid crystal display devices of the present invention are characterized in that they comprise a cured film of the present invention.

The liquid crystal display devices of the present invention are not specifically limited except that they comprise a planarization layer or an interlayer insulating layer formed by using a photosensitive resin composition of the present invention as described above, and they include known liquid crystal display devices having various structures.

For example, specific examples of TFTs (Thin-Film Transistors) used in the liquid crystal display devices of the present invention include amorphous silicon-TFTs, low temperature polysilicon-TFTs, oxide semiconductor TFTs and the like. The cured films of the present invention can preferably be used in combination with these TFTs because they have high electrical properties.

Further, liquid crystal driving modes that can be employed by the liquid crystal display devices of the present invention include TN (Twisted Nematic) mode, VA (Vertical Alignment) mode, IPS (In-Place-Switching) mode, FFS (Fringe Field Switching) mode, OCB (Optically Compensated Bend) mode and the like.

The cured films of the present invention can also be used in liquid crystal display devices having a COA (Color Filter on Array) technology-based panel architecture, and specifically they can be used as the organic insulating layer (115) of JP-A2005-284291 or the organic insulating layer (212) of JP-A2005-346054, for example.

Specific techniques that can be employed for aligning liquid crystal alignment films of the liquid crystal display devices of the present invention include rubbing, photo-alignment and the like. Alternatively, alignment may be stabilized by polymerization according to the PSA (Polymer Sustained Alignment) technology described in JP-A2003-149647 and JP-A2011-257734.

Further, the photosensitive resin compositions of the present invention and the cured films of the present invention are not limited to the applications described above, but can be used for various applications. For example, they can be conveniently used as not only planarization layers or interlayer insulating layers but also protective layers of color filters, spacers for maintaining a uniform thickness of liquid crystal layers in liquid crystal display devices, microlens on color filters in solid-state image sensors and the like.

FIG. 1 is a schematic sectional view showing an example of an active matrix liquid crystal display device 10. This color liquid crystal display device 10 is a liquid crystal panel having a backlight unit 12 on the back side, and the liquid crystal panel comprises TFT elements 16 corresponding to all pixels disposed between two glass substrate 14, 15 covered with apolarizing film. Each element formed on the glass substrate is connected with an ITO transparent electrode 19 forming a pixel electrode through a contact hole 18 formed in a cured film 17. On the ITO transparent electrode 19 is provided a RGB color filter 22 comprising a liquid crystal layer 20 and a black matrix.

The backlight source is not specifically limited, but known light sources can be used. For example, a white LED, a multicolor LED combining blue, red and green or the like, a fluorescent lamp (cold cathode tube), an organic EL or the like may be used.

Further, the liquid crystal display device may be a 3D (three-dimensional) display device or a touch panel display device. Alternatively, it may be a flexible display device in which the cured film can be used as the second interlayer insulating layer (48) of JP-A2011-145686 or the interlayer insulating layer (520) of JP-A2009-258758.

[Organic EL Display Devices]

The organic EL display devices of the present invention are characterized in that they comprises a cured film of the present invention.

The organic EL display devices of the present invention are not specifically limited except that they comprise a planarization layer or an interlayer insulating layer formed by using a photosensitive resin composition of the present invention as described above, and they include known various organic EL display devices and liquid crystal display devices having various structures.

For example, specific examples of TFTs (Thin-Film Transistors) used in the organic EL display devices of the present invention include amorphous silicon-TFTs, low temperature polysilicon-TFTs, oxide semiconductor TFTs and the like. The cured films of the present invention can preferably be used in combination with these TFTs because they have high electrical properties.

Figure 2:
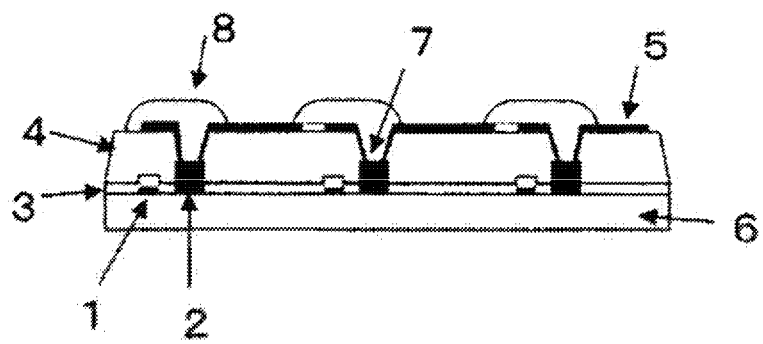
FIG. 2 shows a schematic diagram of an example of an organic EL display device. A schematic sectional view of a matrix array in a bottom-emission organic EL display device is shown, which comprises a planarization layer 4.

FIG. 2 shows a schematic diagram of an example of an organic EL display device. A schematic sectional view of a matrix array in a bottom-emission organic EL display device is shown, which comprises a planarization layer 4.

A bottom gate TFT 1 is formed on a glass substrate 6, and an insulating layer 3 made of $Si_3N_4$ is formed to cover the TFT 1.

A contact hole not shown in the figure is formed in the insulating layer 3, and then a wiring 2 (height 1.0 µm) to be connected with the TFT 1 through the contact hole is formed on the insulating layer 3. The wiring 2 is intended to connect TFTs 1 or an organic EL device that will be formed during a subsequent step and a TFT 1.

Further, a planarization layer 4 is formed on the insulating layer 3 to fill irregularities caused by forming the wiring 2 so that the irregularities caused by the wiring 2 are flattened.

A bottom-emission organic EL device is formed on the planarization layer 4. Thus, a first electrode 5 made of ITO is formed on the planarization layer 4 in such a manner that it is connected with the wiring 2 through the contact hole 7. The first electrode 5 corresponds to an anode of the organic EL device.

An insulating layer 8 is formed to cover the periphery of the first electrode 5, whereby short circuits between the first electrode 5 and a second electrode to be formed during a subsequent step can be prevented.

Further, a hole transport layer, an organic light emitting layer, and an electron transport layer not shown in FIG. 2 are successively formed by vapor deposition through a mask having a desired pattern, and then a second electrode made of Al is formed over the entire surface of the top of the substrate, and finally the assembly is sealed by adhering it to a sealing glass panel using a UV-curable epoxy resin, thereby giving an active matrix organic EL display device comprising organic EL elements each connected with the TFT 1 for driving them.

The photosensitive resin compositions of the present invention have high curability and cured film properties so that they are used as structural members of MEMS devices such as spacers comprising resist patterns formed from the photosensitive resin compositions of the present invention or parts of mechanical actuating members in which they are incorporated. Such MEMS devices include, for example, components such as SAW filters, BAW filters, gyroscope sensors, microshutters for displays, image sensors, electronic paper, inkjet printheads, biochips, sealants and the like. More specific examples are shown in JP-A 2007-522531, JP-A2008-250200, JP-A2009-263544 and the like.

The photosensitive resin compositions of the present invention are excellent in flatness and transparency so that they can also be used for forming, for example, the bank layer (16) and the planarization layer (57) described in FIG. 2 of JP-A2011-107476; the spacer (12) and the planarization layer (102) described in FIG. 4(a) of JP-A2010-9793; the bank layer (221) and the third interlayer insulating layer (216b) described in FIG. 10 of JP-A2010-27591; the second interlayer insulating layer (125) and the third interlayer insulating layer (126) described in FIG. 4(a) of JP-A2009-128577; the planarization layer (12) and the pixel-separating insulating layer (14) described in FIG. 3 of JP-A2010-182638; and the like.

EXAMPLES

The following examples further illustrate the present invention. The materials, amounts used, proportions, process details, procedures and the like shown in the following examples can be changed as appropriate without departing from the spirit of the present invention. Thus, the scope of the present invention is not limited to the specific examples shown below. Unless otherwise specified, the "parts" and "%" are based on mass.

In the following synthesis examples, the following abbreviations mean the compounds below, respectively. V-65: 2,2'-Azobis(2,4-dimethylvaleronitrile) (from Wako Pure Chemical Industries, Ltd.)

V-601: Dimethyl-2,2'-azobis(2-methyl propionate) (from Wako Pure Chemical Industries, Ltd.)

MAEVE: 1-Ethoxyethyl methacrylate

MATHF: Tetrahydro-2H-furan-2-yl methacrylate

MATHP: Tetrahydro-2H-pyran-2-yl methacrylate

CHOEMA: Cyclohexyloxyethyl methacrylate

P-Ph-1: 1-Ethoxyethyl ether of 4-hydroxybenzoic acid (3-methacryloyloxypropyl) ester StOEVE: 4-(1-Ethoxyethyloxy)styrene GMA: Glycidyl methacrylate OXE-30: (3-Ethyloxetane-3-yl)methyl methacrylate (from Osaka Organic Chemical Industry Ltd.)

IBMAA: i-Butoxymethyl acrylamide (from Tokyo Chemical Industry Co., Ltd.)

MMAA: Methoxymethyl acrylamide (from MRC UNITEC Co., Ltd.)

M100: 3,4-Epoxycyclohexylmethy methacrylate (from Daicel Corporation)

MMA: Methyl methacrylate

MAA: Methacrylic acid

Ph-1: 4-Hydroxybenzoic acid (3-methacryloyloxypropyl) ester
HEMA: 2-Hydroxyethyl methacrylate
DCPMA: Dicyclopentanyl methacrylate
St: Styrene
THFFMA: Tetrahydrofurfuryl methacrylate
PHS: p-Hydroxystyrene
EDM: Diethylene glycol ethyl methyl ether (Hisolve EDM from TOHO CHEMICAL INDUSTRY Co., Ltd.)
PGMEA: Propylene glycol monomethyl ether acetate.

Synthesis of Polymer A-1

To 144.2 parts (2 molar equivalents) of ethyl vinyl ether was added 0.5 parts of phenothiazine, and 86.1 parts (1 molar equivalent) of methacrylic acid was added dropwise while the reaction system was cooled at 10° C. or less, and then the mixture was stirred at room temperature (25° C.) for 4 hours. After 5.0 parts of pyridinium p-toluenesulfonate was added, the mixture was stirred at room temperature for 2 hours and allowed to stand overnight at room temperature. To the reaction solution were added 5 parts of sodium bicarbonate and 5 parts of sodium sulfate, and the mixture was stirred at room temperature for 1 hour, filtered off insolubles and then concentrated under reduced pressure at 40° C. or less, and the residual yellow oil was distilled under reduced pressure to give 134.0 parts of 1-ethoxyethyl methacrylate (MAEVE) as a colorless oil corresponding to a fraction having a boiling point (bp.) of 43 to 45° C. at 7 mmHg.

A mixed solution of the resulting 1-ethoxyethyl methacrylate (63.28 parts (0.4 molar equivalents)), GMA (42.65 parts (0.3 molar equivalents)), MAA (8.61 parts (0.1 molar equivalents)), HEMA (26.03 parts (0.2 molar equivalents)) and EDM (110.8 parts) was heated to 70° C. under a stream of nitrogen gas. To this mixed solution was added a mixed solution of the radical polymerization initiator V-65 (brand name from Wako Pure Chemical Industries, Ltd.; 4 parts) and EDM (100.0 parts) dropwise over 2.5 hours with stirring. After completion of the dropwise addition, the mixture was reacted at 70° C. for 4 hours to give a solution of polymer A-1 in EDM (solids content: 40%).

The weight average molecular weight of the resulting polymer A-1 determined by gel permeation chromatography (GPC) was 15,000.

Synthesis of CHOEMA

CHOEMA was synthesized in the same manner as the synthesis procedure of MAEVE in the synthesis of polymer A-1 described above.

Synthesis of MATHF

To methacrylic acid (86 g, 1 mol) cooled to 15° C. was added camphorsulfonic acid (4.6 g, 0.02 mol). To this solution was added dropwise 2-dihydrofuran (71 g, 1 mol, 1.0 eq.). After stirring for 1 hour, saturated sodium bicarbonate (500 mL) was added, and the mixture was extracted with ethyl acetate (500 mL), dried over magnesium sulfate, then filtered off insolubles and then concentrated under reduced pressure at 40° C. or less, and the residual yellow oil was distilled under reduced pressure to give 125 g of tetrahydro-2H-furan-2-yl methacrylate (MATHF) as a colorless oil corresponding to a fraction having a boiling point (bp.) of 54 to 56° C. at 3.5 mmHg (yield 80%).

Synthesis of Ph-1

To a solution of 23 g of 4-hydroxybenzoic acid (3-hydroxypropyl)ester in 100 ml of acetonitrile was added 20 ml of N-methylpyrrolidone with stirring, followed by 16 g of methacryloyl chloride. After the mixture was reacted with stirring at 35° C. for 8 hours, the reaction mixture was poured into ice water, and the precipitated crystals were collected by filtration and recrystallized from ethyl acetate/n-hexane to give 4-hydroxybenzoic acid (3-methacryloyloxypropyl)ester (Ph-1).

Synthesis of P-Ph-1

P-Ph-1 was obtained by protecting Ph-1 with 1-ethoxyethyl ether.

Synthesis of Other Polymers

Other copolymers were synthesized in the same manner as described for the synthesis of polymer A-1 except that the monomers used and their amounts used were changed to those described in the table below.

TABLE 1

| Polymer | (a1) Monomer Kind | Molar equivalent | (a2) Monomer Kind | Molar equivalent | Other monomer 1 Kind | Molar equivalent | Other monomer 2 Kind | Molar equivalent | Other monomer 3 Kind | Molar equivalent | Mw |
|---|---|---|---|---|---|---|---|---|---|---|---|
| A-1 | MAEVE | 0.4 | GMA | 0.3 | MAA | 0.1 | HEMA | 0.2 | | | 15000 |
| A-2 | MATHF | 0.4 | OXE-30 | 0.3 | MAA | 0.1 | HEMA | 0.2 | | | 17000 |
| A-3 | MATHF | 0.54 | OXE-30 | 0.3 | MAA | 0.14 | HEMA | 0.02 | | | 15000 |
| A-4 | | | GMA | 0.67 | MAA | 0.15 | St | 0.17 | DCPMA | 0.01 | 12000 |
| A-5 | | | NBMA | 0.2 | MAA | 0.18 | St | 0.49 | MMA | 0.13 | 10000 |
| A-6 | MATHF | 0.66 | | | MAA | 0.13 | MMA | 0.21 | | | 15000 |
| A-7 | MATHF | 0.8 | | | MAA | 0.2 | | | | | 16000 |
| A-8 | MAEVE | 0.35 | GMA | 0.39 | MAA | 0.08 | HEMA | 0.11 | St | 0.07 | 9000 |
| A-9 | | | OXE-30 | 0.55 | MAA | 0.2 | MMA | 0.25 | | | 11000 |
| A-10 | | | MMAA | 0.15 | Ph-1 | 0.2 | St | 0.25 | MMA | 0.4 | 10000 |
| A-11 | CHOEMA | 0.4 | OXE-30 | 0.25 | MAA | 0.1 | HEMA | 0.05 | MMA | 0.2 | 18000 |
| A-12 | CHOEMA | 0.5 | GMA | 0.3 | MAA | 0.1 | HEMA | 0.1 | | | 14000 |
| A-13 | P-Ph-1 | 0.35 | OXE-30 | 0.25 | Ph-1 | 0.1 | MMA | 0.2 | St | 0.1 | 12000 |
| A-14 | MATHP | 0.4 | OXE-30 | 0.3 | MAA | 0.1 | HEMA | 0.2 | | | 13000 |
| A-15 | | | IBMAA | 0.15 | MAA | 0.15 | St | 0.5 | THFFMA | 0.2 | 10000 |
| A-16 | | | MMAA | 0.2 | MAA | 0.2 | MMA | 0.55 | DCPMA | 0.05 | 11000 |
| A-17 | MAEVE | 0.45 | M100 | 0.35 | MAA | 0.15 | HEMA | 0.05 | | | 18000 |
| A-18 | StOEVE | 0.3 | M100 | 0.3 | Ph-1 | 0.1 | MMA | 0.2 | DCPMA | 0.1 | 12000 |

TABLE 1-continued

| Polymer | (a1) Monomer | | (a2) Monomer | | Other monomer 1 | | Other monomer 2 | | Other monomer 3 | | Mw |
| --- | --- | --- | --- | --- | --- | --- | --- | --- | --- | --- | --- |
| | Kind | Molar equivalent | Kind | Molar equivalent | Kind | Molar equivalent | Kind | Molar equivalent | Kind | Molar equivalent | |
| A-19 | MATHF | 0.45 | GMA | 0.25 | MAA | 0.1 | PHS | 0.1 | MMA | 0.1 | 15000 |
| A-20 | MATHP | 0.55 | GMA | 0.35 | MAA | 0.05 | St | 0.04 | MMA | 0.01 | 15000 |

Synthesis of B-1

A mixture of 5.0 g of o-aminothiophenol (from Wako Pure Chemical Industries, Ltd.) and 5.0 g of pivaloyl acetonitrile (from Tokyo Chemical Industry Co., Ltd.) was stirred at 120° C. for 2 hours.

After the reaction mixture was allowed to cool, the crude product was purified by column chromatography on silica gel to give 5.7 g of an intermediate B-1A.

To a mixture of THF (3 mL) and B-1A (5.6 g) were added dropwise 24 mL of a 2 M hydrochloric acid/THF solution, then isopentyl nitrite (from Wako Pure Chemical Industries, Ltd.) (3.4 g) with ice-cooling, and the mixture was warmed to room temperature and then stirred for 2 hours. The resulting reaction mixture was partitioned between water and ethyl acetate, and the organic layer was washed with water, then dried over magnesium sulfate, filtered, and concentrated to give a crude intermediate B-1B.

To a mixture of the crude intermediate B-1B in acetone (20 mL) were added triethylamine (from Wako Pure Chemical Industries, Ltd.) (4.9 g) and p-toluenesulfonyl chloride (from Tokyo Chemical Industry Co., Ltd.) (5.9 g) with ice-cooling, and then the mixture was warmed to room temperature and stirred for 1 hour. The resulting reaction mixture was partitioned between water and ethyl acetate, and the organic phase was dried over magnesium sulfate, and then filtered and concentrated to give crude B-1.

The crude B-1 was reslurried with methanol, and then filtered and dried to give B-1 (6.0 g).

$^1$H-NMR spectrum of B-1 (300 MHz, CDCl$_3$): δ=8.1-8.0 (m, 1H), 7.9 (d, 2H), 7.9-7.8 (m, 1H), 7.6-7.5 (m, 2H), 7.4 (d.2H), 2.4 (s, 3H), 1.4 (s, 9H).

Synthesis of B-2

B-2 was synthesized in the same manner as described for B-1 except that pivaloyl acetonitrile in the synthesis of B-1 was replaced by benzoyl acetonitrile (from Tokyo Chemical Industry Co., Ltd.).

$^1$H-NMR spectrum of B-2 (300 MHz, CDCl$_3$): δ=8.0 (m, 1H), 7.9-7.8 (m, 5H), 7.7-7.6 (m, 1H), 7.5-7.4 (m, 4H), 7.4 (d.2H), 2.4 (s, 3H).

Synthesis of B-3 to B-5, and B-13 to B-15

These were synthesized according to standard procedures in the same manner as described for the synthesis of B-1.

Synthesis of B-6

To a mixture of 3.0 g of 2-aminophenol (from Tokyo Chemical Industry Co., Ltd.) and 8.7 g of methyl 4,4-dimethyl-3-oxovalerate (from Wako Pure Chemical Industries, Ltd.) was added 0.5 g of p-toluenesulfonic acid monohydrate (from Wako Pure Chemical Industries, Ltd.), and the mixture was heated at 120° C. for 2 hours in a nitrogen atmosphere.

After the reaction mixture was allowed to cool, the crude product was purified by column chromatography on silica gel to give 4.4 g of an intermediate B-6A.

To a mixture of B-6A (2.0 g) in p-xylene (10 mL) was added 0.3 g of p-toluenesulfonic acid monohydrate (from Wako Pure Chemical Industries, Ltd.), and the mixture was heated at 140° C. for 6 hours. The reaction mixture was allowed to cool, and then partitioned between water and ethyl acetate, and the organic phase was dried over magnesium sulfate, and then filtered and concentrated to give crude B-6B.

To a mixture of the entire amount of the crude B-9B in THF (1.5 mL) were added dropwise 8.5 mL of a 2 M hydrochloric acid/THF solution, and then isopentyl nitrite (from Wako Pure Chemical Industries, Ltd.) (1.2 g) with ice-cooling, and the mixture was warmed to room temperature and then stirred for 2 hours. The resulting reaction mixture was partitioned between water and ethyl acetate, and the organic layer was washed with water, then dried over magnesium sulfate, filtered, and concentrated to give a crude intermediate B-6C.

To a mixture of the crude intermediate B-6C (1.0 g) in acetone (10 mL) were added dropwise triethylamine (from Wako Pure Chemical Industries, Ltd.) (0.74 g) and p-toluenesulfonyl chloride (from Tokyo Chemical Industry Co., Ltd.) (1.0 g) with ice-cooling, and then the mixture was warmed to room temperature and stirred for 1 hour. The resulting reaction mixture was partitioned between water and ethyl acetate, and the organic phase was dried over magnesium sulfate, and then filtered and concentrated to give crude B-6. The crude B-6 was reslurried with methanol, and then filtered and dried to give B-6 (1.0 g).

$^1$H-NMR spectrum of B-6 (300 MHz, CDCl$_3$): δ=8.0-7.9 (m, 2H), 7.8-7.7 (m, 1H), 7.7-7.6 (m, 1H), 7.5-7.4 (m, 1H), 7.4-7.3 (m.3H), 2.4 (s, 3H), 1.3 (s, 9H).

Synthesis of B-7

B-7 was synthesized in the same manner as described for B-1 except that o-aminothiophenol in the synthesis of B-1 was replaced by 2-amino-4-chlorobenzenethiol (from Tokyo Chemical Industry Co., Ltd.).

Synthesis of B-8

B-8 was synthesized in the same manner as described for B-6 except that 2-aminophenol in the synthesis of B-6 was replaced by 2-amino-1-naphthol hydrochloride (from Tokyo Chemical Industry Co., Ltd.).

Synthesis of B-9

To a suspension of 4.0 g of 1-amino-2-naphthol hydrochloride (from Tokyo Chemical Industry Co., Ltd.) in 16 g of N-methylpyrrolidone (from Wako Pure Chemical Industries, Ltd.) was added 3.4 g of sodium bicarbonate (from Wako Pure Chemical Industries, Ltd.), and then 4.9 g of methyl 4,4-dimethyl-3-oxovalerate (from Wako Pure Chemical Industries, Ltd.) was added dropwise, and the mixture was heated at 120° C. for 2 hours in a nitrogen atmosphere. The reaction mixture was allowed to cool, and then partitioned between water and ethyl acetate, and the organic phase was dried over magnesium sulfate, filtered, and concentrated to give crude B-9A. The crude B-9A was purified by column chromatography on silica gel to give 1.7 g of an intermediate B-9A.

To a mixture of B-9A (1.7 g) in p-xylene (6 mL) was added 0.23 g of p-toluenesulfonic acid monohydrate (from Wako Pure Chemical Industries, Ltd.), and the mixture was heated at 140° C. for 2 hours. The reaction mixture was allowed to cool, and then partitioned between water and ethyl acetate, and the organic phase was dried over magnesium sulfate, and then filtered and concentrated to give crude B-9B.

To a mixture of the entire amount of the crude B-9B in THF (2 mL) were added dropwise 6.0 mL of a 2 M hydrochloric acid/THF solution, and then isopentyl nitrite (from Wako Pure Chemical Industries, Ltd.) (0.84 g) with ice-cooling, and the mixture was warmed to room temperature and then stirred for 2 hours. The resulting reaction mixture was partitioned between water and ethyl acetate, and the organic layer was washed with water, then dried over magnesium sulfate, filtered, and concentrated to give a crude intermediate B-9C.

To a mixture of the entire amount of the crude intermediate B-9C in acetone (10 mL) were added dropwise triethylamine (from Wako Pure Chemical Industries, Ltd.) (1.2 g) and p-toluenesulfonyl chloride (from Tokyo Chemical Industry Co., Ltd.) (1.4 g) with ice-cooling, and then the mixture was warmed to room temperature and stirred for 1 hour. The resulting reaction mixture was partitioned between water and ethyl acetate, and the organic phase was dried over magnesium sulfate, and then filtered and concentrated to give crude B-9. The crude B-9 was reslurried with cold methanol, and then filtered and dried to give B-9 (1.2 g).

$^1$H-NMR spectrum of B-9 (300 MHz, CDCl$_3$): δ=8.5-8.4 (m, 1H), 8.0-7.9 (m, 4H), 7.7-7.6 (m, 2H), 7.6-7.5 (m, 1H), 7.4 (d, 2H), 2.4 (s, 3H), 1.4 (s, 9H).

Synthesis of B-10 to B-12

These were synthesized according to standard procedures in the same manner as described for the synthesis of B-6.

Synthesis of B-16

B-16 was synthesized in the same manner as described for B-1 except that p-toluenesulfonyl chloride in the synthesis of B-1 was replaced by 2-thiophenesulfonyl chloride (from Tokyo Chemical Industry Co., Ltd.).

Synthesis of B-17, B-20, and B-21

These were synthesized according to standard procedures in the same manner as described for the synthesis of B-6.

Synthesis of B-18, B-22, and B-25

These were synthesized according to standard procedures in the same manner as described for the synthesis of B-1.

Synthesis of B-23

To a suspension of 5.0 g of 1-(1-naphthyl)-2-thiourea (from Wako Pure Chemical Industries, Ltd.) in 100 mL of acetic acid was added in portions 9.6 g of benzyltrimethylammonium tribromide (from Tokyo Chemical Industry Co., Ltd.), and the mixture was stirred at room temperature for 8 hours. The reaction mixture was added dropwise to a saturated aqueous sodium bicarbonate solution (1.6 L) in an ice bath, and extracted with ethyl acetate (300 mL), and the organic phase was dried over magnesium sulfate, and then filtered and concentrated to give crude B-23A (4.9 g).

The resulting crude B-23A (4.9 g) was added to ethylene glycol (50 mL), and a 50% aqueous solution of sodium hydroxide (12.2 g) was added, and then the mixture was heated under reflux for 48 hours in a nitrogen atmosphere. The reaction mixture was allowed to cool, and then added to a mixture of acetic acid (40 mL) and water (120 mL) with ice-cooling, and extracted with diethyl ether (150 mL). The organic phase was dried over magnesium sulfate, and then filtered and concentrated to give crude B-23B.

The entire amount of the resulting crude B-23B was mixed with pivaloyl acetonitrile (from Tokyo Chemical Industry Co., Ltd.), and the mixture was stirred at 140° C. for 6 hours. After the reaction mixture was allowed to cool, the crude product was purified by column chromatography on silica gel to give 2.1 g of an intermediate B-23C.

To a mixture of B-23C (2.0 g) in THF (3 mL) were added dropwise 7.1 mL of a 2 M hydrochloric acid/THF solution, then isopentyl nitrite (from Wako Pure Chemical Industries, Ltd.) (1.0 g) with ice-cooling, and the mixture was warmed to room temperature and then stirred for 2 hours. The resulting reaction mixture was partitioned between water and ethyl acetate, and the organic layer was washed with water, then dried over magnesium sulfate, filtered, and concentrated to give a crude intermediate B-23D.

To a mixture of the crude intermediate B-23D in acetone (10 mL) were added triethylamine (from Wako Pure Chemical Industries, Ltd.) (1.1 g) and p-toluenesulfonyl chloride (from Tokyo Chemical Industry Co., Ltd.) (1.35 g) with ice-cooling, and then the mixture was warmed to room temperature and stirred for 1 hour.

The resulting reaction mixture was partitioned between water and ethyl acetate, and the organic phase was dried over magnesium sulfate, and then filtered and concentrated to give crude B-23.

The crude B-23 was reslurried with cold methanol, and then filtered and dried to give B-23 (1.7 g).

$^1$H-NMR spectrum of B-23 (300 MHz, CDCl$_3$): δ=8.7-8.6 (m, 1H), 8.0-7.9 (m, 3H), 7.9-7.8 (m, 2H), 7.7-7.65 (m, 1H), 7.65-7.6 (m, 1H), 7.4 (d.2H), 2.4 (s, 3H), 1.4 (s, 9H).

Synthesis of B-19

This was synthesized according to standard procedures in the same manner as described for the synthesis of B-23.

Synthesis of B-24

B-24 was synthesized in the same manner as described for B-6 except that 2-aminophenol in the synthesis of B-6 was replaced by 3-amino-2-naphthol (from Tokyo Chemical Industry Co., Ltd.).

Synthesis of B-26

B-26 was synthesized in the same manner as described for B-6 except that 2-aminophenol in the synthesis of B-6 was replaced by 6-amino-2,4-dichloro-3-methylphenol (from Wako Pure Chemical Industries, Ltd.).

Synthesis of B-27

B-27 was synthesized in the same manner as described for B-6 except that 2-aminophenol in the synthesis of B-6 was replaced by 2-amino-4-phenylphenol (from Tokyo Chemical Industry Co., Ltd.).

Synthesis of B-28

B-28 was synthesized in the same manner as described for B-9 except that methyl 4,4-dimethyl-3-oxovalerate in the synthesis of B-9 was replaced by methyl 4-methyl-3-oxovalerate (from Tokyo Chemical Industry Co., Ltd.).

Synthesis of B-29

B-29 was synthesized in the same manner as described for B-9 except that methyl 4,4-dimethyl-3-oxovalerate in the synthesis of B-6 was replaced by benzoylethyl acetate (from Tokyo Chemical Industry Co., Ltd.).

Example 1

The following components were dissolved/mixed in the composition B shown below, and the mixture was filtered through a polytetrafluoroethylene filter having a pore size of 0.2 μm to give the photosensitive resin composition of Example 47. A solution of the photosensitive resin composition was prepared using the solvent (C) shown in Table 3 or Table 4 so that the concentration of the components other than the solvent (C) (referred to as solids content) equaled 20% by mass.

| <Composition B> (solids per 100 parts of copolymer (A)) | |
|---|---|
| Polymer (A): a solution of polymer A-1 in PGMEA | 100.0 parts |
| Photoacid generator (B): B-1 | 2.0 parts |
| Alkoxysilane compound (adhesion improver) (D): D-1 shown below | 8.0 parts |
| Crosslinking agent (E): E-1 shown below | 6.0 parts |
| Sensitizer (F): F-1 shown below | 2.0 parts |
| Basic compound (G): G-1 shown below | 0.05 parts |
| Basic compound (G): G-2 shown below | 0.1 parts |
| Antioxidant (I): I-1 shown below | 2.0 parts |

Examples 2 to 46 and Comparative Examples 1 to 3

The photosensitive resin compositions of Examples 2 to 46 and Comparative examples 1 to 3 were prepared by dissolving/mixing the compounds shown in the table below in place of the compounds used in Example 1 in the same amounts as added in Example 1. Some compounds were added in the ratios indicated in the table in a total amount equal to the amount added in Example 1.

Example 47

The following components were dissolved/mixed in the composition B shown below, and the mixture was filtered through a polytetrafluoroethylene filter having a pore size of 0.2 μm to give the photosensitive resin composition of Example 47. A solution of the photosensitive resin composition was prepared using the solvent (C) shown in Table 3 or Table 4 so that the concentration of the components other than the solvent (C) (referred to as solids content) equaled 20% by mass.

| <Composition B> (solids per 100 parts of copolymer (A)) | |
|---|---|
| Polymer (A): a solution of polymer A-1 in PGMEA | 100.0 parts |
| Photoacid generator (B): B-1 | 2.0 parts |
| Alkoxysilane compound (adhesion improver) (D): D-1 shown below | 8.0 parts |
| Crosslinking agent (E): E-1 shown below | 6.0 parts |
| Sensitizer (F): F-1 shown below | 2.0 parts |
| Basic compound (G): G-1 shown below | 0.05 parts |
| Basic compound (G): G-2 shown below | 0.1 parts |
| Antioxidant (I): I-1 shown below | 2.0 parts |

Examples 47 to 96 and Comparative Examples 4 to 6

The photosensitive resin compositions of Examples 47 to 94 and Comparative examples 4 to 6 were prepared by dissolving/mixing the compounds shown in the tables below in place of the compounds used in Example 47 in the same amounts as added in Example 47.

Some compounds were added in the ratios indicated in the tables in a total amount equal to the amount added in Example 47. Some basic compounds, surfactants and antioxidants were added in the amounts indicated instead of the amounts added in Example 47.

The abbreviations for the compounds used in the Examples and Comparative examples have the following meanings:

A-21: ARUFON UC-3920 (from Toagosei Co., Ltd.)
A-22: Joncryl 67 (from BASF)
B'-28: Compound b-8 described in JP-A2012-42836
B'-29: Compound b-12 described in JP-A2012-42836
B'-30: Compound b-1 described in JP-A2012-42836
C-1: PGMEA (Propylene glycol monomethyl ether acetate)
C-2: EDM (diethylene glycol ethyl methyl ether (Hisolve EDM from TOHO CHEMICAL INDUSTRY Co., Ltd.))
C-3: 1,3-Butylene glycol diacetate (from Daicel Corporation)
D-1: KBM-403 (brand name from Shin-Etsu Chemical Co., Ltd.; 3-glycidoxypropyltrimethoxysilane having the structure shown below)
D-2: KBE-846 (from Shin-Etsu Chemical Co., Ltd.)
D-3: KBM-3103 (from Shin-Etsu Chemical Co., Ltd.)
E-1: JER157S65 (brand name from Mitsubishi Chemical Holdings Corporation; phenol novolac epoxy resin)
E-2: Denacol DLC-402 (from Nagase ChemteX Corporation)
E-3: Denacol EX-321L (from Nagase ChemteX Corporation)
E-4: Celloxide 2021P (from Daicel Corporation)
E-5: TAKENATE B-870N (from Mitsui Chemicals, Inc.)
E-6: Desmodur BL4265SN (from Sumika Bayer Urethane Co., Ltd.)
E-7: Desmodur VPLS2078/2 (from Sumika Bayer Urethane Co., Ltd.)
E-8: DURANATE 17B-60P (from Asahi Kasei Chemicals Corp.)
E-9: JER828 (from Mitsubishi Chemical Holdings Corporation)
E-10: JER1007 (from Mitsubishi Chemical Holdings Corporation)
F-1: DBA (brand name from Kawasaki Kasei Chemicals Ltd.; 9,10-dibutoxyanthracene)
F-2: NBCA (brand name from Kurogane Kasei Co., Ltd.; 10-butylacridone)
G-1: 1,5-Diazabicyclo[4.3.0]-5-nonene
G-2: Triphenylimidazole
G-3: A basic compound represented by the structural formula shown below H-1: A perfluoroalkyl-containing nonionic surfactant represented by the structural formula shown below H-2: Silicone surfactant SH-8400 (from DowCorning Toray Silicone Co., Ltd.)

I-1: IRGANOX 1035 (from BASF)

I-2: IRGANOX 1098 (from BASF)

I-3: AO-60 (from ADEKA CORPORATION).

B'-28
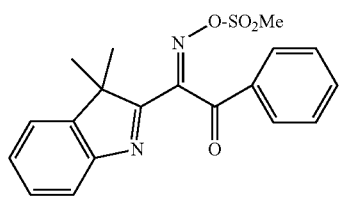

B'-29
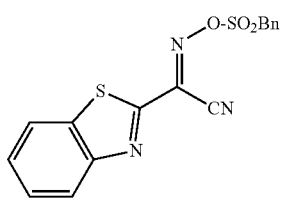

B'-30
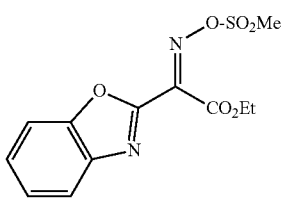

D-1
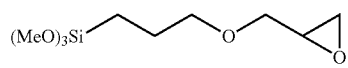

G-3
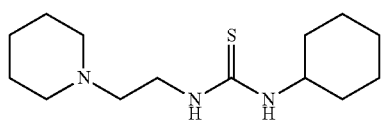

F-1
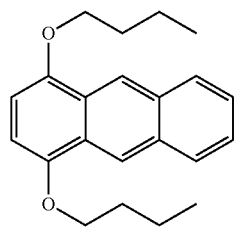

F-2
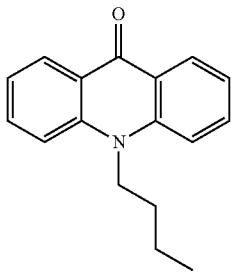

H-1
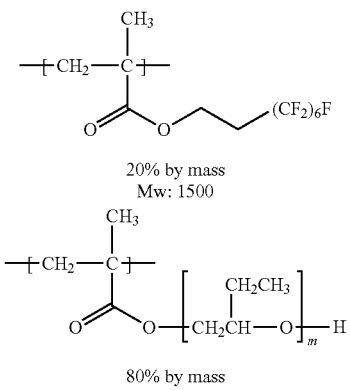

<Evaluation of Sensitivity>

Each photosensitive resin composition was applied on a glass substrate (Corning 1737, thickness 0.7 mm (from Corning Incorporated)) by slot die coating, and then prebaked on a hot plate at 90° C. for 120 seconds to vaporize the solvent, whereby a photosensitive resin composition layer having a thickness of 3.0 μm was formed.

Then, the resulting photosensitive resin composition layer was exposed through a given mask using MPA 5500CF (high pressure mercury lamp) from Canon Inc. Then, the exposed photosensitive composition layer was developed with an alkaline developer (a 0.4% by weight aqueous tetramethylammonium hydroxide solution) at 23° C. for 60 seconds, and then rinsed with ultrapure water for 20 seconds.

The optimal i-line exposure dose (Eopt) at which 10 μm line and space patterns are resolved with a top-to-bottom line width ratio of 1:1 by these operations was determined as sensitivity.

1: less than 20 mJ/cm$^2$;
2: 20 mJ/cm$^2$ or more and less than 60 mJ/cm$^2$;
3: 60 mJ/cm$^2$ or more and less than 100 mJ/cm$^2$;
4: 100 mJ/cm$^2$ or more.

<Evaluation of Storage Stability in Solution>

The viscosity of each photosensitive resin composition immediately after it has been prepared (initial viscosity) and the viscosity of each photosensitive resin composition after storage at 30° C. for 2 weeks (viscosity over time) were measured with a cone and plate viscometer (from Toki Sangyo Co., Ltd).

Evaluation Criteria are as Follows:
4: changes in viscosity over time of 15% or more when evaluated relatively to the initial viscosity (100%);
3: changes in viscosity of 10% or more and less than 15%;
2: changes in viscosity of 5% or more and less than 10%;
1: changes in viscosity of less than 5%.

<Evaluation of Transparency after Heating>

Each photosensitive resin composition was applied on a glass substrate (Corning 1737, thickness 0.7 mm (from Corning Incorporated)) by slot die coating, and then heated on a hot plate at 90° C. for 120 seconds to vaporize the solvent, whereby a photosensitive resin composition layer having a thickness of 3.0 m was formed.

The resulting photosensitive resin composition layer was exposed by the exposure system PLA-501F (ultra-high pressure mercury lamp) from Canon Inc. at a cumulative dose of 300 mJ/cm$^2$ (irradiance: 20 mW/cm$^2$, i-line), and then this substrate was heated at 230° C. in an oven 1 hour to give a cured film.

The light transmittance of the glass substrate having this cured film was measured by the spectrophotometer "Model 150-20 Double Beam (from Hitachi, Ltd.)" at a wavelength ranging from 400 to 800 nm.

Evaluation Criteria are as Follows:
1: 96% or more;
2: 94% or more and less than 96%;
3: 92% or more and less than 94%;
4: less than 92%.

TABLE 2

|  | Polymer (A) | Photoacid generators (B) | Alkoxysilane (D) | Crosslinking agent (E) | Sensitizer (F) | Basic compound (G) |
|---|---|---|---|---|---|---|
| Example 1 | A-1 | B-1 | D-1 | E-1 | F-1 | G-1, G-2 |
| Example 2 | A-1 | B-1 | D-1 | E-1 | — | G-1, G-2 |
| Example 3 | A-2 | B-2 | D-1 | E-1 | — | G-3 0.11 parts |
| Example 4 | A-3 | B-3 | — | E-1 | F-1 | G-1, G-2 |
| Example 5 | A-3:A-4:A-5 = 0.4:0.3:0.3 | B-4 | D-1 | E-1 | F-1 | G-1, G-2 |
| Example 6 | A-3:A-5 = 0.5:0.5 | B-5 | D-1 | E-1 | — | G-1, G-2 |
| Example 7 | A-4:A-6 = 0.4:0.6 | B-6 | D-1 | E-1 | F-1 | G-1, G-2 |
| Example 8 | A-5:A-7 = 0.35:0.65 | B-7 | D-1 | E-1 | — | G-1, G-2 |
| Example 9 | A-2:A-5:A-7 = 0.3:0.4:0.3 | B-8 | D-1 | — | — | G-3 0.11 parts |
| Example 10 | A-8 | B-9 | D-1 | E-1 | F-2 | G-1, G-2 |
| Example 11 | A-1:A-9 = 0.7:0.3 | B-10 | D-1 | E-1 | F-1 | G-3 0.11 parts |
| Example 12 | A-1:A-4:A-10 = 0.3:0.3:0.4 | B-11 | D-1 | E-1 | F-1 | G-1, G-2 |
| Example 13 | A-11 | B-12 | D-1 | E-1 | F-1 | G-1, G-2 |
| Example 14 | A-12 | B-13 | D-1 | E-1 | F-1 | G-3 0.11 parts |
| Example 15 | A-13 | B-14 | D-1 | — | — | G-1, G-2 |
| Example 16 | A-14 | B-15 | D-1 | E-1 | F-1 | G-3 0.11 parts |
| Example 17 | A-11:A-15 = 0.8:0.2 | B-1 | D-1 | E-1 | F-1 | G-1, G-2 |
| Example 18 | A-3:A-16 = 0.75:0.25 | B-3 | D-1 | E-1 | — | G-3 0.11 parts |
| Example 19 | A-3:A-9:A-16 = 0.4:0.4:0.2 | B-6 | D-1 | E-1 | F-1 | G-1, G-2 |
| Example 20 | A-17 | B-1 | D-1 | — | — | G-3 0.11 parts |
| Example 21 | A-18 | B-7 | D-1 | E-1 | F-2 | G-1, G-2 |
| Example 22 | A-19 | B-9 | D-1 | E-1 | — | G-3 0.11 parts |
| Example 23 | A-20 | B-1 | D-1 | E-1 | F-1 | G-1, G-2 |
| Example 24 | A-1 | B-16 | D-1 | E-1 | F-1 | G-1, G-2 |
| Example 25 | A-2 | B-17 | D-1 | E-1 | — | G-1, G-2 |
| Example 26 | A-3 | B-18 | D-1 | E-1 | F-1 | G-1, G-2 |
| Example 27 | A-3:A-5 = 0.8:0.2 | B-19 | D-1 | E-1 | — | G-1, G-2 |
| Example 28 | A-4:A-6 = 0.5:0.5 | B-20 | D-1 | E-1 | F-1 | G-1, G-2 |
| Example 29 | A-3:A-4 = 0.9:0.1 | B-21 | D-1 | E-1 | F-1 | G-1, G-2 |
| Example 30 | A-1 | B-22 | D-1 | E-1 | F-1 | G-1, G-2 |
| Example 31 | A-3:A-5:A-6 = 0.4:0.3:0.3 | B-23 | D-1 | E-1 | — | G-1, G-2 |
| Example 32 | A-2 | B-24 | D-1 | E-1 | F-1 | G-1, G-2 |
| Example 33 | A-3 | B-25 | D-1 | E-1 | F-1 | G-1, G-2 |
| Example 34 | A-2 | B-26 | D-1 | E-1 | F-1 | G-3 0.11 parts |
| Example 35 | A-3 | B-27 | D-1 | E-1 | F-1 | G-1, G-2 |
| Example 36 | A-2:A-4 = 0.9:0.1 | B-9 | D-1 | E-1 | — | G-1, G-2 |
| Example 37 | A-4:A-5:A-6 = 0.5:0.1:0.4 | B-23 | D-1 | E-1 | — | G-1, G-2 |
| Example 38 | A-4:A-6 = 0.55:0.45 | B-9 | D-1 | E-1 | — | G-3 0.11 parts |
| Example 39 | A-2:A-5 = 0.8:0.2 | B-23 | D-1 | E-1 | — | G-1, G-2 |
| Example 40 | A-3:A-5:A-6 = 0.4:0.3:0.3 | B-9 | D-1 | E-1 | — | G-1, G-2 |
| Example 41 | A-4:A-6 = 0.5:0.5 | B-23 | D-1 | E-1 | — | G-3 0.11 parts |
| Example 42 | A-4:A-5:A-6 = 0.5:0.1:0.4 | B-9 | D-1 | E-1 | — | G-1, G-2 |
| Example 43 | A-3:A-4 = 0.9:0.1 | B-23 | D-1 | E-1 | — | G-1, G-2 |
| Example 44 | A-2:A-5 = 0.8:0.2 | B-9 | D-1 | E-1 | — | G-1, G-2 |
| Example 45 | A-3:A-4 = 0.9:0.1 | B-1 | D-1 | E-1 | F-1 | G-1, G-2 |
| Example 46 | A-2:A-5 = 0.8:0.2 | B-1 | D-1 | E-1 | F-1 | G-1, G-2 |
| Comp. Exam. 1 | A-1 | B'-28 | D-1 | E-1 | — | G-1, G-2 |
| Comp. Exam. 2 | A-1 | B'-29 | D-1 | E-1 | F-1 | G-1, G-2 |
| Comp. Exam. 3 | A-3 | B'-30 | — | E-1 | F-1 | G-1, G-2 |

|  | Surfactant (H) | Solvent (C) | Evaluation | | |
|---|---|---|---|---|---|
|  |  |  | Sensitivity | Storage stability | Transparency after heating |
| Example 1 | H-1 | C-1 | 2 | 1 | 1 |
| Example 2 | H-1:H-2 = 0.5:0.5 | C-1 | 2 | 1 | 1 |
| Example 3 | H-1 | C-1 | 2 | 1 | 2 |
| Example 4 | H-1:H-2 = 0.5:0.5 | C-1 | 1 | 1 | 1 |

TABLE 2-continued

| | | | | | |
|---|---|---|---|---|---|
| Example 5 | H-1 | C-1 | 2 | 1 | 1 |
| Example 6 | H-1:H-2 = 0.5:0.5 | C-1 | 2 | 2 | 1 |
| Example 7 | — | C-1 | 1 | 1 | 1 |
| Example 8 | H-1:H-2 = 0.5:0.5 | C-1 | 2 | 1 | 1 |
| Example 9 | H-1 | C-1 | 1 | 1 | 1 |
| Example 10 | H-1 | C-1 | 1 | 1 | 2 |
| Example 11 | H-1 | C-1 | 1 | 1 | 2 |
| Example 12 | H-1:H-2 = 0.5:0.5 | C-1 | 1 | 2 | 3 |
| Example 13 | H-1:H-2 = 0.5:0.5 | C-1 | 1 | 1 | 1 |
| Example 14 | H-1:H-2 = 0.5:0.5 | C-1 | 1 | 1 | 2 |
| Example 15 | H-1:H-2 = 0.5:0.5 | C-1 | 1 | 1 | 1 |
| Example 16 | H-1:H-2 = 0.5:0.5 | C-1 | 1 | 1 | 2 |
| Example 17 | H-1:H-2 = 0.5:0.5 | C-1 | 1 | 1 | 1 |
| Example 18 | H-1:H-2 = 0.5:0.5 | C-1 | 2 | 1 | 1 |
| Example 19 | H-1:H-2 = 0.5:0.5 | C-1 | 1 | 1 | 1 |
| Example 20 | H-1:H-2 = 0.5:0.5 | C-1 | 2 | 1 | 1 |
| Example 21 | H-1:H-2 = 0.5:0.5 | C-1 | 1 | 1 | 2 |
| Example 22 | H-1:H-2 = 0.5:0.5 | C-1 | 1 | 1 | 1 |
| Example 23 | H-1 | C-1 | 1 | 1 | 1 |
| Example 24 | H-1 | C-1 | 2 | 1 | 1 |
| Example 25 | H-1 | C-1 | 2 | 1 | 1 |
| Example 26 | H-1 | C-1 | 1 | 1 | 1 |
| Example 27 | H-1 | C-1 | 1 | 1 | 1 |
| Example 28 | H-1 | C-1 | 1 | 1 | 2 |
| Example 29 | H-1 | C-1 | 1 | 3 | 2 |
| Example 30 | H-1 | C-1 | 1 | 3 | 2 |
| Example 31 | H-1 | C-1 | 1 | 1 | 1 |
| Example 32 | H-1 | C-1 | 1 | 1 | 2 |
| Example 33 | H-1 | C-1 | 2 | 1 | 1 |
| Example 34 | H-1 | C-1 | 1 | 1 | 1 |
| Example 35 | H-1 | C-1 | 1 | 1 | 1 |
| Example 36 | H-1 | C-1 | 1 | 1 | 1 |
| Example 37 | H-1 | C-1 | 1 | 1 | 2 |
| Example 38 | H-1 | C-1 | 1 | 1 | 1 |
| Example 39 | H-1 | C-1 | 1 | 1 | 1 |
| Example 40 | H-1 | C-1 | 1 | 1 | 1 |
| Example 41 | H-1 | C-1 | 1 | 1 | 2 |
| Example 42 | H-1 | C-1 | 1 | 1 | 2 |
| Example 43 | H-1 | C-1 | 1 | 1 | 1 |
| Example 44 | H-1 | C-1 | 1 | 1 | 1 |
| Example 45 | H-1 | C-1 | 1 | 1 | 1 |
| Example 46 | H-1 | C-1 | 1 | 1 | 1 |
| Comp. Exam. 1 | H-1:H-2 = 0.5:0.5 | C-1 | 4 | 1 | 2 |
| Comp. Exam. 2 | H-1:H-2 = 0.5:0.5 | C-1 | 1 | 4 | 2 |
| Comp. Exam. 3 | H-1:H-2 = 0.5:0.5 | C-1 | 2 | 1 | 4 |

TABLE 3

| | Polymer (A) | Photoacid generators (B) | Alkoxysilane (D) | Crosslinking agent (E) | Sensitizer (F) | Basic compound (G) |
|---|---|---|---|---|---|---|
| Example 47 | A-1 | B-1 | D-1 | E-1 | F-1 | G-1, G-2 |
| Example 48 | A-4:A-5:A-6 = 0.4:0.15:0.45 | B-1 | D-1 | E-1 | — | G-3 0.06 parts |
| Example 49 | A-4:A-5:A-6 = 0.4:0.15:0.45 | B-9 | D-1 | E-1 | — | G-3 0.06 parts |
| Example 50 | A-4:A-5:A-6 = 0.4:0.15:0.45 | B-8 | D-1 | E-1 | — | G-3 0.06 parts |
| Example 51 | A-4:A-5:A-6 = 0.4:0.15:0.45 | B-23 | D-1 | E-1 | — | G-3 0.06 parts |
| Example 52 | A-4:A-5:A-6 = 0.4:0.15:0.45 | B-9 | D-1 | E-4:E-6 = 0.25:0.75 | — | G-3 0.06 parts |
| Example 53 | A-4:A-5:A-6 = 0.4:0.15:0.45 | B-23 | D-1:D-2 = 0.8:0.2 | E-1 | — | G-3 0.06 parts |
| Example 54 | A-4:A-5:A-6 = 0.4:0.15:0.45 | B-8 | D-1 | E-1 | — | G-3 0.06 parts |
| Example 55 | A-4:A-5:A-6:A-21 = 0.4:0.15:0.4:0.05 | B-23 | D-1 | E-1:E-4:E-8 = 0.8:0.1:0.1 | — | G-3 0.06 parts |
| Example 56 | A-4:A-5:A-6:A-22 = 0.4:0.15:0.4:0.05 | B-23 | D-1 | E-1:E-4:E-8 = 0.8:0.1:0.1 | — | G-3 0.06 parts |
| Example 57 | A-4:A-5:A-7:A-21 = 0.4:0.15:0.4:0.05 | B-23 | D-1 | E-1:E-4:E-8 = 0.8:0.1:0.1 | — | G-3 0.06 parts |
| Example 58 | A-4:A-5:A-6:A-22 = 0.4:0.15:0.4:0.05 | B-9 | D-1 | E-1:E-4:E-8 = 0.8:0.1:0.1 | — | G-3 0.06 parts |

TABLE 3-continued

| Example | A:ratio | B | D | E:ratio | F | G |
|---|---|---|---|---|---|---|
| Example 59 | A-4:A-6:A-22 = 0.45:0.5:0.05 | B-9 | D-1 | E-3:E-4:E-8 = 0.4:0.3:0.3 | F-1 | G-3 0.06 parts |
| Example 60 | A-4:A-6:A-22 = 0.45:0.5:0.05 | B-9 | D-1 | E-3:E-4:E-8 = 0.4:0.3:0.3 | F-2 | G-3 0.06 parts |
| Example 61 | A-4:A-6:A-22 = 0.45:0.5:0.05 | B-23 | D-1 | E-3:E-4:E-8 = 0.4:0.3:0.3 | F-2 | G-3 0.06 parts |
| Example 62 | A-4:A-5:A-6:A-2 = 0.4:0.15:0.4:0.05 | B-9 | D-1 | E-1:E-4:E-8 = 0.8:0.1:0.1 | — | G-3 0.06 parts |
| Example 63 | A-4:A-5:A-7:A-2 = 0.4:0.15:0.4:0.05 | B-9 | D-1 | E-1:E-4:E-8 = 0.8:0.1:0.1 | — | G-3 0.06 parts |
| Example 64 | A-4:A-5:A-6:A-22 = 0.4:0.15:0.4:0.05 | B-9 | D-1 | E-4:E-5:E-8 = 0.2:0.4:0.4 | — | G-1, G-2 |
| Example 65 | A-4:A-5:A-6:A-22 = 0.4:0.15:0.4:0.05 | B-9 | D-1 | E-4:E-6:E-8 = 0.2:0.4:0.4 | — | G-1, G-2 |
| Example 66 | A-4:A-5:A-6:A-22 = 0.4:0.15:0.4:0.05 | B-9 | D-1 | E-4:E-7:E-8 = 0.2:0.4:0.4 | — | G-1, G-2 |
| Example 67 | A-4:A-5:A-6:A-22 = 0.4:0.15:0.4:0.05 | B-9 | D-1:D-2 = 0.8:0.2 | E-3:E-4:E-5:E-8 = 0.2:0.2:0.3:0.3 | — | G-1, G-2 |
| Example 68 | A-4:A-5:A-6:A-22 = 0.4:0.15:0.4:0.05 | B-9 | D-1:D-2 = 0.8:0.2 | E-3:E-4:E-6:E-8 = 0.2:0.2:0.3:0.3 | — | G-1, G-2 |
| Example 69 | A-4:A-5:A-6:A-22 = 0.4:0.15:0.4:0.05 | B-9 | D-1:D-2 = 0.8:0.2 | E-3:E-4:E-7:E-8 = 0.2:0.2:0.3:0.3 | — | G-1, G-2 |
| Example 70 | A-4:A-5:A-6:A-22 = 0.4:0.15:0.4:0.05 | B-9 | D-1:D-2 = 0.8:0.2 | E-3:E-4:E-6:E-8 = 0.2:0.2:0.3:0.3 | — | G-3 0.06 parts |
| Example 71 | A-4:A-5:A-6:A-22 = 0.4:0.15:0.4:0.05 | B-23 | D-1:D-2 = 0.8:0.2 | E-3:E-4:E-5:E-8 = 0.2:0.2:0.3:0.3 | — | G-1, G-2 |
| Example 72 | A-4:A-5:A-7 = 0.4:0.15:0.45 | B-23 | D-1:D-2 = 0.8:0.2 | E-1:E-3:E-6 = 0.8:0.1:0.1 | — | G-3 0.06 parts |
| Example 73 | A-4:A-5:A-6 = 0.4:0.15:0.45 | B-9 | D-1:D-2 = 0.8:0.2 | E-4:E-8 = 0.2:0.8 | — | G-1, G-2 |
| Example 74 | A-4:A-5:A-6 = 0.4:0.15:0.45 | B-9 | D-1 | E-4:E-8 = 0.2:0.8 | — | G-1, G-2 |
| Example 75 | A-4:A-5:A-6:A-22 = 0.4:0.15:0.4:0.05 | B-9 | D-1 | E-4:E-8 = 0.2:0.8 | — | G-3 0.06 parts |

| | Surfactant (H) | Solvent (C) | Solvent (C) | Evaluation | | |
|---|---|---|---|---|---|---|
| | | | | Sensitivity | Storage stability | Transparency after heating |
| Example 47 | H-1 | I-1 | C-1 | 2 | 1 | 1 |
| Example 48 | H-1 | I-1 | C-1 | 2 | 1 | 1 |
| Example 49 | H-1 | I-1 | C-1 | 1 | 1 | 1 |
| Example 50 | H-1 | I-1 | C-1 | 1 | 1 | 1 |
| Example 51 | H-1 | I-1 | C-1 | 1 | 1 | 1 |
| Example 52 | H-1 | — | C-1 | 1 | 1 | 1 |
| Example 53 | H-1 | — | C-1 | 1 | 1 | 1 |
| Example 54 | H-1 | I-1:I-3 = 0.5:0.5 | C-1 | 1 | 1 | 1 |
| Example 55 | H-1 | I-1:I-3 = 0.5:0.5 | C-1 | 1 | 1 | 1 |
| Example 56 | H-1 | I-1:I-3 = 0.5:0.5 | C-1 | 1 | 1 | 1 |
| Example 57 | H-1 | I-1:I-3 = 0.5:0.5 | C-1 | 1 | 1 | 1 |
| Example 58 | H-1 | I-1:I-3 = 0.5:0.5 | C-1 | 1 | 1 | 1 |
| Example 59 | H-1 | — | C-2 | 1 | 1 | 2 |
| Example 60 | H-1 | — | C-2 | 2 | 1 | 2 |
| Example 61 | H-1 | — | C-2 | 2 | 1 | 2 |
| Example 62 | H-1 | I-1:I-2 = 0.5:0.5 | C-2 | 1 | 1 | 1 |
| Example 63 | H-1 | I-1:I-2 = 0.5:0.5 | C-2 | 1 | 1 | 1 |
| Example 64 | H-1 | I-1:I-2 = 0.5:0.5 | C-1 | 1 | 1 | 1 |
| Example 65 | H-1 | I-1:I-2 = 0.5:0.5 | C-1 | 1 | 1 | 1 |
| Example 66 | H-1 | I-1:I-2 = 0.5:0.5 | C-1 | 1 | 1 | 1 |

TABLE 3-continued

| | | | | | | |
|---|---|---|---|---|---|---|
| Example 67 | H-1 | I-1:I-2 = 0.5:0.5 | C-1:C-2:C-3 = 0.45:0.5:0.05 | 1 | 1 | 1 |
| Example 68 | H-1 | I-1:I-2 = 0.5:0.5 | C-1:C-2:C-3 = 0.45:0.5:0.05 | 1 | 1 | 1 |
| Example 69 | H-1 | I-1:I-2 = 0.5:0.5 | C-1:C-2:C-3 = 0.45:0.5:0.05 | 1 | 1 | 1 |
| Example 70 | H-1 | I-1:I-2 = 0.5:0.5 | C-1:C-2:C-3 = 0.45:0.5:0.05 | 1 | 1 | 1 |
| Example 71 | H-1 | I-1:I-2 = 0.5:0.5 | C-1:C-2:C-3 = 0.45:0.5:0.05 | 1 | 1 | 1 |
| Example 72 | H-1 | — | C-2 | 1 | 1 | 1 |
| Example 73 | H-1 | I-1 | C-1:C-3 = 0.95:0.05 | 1 | 1 | 1 |
| Example 74 | H-1 | — | C-1:C-2 = 0.5:0.5 | 1 | 1 | 2 |
| Example 75 | H-1 | — | C-1:C-2 = 0.5:0.5 | 1 | 1 | 2 |

TABLE 4

| | Polymer (A) | Photoacid generators (B) | Alkoxysilane (D) | Crosslinking agent (E) | Sensitizer (F) | Basic compound (G) | Surfactant (H) | Antioxidant (I) | Solvent (C) | Evaluation Sensitivity | Storage stability | Transparency after heating |
|---|---|---|---|---|---|---|---|---|---|---|---|---|
| Example 76 | A-4:A-5:A-6 = 0.4:0.15:0.45 | B-9 | D-1 | E-4:E-8 = 0.2:0.8 | — | — | H-1 | I-3 | C-1:C-2 = 0.5:0.5 | 1 | 1 | 1 |
| Example 77 | A-4:A-5:A-6:A-22 = 0.4:0.15:0.4:0.05 | B-9 | D-1 | E-4:E-8 = 0.2:0.8 | — | G-3 0.06 parts | H-1 | I-3 | C-1:C-2 = 0.5:0.5 | 1 | 1 | 1 |
| Example 78 | A-4:A-5:A-7 = 0.4:0.15:0.45 | B-8 | D-1:D-2 = 0.8:0.2 | E-2:E-5 = 0.4:0.6 | — | G-1, G-2 | H-1;H-2 = 0.5:0.5 | I-2 | C-1:C-3 = 0.95:0.05 | 1 | 1 | 1 |
| Example 79 | A-4:A-5:A-7 = 0.4:0.15:0.45 | B-8 | D-1 | E-2:E-5 = 0.4:0.6 | — | G-1, G-2 | H-1;H-2 = 0.5:0.5 | — | C-1:C-2 = 0.5:0.5 | 1 | 1 | 1 |
| Example 80 | A-4:A-5:A-7:A-21 = 0.4:0.15:0.4:0.05 | B-8 | D-1 | E-2:E-5 = 0.4:0.6 | — | G-3 0.06 parts | H-1;H-2 = 0.5:0.5 | — | C-1:C-2 = 0.5:0.5 | 1 | 1 | 1 |
| Example 81 | A-1 | B-9 | D-1 | E-4:E-8 = 0.2:0.8 | — | G-3 0.06 parts | H-1 | I-1;I-3 = 0.5:0.5 | C-1:C-2 = 0.5:0.5 | 2 | 1 | 2 |
| Example 82 | A-2:A-4:A-5:A-6:A-22 = 0.05:0.35:0.15:0.4:0.05 | B-9 | D-1:D-2 = 0.8:0.2 | E-3:E-4:E-5:E-6:E-7:E-8 = 0.2:0.2:0.1:0.2:0.2:0.1 | — | G-1, G-2 | H-1;H-2 = 0.5:0.5 | I-1;I-3 = 0.5:0.5 | C-1:C-2:C-3 = 0.45:0.5:0.05 | 1 | 1 | 1 |
| Example 83 | A-2:A-4:A-5:A-6:A-22 = 0.05:0.35:0.15:0.4:0.05 | B-9 | D-1:D-2 = 0.8:0.2 | E-3:E-4:E-5:E-6:E-7:E-8 = 0.2:0.2:0.1:0.2:0.2:0.1 | — | G-3 0.06 parts | H-1;H-2 = 0.5:0.5 | I-1;I-3 = 0.5:0.5 | C-1:C-2:C-3 = 0.45:0.5:0.05 | 1 | 1 | 1 |
| Example 84 | A-2:A-4:A-5:A-6:A-22 = 0.05:0.35:0.15:0.4:0.05 | B-9 | D-1:D-2:D-3 = 0.7:0.2:0.1 | E-3:E-4:E-5:E-6:E-7:E-8:E-9 = 0.2:0.2:0.1:0.2:0.1:0.1:0.1 | F-1 | G-3 0.06 parts | H-1;H-2 = 0.5:0.5 | I-1;I-3 = 0.5:0.5 | C-1:C-2:C-3 = 0.45:0.5:0.05 | 2 | 1 | 1 |
| Example 85 | A-2:A-4:A-5:A-6:A-22 = 0.05:0.35:0.15:0.4:0.05 | B-9 | D-1:D-2:D-3 = 0.7:0.2:0.1 | E-3:E-4:E-5:E-6:E-7:E-8:E-10 = 0.2:0.2:0.1:0.1:0.1:0.2:0.1 | F-1 | G-3 0.06 parts | H-1;H-2 = 0.5:0.5 | I-1;I-3 = 0.5:0.5 | C-1:C-2:C-3 = 0.45:0.5:0.05 | 1 | 1 | 1 |
| Example 86 | A-2:A-4:A-5:A-6:A-22 = 0.05:0.35:0.15:0.4:0.05 | B-9 | D-1:D-2:D-3 = 0.7:0.2:0.1 | E-1:E-3:E-4:E-5:E-6:E-7:E-8:E-10 = 0.1:0.1:0.2:0.1:0.2:0.1:0.1:0.1 | F-1 | G-1, G-2 | H-1;H-2 = 0.5:0.5 | I-1;I-2;I-3 = 0.3:0.2:0.5 | C-1:C-2:C-3 = 0.45:0.5:0.05 | 1 | 1 | 1 |
| Example 87 | A-2:A-4:A-5:A-6:A-22 = 0.05:0.35:0.15:0.4:0.05 | B-9 | D-1:D-2:D-3 = 0.7:0.2:0.1 | E-1:E-3:E-4:E-5:E-6:E-7:E-8:E-10 = 0.1:0.1:0.2:0.1:0.2:0.1:0.1:0.1 | F-1 | G-3 0.06 parts | H-1;H-2 = 0.5:0.5 | I-1;I-2;I-3 = 0.3:0.2:0.5 | C-1:C-2:C-3 = 0.45:0.5:0.05 | 1 | 1 | 1 |
| Example 88 | A-2:A-4:A-5:A-6:A-22 = 0.05:0.35:0.15:0.4:0.05 | B-23 | D-1:D-2:D-3 = 0.7:0.2:0.1 | E-3:E-4:E-5:E-6:E-7:E-8:E-10 = 0.2:0.2:0.1:0.1:0.1:0.2:0.1 | F-1 | G-3 0.06 parts | H-1;H-2 = 0.5:0.5 | I-1;I-3 = 0.5:0.5 | C-1:C-2:C-3 = 0.45:0.5:0.05 | 2 | 1 | 1 |
| Example 89 | A-2:A-4:A-5:A-6:A-22 = 0.05:0.35:0.15:0.4:0.05 | B-28 | D-1:D-2:D-3 = 0.7:0.2:0.1 | E-3:E-4:E-5:E-6:E-7:E-8:E-10 = 0.2:0.2:0.1:0.1:0.1:0.2:0.1 | F-1 | G-3 0.06 parts | H-1;H-2 = 0.5:0.5 | I-1;I-3 = 0.5:0.5 | C-1:C-2:C-3 = 0.45:0.5:0.05 | 1 | 1 | 1 |
| Example 90 | A-2:A-4:A-5:A-6:A-22 = 0.05:0.35:0.15:0.4:0.05 | B-29 | D-1:D-2:D-3 = 0.7:0.2:0.1 | E-3:E-4:E-5:E-6:E-7:E-8:E-10 = 0.2:0.2:0.1:0.1:0.1:0.2:0.1 | F-1 | G-3 0.06 parts | H-1;H-2 = 0.5:0.5 | I-1;I-3 = 0.5:0.5 | C-1:C-2:C-3 = 0.45:0.5:0.05 | 2 | 1 | 1 |
| Example 91 | A-2 | B-23 | D-1 | E-1:E-3:E-4:E-8 = 0.5:0.2:0.3 | — | G-3 0.06 parts | H-1 | — | C-1:C-2 = 0.5:0.5 | 2 | 1 | 2 |
| Example 92 | A-2 | B-9 | D-1 | E-1:E-3:E-4:E-8 = 0.5:0.2:0.3 | — | G-3 0.06 parts | H-1 | — | C-1:C-2 = 0.5:0.5 | 2 | 1 | 2 |
| Example 93 | A-2:A-5 = 0.8:0.2 | B-23 | D-1 | E-1:E-4:E-8 = 0.5:0.20.3 | — | G-3 0.06 parts | H-1 | — | C-1:C-2 = 0.5:0.5 | 2 | 1 | 2 |
| Example 94 | A-2:A-5 = 0.8:0.2 | B-9 | D-1 | E-1:E-4:E-8 = 0.5:0.20.3 | — | G-3 0.06 parts | H-1 | — | C-1:C-2 = 0.5:0.5 | 2 | 1 | 2 |
| Example 95 | A-2:A-5 = 0.8:0.2 | B-23 | D-1 | E-1:E-4:E-8:E-10 = 0.5:0.2:0.2:0.1 | — | G-3 0.06 parts | H-1 | — | C-1:C-2 = 0.5:0.5 | 2 | 1 | 2 |
| Example 96 | A-2:A-5 = 0.8:0.2 | B-28 | D-1 | E-1:E-4:E-8:E-10 = 0.5:0.2:0.2:0.1 | — | G-3 0.06 parts | H-1 | — | C-1:C-2 = 0.5:0.5 | 2 | 1 | 2 |
| Comp. Exam. 4 | A-4:A-6:A-22 = 0.45:0.5:0.05 | B'-28 | D-1 | E-3:E-4:E-8 = 0.4:0.3:0.3 | F-2 | G-3 0.06 parts | H-1 | — | C-2 | 4 | 4 | 2 |
| Comp. Exam. 5 | A-4:A-6:A-22 = 0.45:0.5:0.05 | B'-29 | D-1 | E-3:E-4:E-8 = 0.4:0.3:0.3 | F-2 | G-3 0.06 parts | H-1 | — | C-2 | 1 | 1 | 2 |
| Comp. Exam. 6 | A-4:A-6:A-22 = 0.45:0.5:0.05 | B'-30 | D-1 | E-3:E-4:E-8 = 0.4:0.3:0.3 | — | G-3 0.06 parts | H-1 | — | C-2 | 2 | 1 | 4 |

The tables above show that the photosensitive resin compositions using compounds represented by formula (I) as photoacid generators are excellent in all of sensitivity, storage stability and transparency after heating. However, the Comparative examples not using any compounds represented by formula (I) as photoacid generators were found to be inferior to the Examples in any one of sensitivity, storage stability and transparency after heating.

Further, it was shown that sensitivity, storage stability and transparency after heating are totally further improved when the moiety corresponding to $R^1$ in the compounds represented by formula (I) is an alkyl group having a branched-chain structure, an alkyl group having a cyclic structure or a phenyl group.

Example 97

In Example 97, the procedures of Example 1 were repeated except that the exposure system MPA 5500CF (high pressure mercury lamp) from Canon Inc. was replaced by FX-803M (gh-line stepper) from NIKON CORPORATION. The evaluation results of sensitivity were comparable to Example 1.

Example 98

In Example 98, the procedures of Example 1 were repeated except that 355 nm laser exposure was applied by using a 355 nm laser exposure system in place of the exposure system MPA 5500CF (high pressure mercury lamp) from Canon Inc. The 355 nm laser exposure system used here was "AEGIS" from V-Technology Co., Ltd. (wavelength 355 nm, pulse width 6 nsec), and the exposure dose was measured with "PE10B-V2" from OPHIR.

The evaluation results of sensitivity were comparable to Example 1.

Example 99

The liquid crystal display device of Example 99 was obtained by forming the cured film 17 as an interlayer insulating layer in the active matrix liquid crystal display device described in FIG. 1 of Japanese Patent No. 3321003 as follows. Thus, the cured film 17 was formed as an interlayer insulating layer using the photosensitive resin composition of Example 85.

When a drive voltage was applied to the resulting liquid crystal display device, it exhibited good display characteristics, showing that it is a highly reliable liquid crystal display device.

Example 100

A liquid crystal display device similar to that of Example 99 was obtained by changing only the coating process as follows.

Thus, the photosensitive resin composition of Example 85 was applied by slot die coating, and then heated on a hot plate at 90° C. for 120 seconds to remove the solvent, whereby a photosensitive resin composition layer having a thickness of 3.0 µm was formed. The resulting coating film had a flat and even surface profile. Further, it exhibited good performance as a liquid crystal display device, similarly to Example 99.

Example 101

In Example 101, the procedures of Example 1 were repeated except that the exposure system MPA 5500CF (high pressure mercury lamp) from Canon Inc. was replaced by an exposure system using a UV-LED light source. The evaluation results of sensitivity were comparable to Example 1.

As described above, the photosensitive resin compositions of the Examples were shown to be also excellent in the shape of the formed pattern irrespective of the type of substrate and exposure system.

Example 102

A liquid crystal display device similar to that of Example 99 was obtained by changing only the coating process as follows.

Thus, the photosensitive resin composition of Example 85 was applied by slit and spin coating, and then heated on a hot plate at 90° C. for 120 seconds to remove the solvent, whereby a photosensitive resin composition layer having a thickness of 3.0 µm was formed. The resulting coating film had a flat and even surface profile. Further, it exhibited good performance as a liquid crystal display device, similarly to Example 99.

Example 103

An organic EL display device using a thin film transistor (TFT) was prepared by the following procedures (see FIG. 2).

A bottom gate TFT 1 was formed on a glass substrate 6, and an insulating layer 3 made of $Si_3N_4$ was formed to cover this TFT.

Then, a contact hole not shown in the figure was formed in this insulating layer 3, and then a wiring 2 (height 1.0 µm) to be connected with the TFT 1 through this contact hole was formed on the insulating layer 3. This wiring 2 is intended to connect TFTs 1 or an organic EL device that will be formed during a subsequent step and a TFT 1.

Further, a planarization layer 4 was formed on the insulating layer 3 to fill irregularities caused by forming the wiring 2 so that the irregularities caused by the wiring 2 were flattened. The planarization layer 4 was formed on the insulating layer 3 as follows. The photosensitive resin composition of Example 85 was applied on the substrate by spin coating, and prebaked on a hot plate (at 90° C. for 120 seconds), then irradiated with i-line (365 nm) at 45 mJ/cm² (irradiance: 20 mW/cm²) through a mask using a high pressure mercury lamp, then developed with an aqueous alkaline solution to form a pattern, and heated at 230° C. for 30 minutes.

The coatability during coating the photosensitive resin composition was good, and no wrinkles or cracks were observed in the cured film obtained after exposure, development and baking. Further, the wiring 2 had an average step height of 500 nm, and the planarization layer 4 prepared had a thickness of 2,000 nm.

Then, a bottom-emission organic EL device was formed on the resulting planarization layer 4. First, a first electrode 5 made of ITO was formed on the planarization layer 4 in such a manner that it was connected with the wiring 2 through the contact hole 7. Then, a resist was applied, prebaked, exposed through a mask having a desired pattern and developed. This resist pattern was used as a mask for patterning by wet etching using an ITO etchant. Then, the resist pattern was removed at 50° C. using a resist stripper (Remover 100 from AZ Electronic Materials). The first electrode 5 thus obtained corresponds to an anode of an organic EL device.

Then, an insulating layer 8 having a shape covering the periphery of the first electrode 5 was formed. The insulating layer 8 was formed by the same procedures as described above using the photosensitive resin composition of Example 85. Short circuits between the first electrode 5 and a second electrode to be formed during a subsequent step can be prevented by providing this insulating layer 8.

Further, a hole transport layer, an organic light emitting layer, and an electron transport layer were successively formed by vapor deposition through a mask having a desired pattern in a vacuum deposition system. Then, a second electrode made of Al was formed over the entire surface of the top of the substrate. The resulting substrate was removed from the vacuum deposition system, and sealed by adhering it to a sealing glass panel using a UV-curable epoxy resin.

By the procedures as described above, an active matrix organic EL display device comprising organic EL elements each connected with the TFT 1 for driving them was obtained. When a voltage was applied via a driving circuit, it exhibited good display characteristics, showing that it is a highly reliable organic EL display device.

1: TFT (thin film transistor)
2: wiring
3: insulating layer
4: planarization layer
5: first electrode
6: glass substrate
7: contact hole
8: insulating layer
10: liquid crystal display device
12: backlight unit
14, 15: glass substrate
16: TFT
17: cured film
18: contact hole
19: ITO transparent electrode
20: liquid crystal
22: color filter.

What is claimed is:

1. A compound represented by formula (I) below:

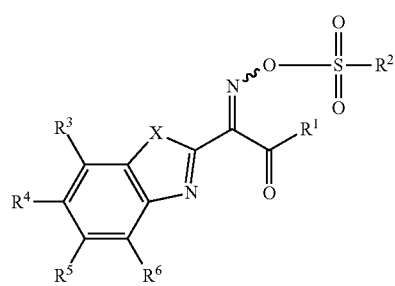

formula (I)

wherein $R^1$ represents an alkyl group; $R^2$ represents an alkyl group, an aryl group or a heteroaryl group; $R^3$ to $R^6$ each represent a hydrogen atom, an alkyl group, an aryl group or a halogen atom; or $R^3$ and $R^4$, $R^4$ and $R^5$, or $R^5$ and $R^6$ may be taken together to form an alicyclic ring or an aromatic ring; and X represents —O— or —S—.

2. The compound according to claim 1, wherein $R^1$ is an alkyl group containing 3 to 10 carbon atoms.

3. The compound according to claim 1, wherein $R^1$ is an alkyl group having a branched-chain structure, or a cyclic alkyl group.

4. The compound according to claim 1, wherein the compound represented by formula (I) is any one of compounds B-1 to B-29 shown below;

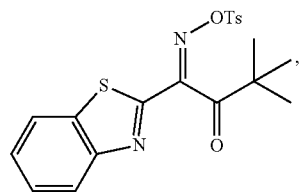
B-1

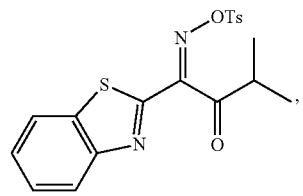
B-3

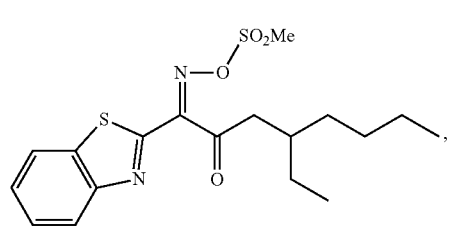
B-4

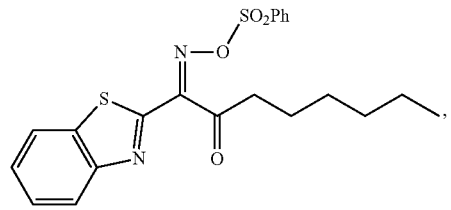
B-5

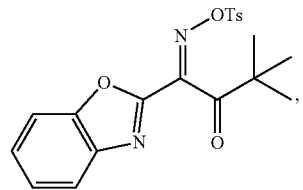
B-6

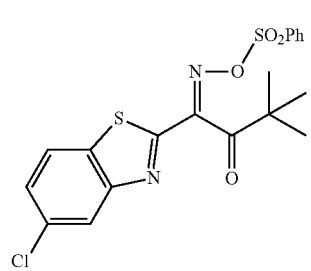
B-7

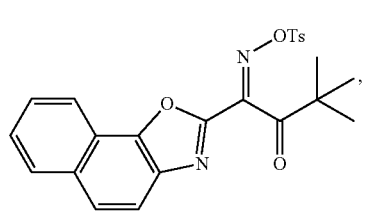
B-8

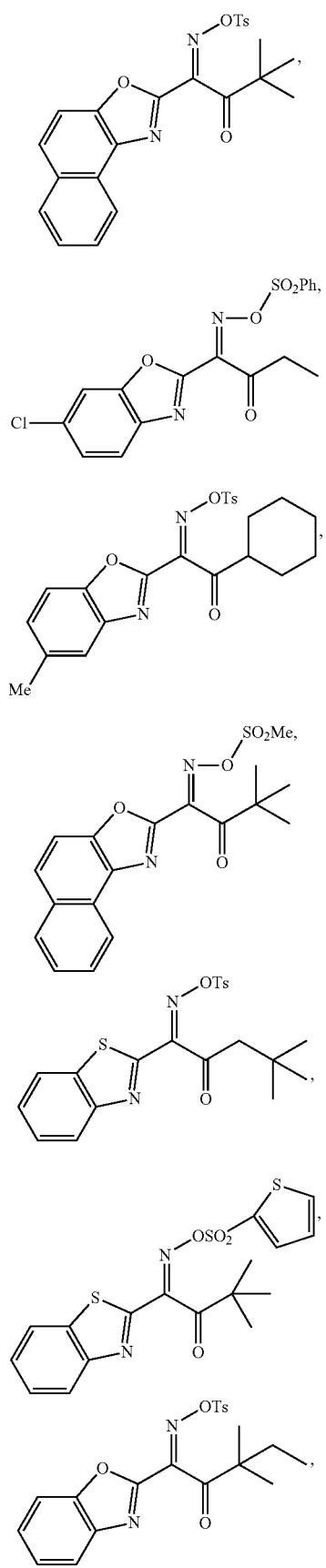
B-9
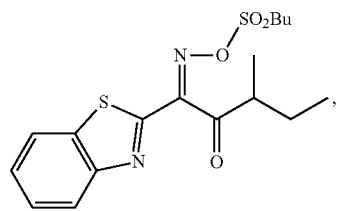
B-11
B-12
B-14
B-15
B-16
B-17
B-18
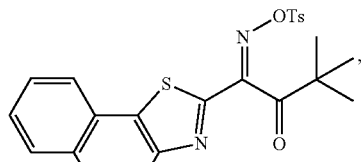
B-19
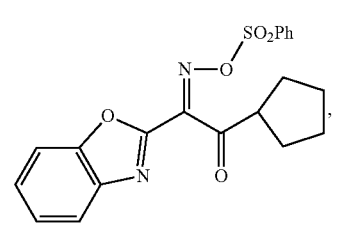
B-20
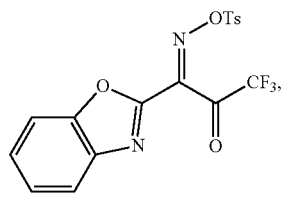
B-21
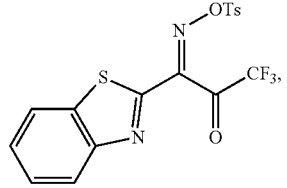
B-22
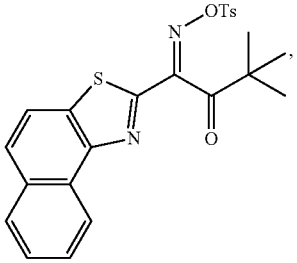
B-23
B-24
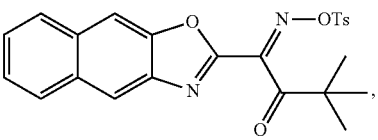
B-25
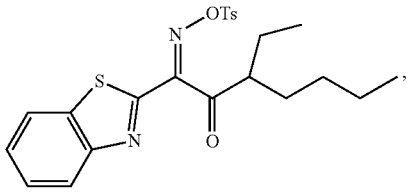

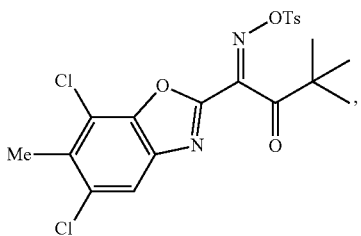
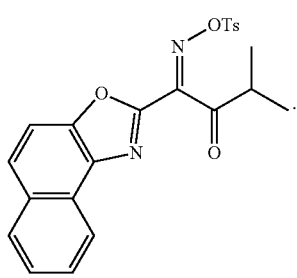
5. The compound according to claim 1, wherein R[1] represents a branched chain alkyl group containing 3 to 6 carbon atoms or a cyclic alkyl group containing 5 to 7 carbon atoms.
6. The compound according to claim 1, wherein R[1] represents an isopropyl, tert-butyl, neopentyl or cyclohexyl.
7. The compound according to claim 1, wherein R[1] represents tert-butyl.
* * * * *